United States Patent [19]

Dorsch et al.

[11] Patent Number: 5,164,111
[45] Date of Patent: Nov. 17, 1992

[54] POLYMERIZABLE LIQUID-CRYSTAL MATERIAL AND POLYMERS EXHIBITING LIQUID-CRYSTAL PHASES

[75] Inventors: Dieter Dorsch, Darmstadt; Rudolf Eidenschink, Mühltal; Andreas Wächtler, Griesheim; Bernhard Rieger, Pfungstadt; Heino Finkelmann, Freiburg, all of Fed. Rep. of Germany

[73] Assignee: Merck Patent Gesellschaft mit beschraenkter Haftung, Darmstadt, Fed. Rep. of Germany

[21] Appl. No.: 554,949

[22] Filed: Jul. 13, 1990

Related U.S. Application Data

[63] Continuation of Ser. No. 166,852, Feb. 26, 1988, abandoned.

Foreign Application Priority Data

Jun. 27, 1986 [DE] Fed. Rep. of Germany ....... 3621581

[51] Int. Cl.$^5$ .............. C09K 19/52; C09K 19/30; C09K 19/34
[52] U.S. Cl. .................. 252/299.01; 252/299.61; 252/299.63; 526/242; 526/256; 526/258; 526/266; 526/285; 526/292.1; 526/292.2; 526/292.8; 526/293; 526/299
[58] Field of Search ........... 252/299.01, 299.61, 252/299.63, 582; 428/1; 526/242, 256, 258, 266, 285, 292.1, 292.2, 292.8, 293, 299

[56] References Cited

U.S. PATENT DOCUMENTS 4,637,896  1/1987  Shannon .................. 252/299.7
4,713,196  12/1987  Praefcke et al. .......... 252/299.01

FOREIGN PATENT DOCUMENTS 0140133  5/1985  European Pat. Off. .
0172450  2/1986  European Pat. Off. .
3430482  5/1985  Fed. Rep. of Germany .

OTHER PUBLICATIONS

Shibaev, V. P. et al. Eur. Polym. J. 18, 651, 1982.
Zhou, Q-F et al. Can. J. Chem. 63, 181, 1985.
Tsvetkov, V. N. et al. Polym Prepr. (Am. Chem. Soc., Div. Polym. Chem.), 24 (2) 280, 1983.

Primary Examiner—Robert L. Stoll
Assistant Examiner—Shean C. Wu
Attorney, Agent, or Firm—Millen, White, Zelano and Branigan

[57] ABSTRACT

The invention relates to polymerizable liquid-crystal materials and to polymer materials which exhibit liquid-crystal phases and which contain, attached directly or via a spacer, mesogenic groups in which at least one transversely polarizing structural element of the formulae I to X, defined in claim 1, is present.

3 Claims, No Drawings

POLYMERIZABLE LIQUID-CRYSTAL MATERIAL AND POLYMERS EXHIBITING LIQUID-CRYSTAL PHASES

This application is a continuation of application Ser. No. 07/166,852, filed Feb. 26, 1988 now abandoned.

The invention relates to polymerizable liquid-crystal materials and to polymer materials which exhibit liquid-crystal phases and which contain, attached by a direct chemical bond or via a spacer, a mesogenic group in which at least one transversely polarizing structural element is present.

A number of liquid-crystal side-chain polymers are already known. Thus, for example, organopolysiloxanes are described in German Offenlegungsschrift 2,944,591 and EP Patent Specification 0,060,335, and polymethacrylates having mesogenic side groups are described in German Offenlegungsschrift 2,831,909 and in Springer and Weigelt, Makromol. Chem. 184 (1983) 1489.

For example, polyacrylic and polymethacrylic acid esters which are also modified with 4'-cyanobiphenyl-4-yl as the mesogenic group are known. Nematic phases of such polymer compositions are present in most cases at temperatures above 100°. Such materials also frequently exhibit crystalline behavior, associated with the lack of mesomorphic properties.

The object of the present invention was to find polymer materials which exhibit liquid-crystal phases and which do not exhibit the disadvantages described or do so only to a slight extent.

It has now been found that polymer materials which contain chemically linked mesogenic groups containing at least one transversely polarizing structural element exhibit surprisingly broad mesophase ranges, a double refraction variable within wide limits and a negative dielectric anisotropy. In addition, they can readily be processed to give articles of any desired form having anisotropic properties, and exhibit a high stability to chemicals.

The invention relates to polymer compositions which exhibit liquid-crystal phases and which contain, attached directly or via a spacer, mesogenic groups, which are characterized in that at least one of the mesogenic groups contains at least one transversely polarizing structural element corresponding to the formulae I to X:

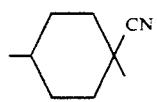 I

 II

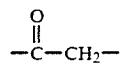 III

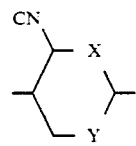 IV

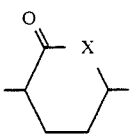 V

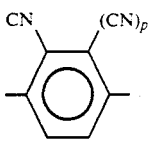 VI

 VII

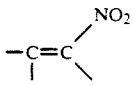 VII

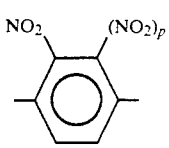 IX

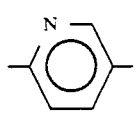 X in which X and Y independently of one another are —CH$_2$—, —O— or —S—, R is H or an alkyl group having up to 6 C atoms, T is —COO—, —OCO— or a single bond and p is 0 or 1.

The invention also relates to polymer compositions, as defined in claim 1, exhibiting liquid-crystal phases, in which the mesogenic groups correspond to the formula XI:

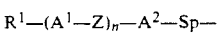    XI in which
R$^1$ is H or an alkyl group which has up to 15 C atoms and in which one or more CH$_2$ groups can also be replaced by a grouping belonging to the group comprising —O—, —S—, —O—CO—O—, —CO—, —CO—O—, —O—CO—, —CR-R'—T—, —CO—S—, —S—CO—, —CH=CH—(trans), —C(halogen)$_2$—, —SO— and —SO$_2$—, 2 heteroatoms not being attached to one another, or is halogen, CN or —NCS, A$^1$ and A$^2$ independently of one another are each an unsubstituted or a halogen— and/or CN— and/or CH$_3$— and/or NO$_2$—monosubstituted or —polysubstituted 1,4-cyclohexylene group, in which one or two non-adjacent CH$_2$ groups can also be replaced by —O— and/or —S— atoms, and/or a CH$_2$ group can also be replaced by —CO—, 1,4-phenylene group, in which one or more CH groups can also be replaced by N, a piperidine-1,4-diyl group or a 1,4-bicyclo(2.2.2)octylene group, n is 1, 2 or 3, the Zs are each —CO—O—, —O—CO—, —CH$_2$C-H$_2$—, —CRR'—T—, —CH$_2$—CO—, —CO—CH$_2$—, —CHCN—CH$_2$, —CH$_2$—CHCN—, —CHNO$_2$—, —CH=N—, —N=CH—, —NO=O—, —N=NO—, —N=N— or a single bond, Sp is alkylene which has 2-18 C atoms and in which one or two non-adjacent CH₂ groups can also be replaced by —O—, —CO—, —O—CO—, —CO—O—, —C(halogen)₂—, —CRR'—T—, —CH=CNO₂—, —CHNO₂—, —CHCN—, —CH=N— or —CH=CH—, or is a single bond, T is —COO—, —OCO— or a single bond.

R is H or an alkyl group having up to 6 C atoms, and R' is halogen or CN, subject to the proviso that at least one transversely polarizing structural element corresponding to the formulae I to X according to claim 1 is present.

The invention also relates to a process for the preparation of those polymer compositions in which compounds of the formula XII W-Spacer-M    XII in which is a mesogenic group containing at least one transversely polarizing structural element and W is a functional group capable of polymerization or grafting, are polymerized or grafted onto polymers, and to the use of such polymer compositions as organic substrates in the electronics industry for fiber and films technology or as materials for non-linear optics.

In the preceding and following text, unless anything to the contrary is expressly noted, R, T, X, Y, p, R¹, A¹, Z, n, A², Sp, R', W, M, R², A³, Z¹, m, Q¹, R³, Q² and R⁴ have the meaning indicated.

The structural element present in the mesogenic groups corresponds to one of the formula I to X. The structural elements are preferably I, VI, IX and X. The cyano group in formula I is located axially in the 1-position or 4-position.

p in the formulae VI and IX is preferably 0. X and Y are preferably a —CH₂— group, and —O— is also preferred.

The transversely polarizing structural elements of the formulae II, III, VII and VIII, which are also preferred, can be located in the wing group or in the spacer group or as bridges between two rings of the mesogenic radicals.

In formula II R is H or an alkyl group which has up to 6 C atoms and which can be linear or branched, and is, accordingly, methyl, ethyl, propyl, isopropyl, butyl, pentyl or hexyl. In this regard, H or a methyl, ethyl or propyl group is preferred. H or methyl is particularly preferred.

T in this formula is preferably a single bond or a —CO—O— group.

Accordingly, the structural elements of the subformulae IIa to IId are particularly preferred:

    IIa

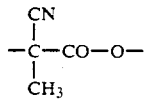    IIb

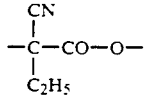    IIc

    IId

The mesogenic groups containing at least one transversely polarizing structural element of the formulae I to X preferably correspond to the formula XI.

The compounds of the formula XI embrace compounds having two rings of the partial formulae XIa to XIb, having three rings of the partial formulae XIc to XIf and having four rings of the partial formulae XIg to XIn:

R¹—A¹—Z—A²—Sp—                     XIa
R¹—A¹—A²—Sp—                        XIb
R¹—A¹—Z—A¹—Z—A²—Sp—                 XIc
R¹—A¹—A¹—A²—Sp—                     XId
R¹—A¹—Z—A¹—A²—Sp—                   XIe
R¹—A¹—A¹—Z—A²—Sp—                   XIf
R¹—A¹—Z—A¹—Z—A¹—Z—A²—Sp—            XIg
R¹—A¹—Z—A¹—A¹—A²—Sp—                XIh
R¹—A¹—A¹—Z—A¹—A²—Sp—                XIi
R¹—A¹—A¹—A¹—Z—A²—Sp—                XIj
R¹—A¹—A¹—A¹—A²—Sp—                  XIk
R¹—A¹—Z—A¹—Z—A¹—A²—Sp—              XIl
R¹—A¹—Z—A¹—A¹—Z—A²—Sp—              XIm
R¹—A¹—A¹—Z—A¹—Z—A²—Sp—              XIn

For the sake of simplicity, in the following text Cy is a 1,4-cyclohexylene group in which one or two non-adjacent CH₂ groups can also be replaced by 0 and/or S atoms, and Phe is a 1,4-phenylene group in which one or more CH groups can also be replaced by N. These groups can also be monosubstituted or polysubstituted by halogen and/or CN and/or NO₂ and/or CH₃, halogen being preferably fluorine or chlorine. The cyclohexylene group can be in the cis-1,4-configuration or in the trans-1,4-configuration. The trans-1,4-cyclohexylene group is preferred.

Bi is a 1,4-bicyclo(2.2.2)octylene group and Pip is a piperidine-1,4-diyl group.

In conformity with the formulae I to X, the transversely polarizing structural element in the partial formulae XIa to XIn can be located in R¹, A¹, Z, A² or the Sp group. This is subject to the proviso, however, that at least one transversely polarizing structural element corresponding to the formulae I to X is present.

Amongst the partial formulae XIa to XIn, those of the formulae XIa, XIb, XIc, XId, XIe, XIf, XIh, XIi and XIk are preferred. Compounds of the partial formulae XIa, XIb, XIc, XId, XIe and XIf are particularly preferred.

Examples of preferred compounds of the partial formulae XIa and XIb (Z = a single bond) are those of the formulae XIaa to XIar:

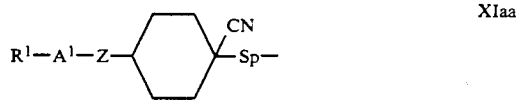    XIaa

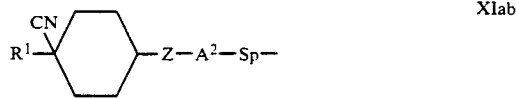    XIab

-continued

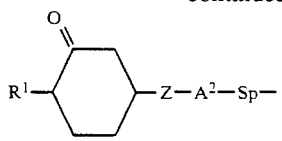 XIac

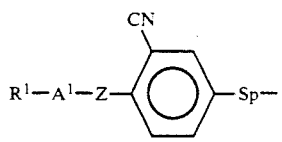 XIad

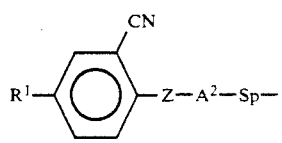 XIae

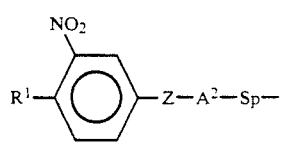 XIaf

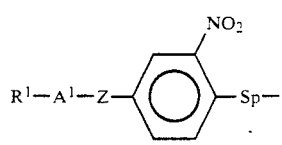 XIag

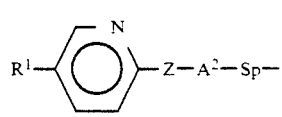 XIah

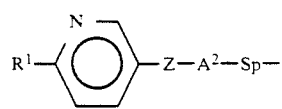 XIai

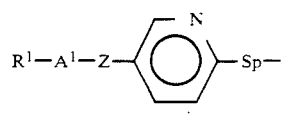 XIaj

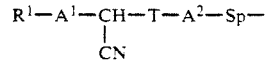 XIak

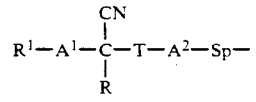 XIal

R¹—A¹—CO—CH₂—A²—Sp—    XIam

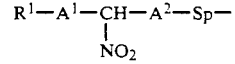 XIan

R¹—Phe—Z—Phe—Sp—    XIao
R¹—Phe—Z—Cy—Sp    XIap
R¹—Cy—Z—Phe—Sp    XIaq
R¹—Cy—Z—Cy—Sp    XIar

In the partial formulae XIao to XIar, the transversely polarizing structural element, preferably II, VII or VIII, is located in the wing groups R¹ or in the spacer group Sp.

Amongst the compounds of the partial formulae XIaa to XIar, those of the formulae XIaa, XIab, XIah, XIal and XIao are particularly preferred.

The compounds of the partial formula XIc embrace, for example, those of the partial formulae XIca to XIcs:

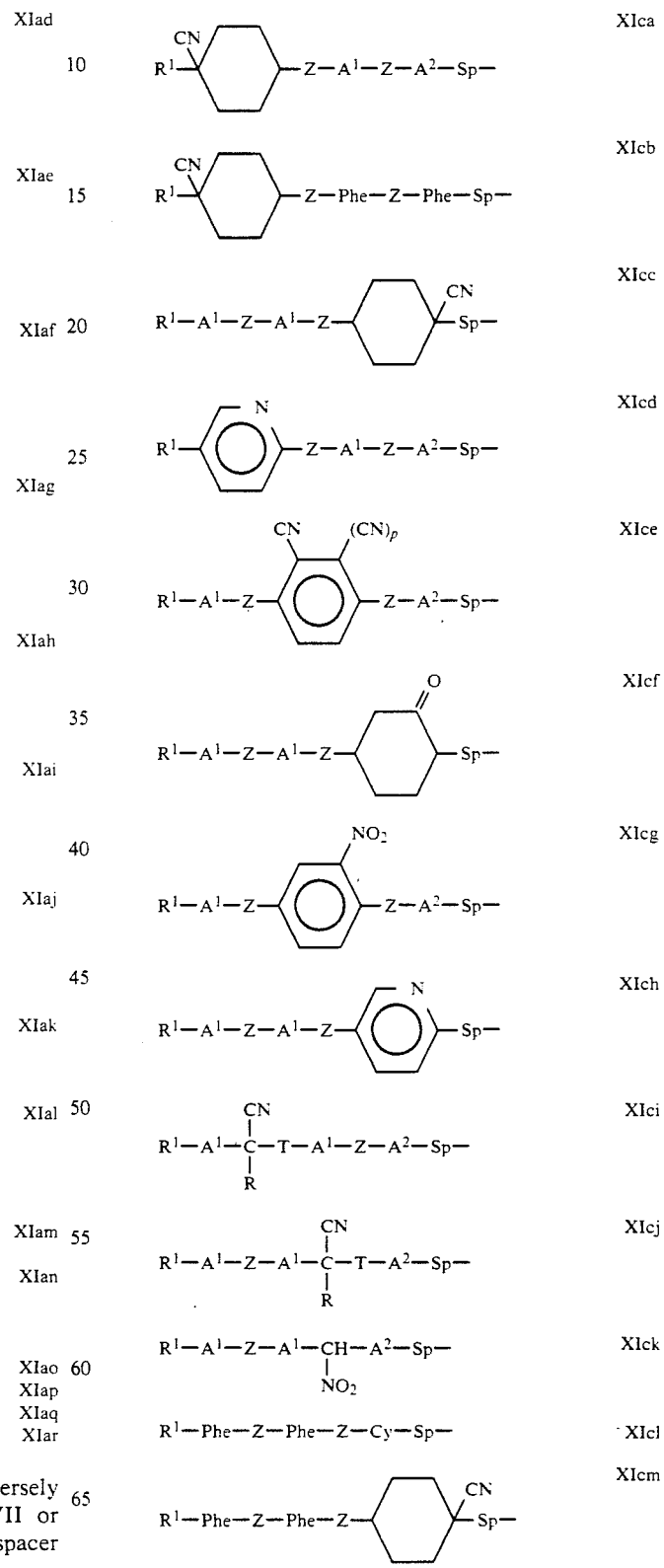

-continued $R^1$—[Cy(CN)]—Z—Phe—Z—Cy—Sp—    XIcn $R^1$—[Cy(CN)]—CO—O—Phe—OCO—Phe—Sp—    XIco $R^1$—Cy—Z—Phe—Z—Phe—Sp—    XIcp
$R^1$—Phe—Z—Cy—Z—Phe—Sp—    XIcq
$R^1$—Phe—Z—Cy—Z—Cy—Sp—    XIcr
$R^1$—Phe—Z—Phe—Z—Phe—Sp—    XIcs Amongst these, those of the formulae XIca, XIcb, XIcc, XIcd, XIdh, XIci, XIcj, XIcl, XIcm, XIco, XIcp and XIcs are particularly preferred. In the partial formulae XIcl and XIcp to XIcs the transversely polarizing structural element, preferably II, VII or VIII, is located in the wing group $R^1$ or in the spacer group Sp.

The compounds of the partial formula XId embrace, for example, those of the partial formulae XIda to XIdp:

$R^1$—[Cy(CN)]—Phe—Phe—Sp—    XIda $R^1$—Phe—Phe—[Cy(CN)]—Sp—    XIdb $R^1$—$A^1$—$A^1$—[Cy(CN)]—Sp—    XIdc $R^1$—[Cy(CN)]—$A^1$—$A^2$—Sp—    XIdd $R^1$—[Pyr]—$A^1$—$A^2$—Sp—    XIde $R^1$—[Phe(CN)(CN)$_p$]—$A^1$—$A^2$—Sp—    XIdf $R^1$—$A^1$—$A^1$—[Cy(=O)]—Sp—    XIdg $R^1$—$A^1$—[Phe(NO$_2$)(NO$_2$)$_p$]—$A^2$—Sp—    XIdh $R^1$—$A^1$—$A^1$—[Pyr]—Sp—    XIdi $R^1$—[Cy(CN)]—Phe—Cy—Sp—    XIdj $R^1$—Cy—Phe—Phe—Sp—    XIdk
$R^1$—Phe—Cy—Phe—Sp—    XIdl
$R^1$—Phe—Phe—Phe—Sp—    XIdm $R^1$—Phe—[Pyr]—Phe—Sp—    XIdn $R^1$—Phe—Cy—Cy—Sp—    XIdo
$R^1$—Cy—Cy—Cy—Sp—    XIdp

Amongst these, those of the formulae XIda, XIdb, XIdc, XIdd, XIde, XIdf, XIdk and XIdo are particularly preferred. In the partial formulae XIdk to XIdp, the transversely polarizing structural element, preferably an element of the formulae II, VII or VIII, is located in the wing group $R^1$ or in the spacer group Sp.

The compounds of the partial formula XIe preferably embrace those of the partial formulae XIea to XIer:

$R^1$—$A^1$—Z—$A^1$—[Cy(CN)]—Sp—    XIea $R^1$—[Cy(CN)]—Z—$A^1$—$A^2$—Sp—    XIeb $R^1$—$A^1$—Z—[Cy(=O)]—$A^2$—Sp—    XIec $R^1$—[Phe(CN)(CN)$_p$]—Z—$A^1$—$A^2$—Sp—    XIed $R^1$—[Pyr]—Z—$A^1$—[Cy(CN)]—Sp—    XIee $R^1$—$A^1$—Z—[Phe(NO$_2$)$_p$(NO$_2$)]—$A^2$—Sp—    XIef $R^1$—$A^1$—Z—$A^1$—[Pyr]—Sp—    XIeg

-continued

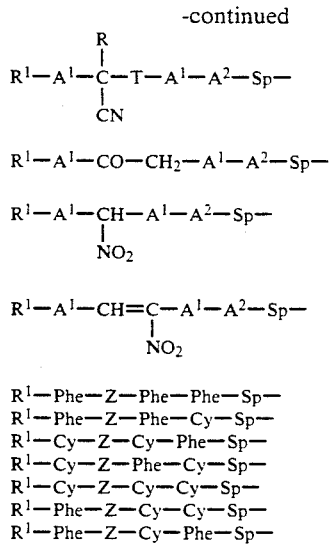

R¹—A¹—CO—CH₂—A¹—A²—Sp—  XIei

R¹—A¹—CH—A¹—A²—Sp—  XIej
         |
         NO₂

R¹—A¹—CH=C—A¹—A²—Sp—  XIek
           |
           NO₂

R¹—Phe—Z—Phe—Phe—Sp—  XIel
R¹—Phe—Z—Phe—Cy—Sp—  XIem
R¹—Cy—Z—Cy—Phe—Sp—  XIen
R¹—Cy—Z—Phe—Cy—Sp—  XIeo
R¹—Cy—Z—Cy—Cy—Sp—  XIep
R¹—Phe—Z—Cy—Cy—Sp—  XIeq
R¹—Phe—Z—Cy—Phe—Sp—  XIer

Amongst these, those of the formulae XIea, XIeb, XIee, XIef, XIeg, XIeh, XIej, XIek, XIel, XIem and XIeq are particularly preferred. In the formulae XIel to XIer the transversely polarizing structural element, preferably an element of the formulae II, VII or VIII, is located in the wing group R¹ or in the spacer group Sp.

The compounds of the partial formula XIf preferably embrace those of the partial formulae XIfa to XIfv:

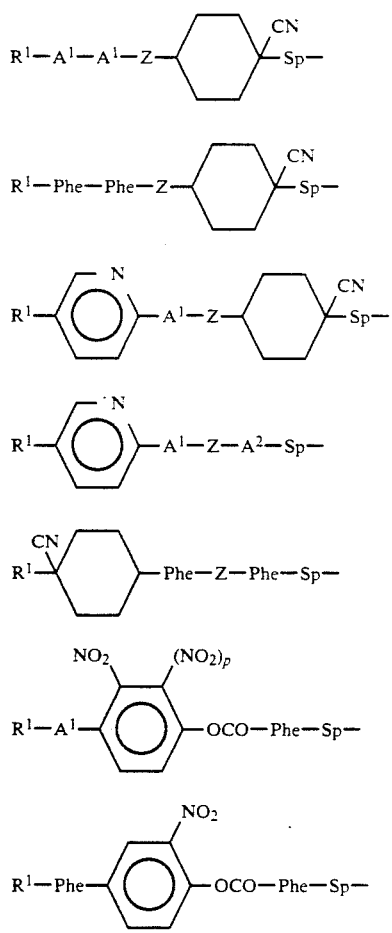

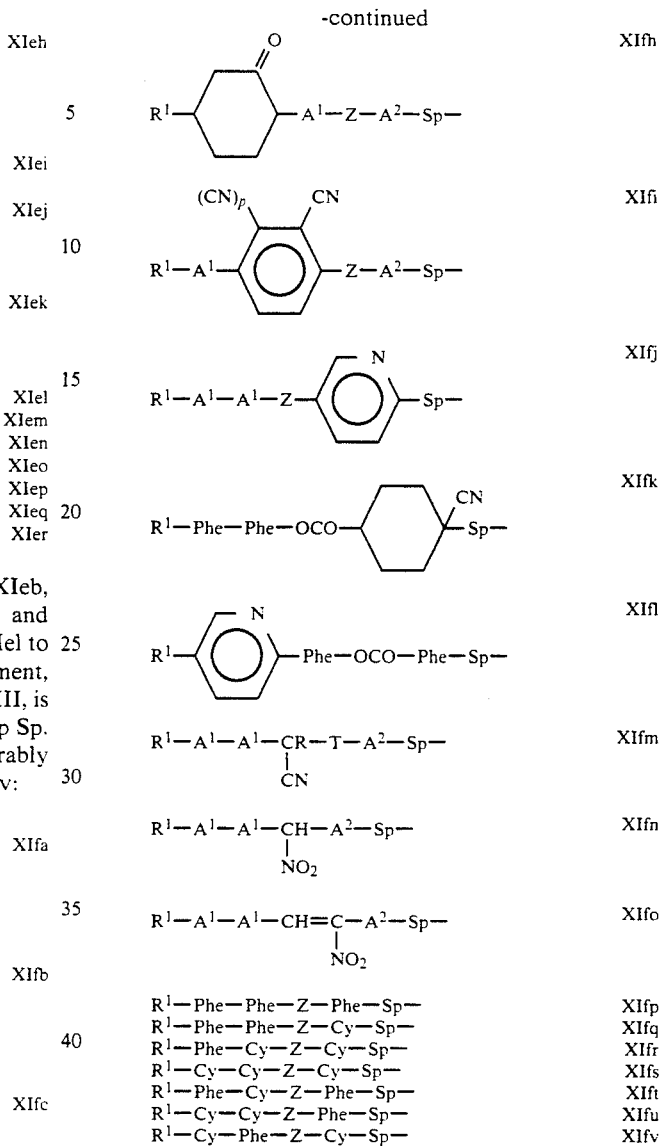

R¹—Phe—Phe—Z—Phe—Sp—  XIfp
R¹—Phe—Phe—Z—Cy—Sp—  XIfq
R¹—Phe—Cy—Z—Cy—Sp—  XIfr
R¹—Cy—Cy—Z—Cy—Sp—  XIfs
R¹—Phe—Cy—Z—Phe—Sp—  XIft
R¹—Cy—Cy—Z—Phe—Sp—  XIfu
R¹—Cy—Phe—Z—Cy—Sp—  XIfv

Amongst these those of the formulae XIfa, XIfb, XIfc, XIfd, XIfe, XIfg, XIj XIfk, XIfl, XIfm, XIfn, XIfo, XIfp and XIfq are particularly preferred. In the partial formulae XIfp to XIfv, which are also particularly preferred, the transversely polarizing structural element, preferably an element of the formulae II, VII or VIII, is located in the wing group R¹ or in the spacer group Sp.

Preferably, one or two transversely polarizing structural elements are present in the preceding and following formulae and partial formulae XI, which particularly preferably contain one transversely polarizing structural element.

In the compounds of the preceding and following formulae XI R¹ is preferably alkyl or alkoxy.

Compounds of the preceding and following formulae and partial formulae XI which are also preferred are those in which R¹ is an alkyl group in which one or more CH₂ groups, preferably one CH₂ group, have been replaced, preferably by a —CO—, —CO—O—, —O—CO—, —CRR'—T— or —C(halogen)₂ group. Halogen is fluorine, chlorine or bromine, preferably F or Cl; fluorine is particularly preferred. In these compounds T is preferably —CO—O— or a single bond, and R is preferably H or an unbranched alkyl group having up to 3 C atoms and accordingly is preferably methyl, ethyl, propyl, and also butyl, pentyl or hexyl. R is halogen or CN, preferably fluorine, chlorine or CN.

$A^1$ and $A^1$ independently of one another are each preferably 1,4-cyclohexylene which can also be substituted, monosubstitution by CN in the 1-position or 4-position being preferred, or 1,4-phenylene which can be substituted by $NO_2$, CN or halogen, or are pyridine-2,5-diyl.

n is preferably 1 or 2.

The Zs independently of one another are each preferably single bonds, —CO—O— or —O—CO—, and also preferably —CRR'—T—, —CHNO$_2$— or —CH=CNO$_2$—. R, R' and T in these formulae have the preferred meanings indicated.

Sp is preferably a linear alkylene group having 2–10 C atoms and, accordingly, is preferably ethylene, propylene, butylene, pentylene, hexylene, heptylene, octylene, nonylene or decylene, and also undecylene, dodecylene, tridecylene, tetradecylene, pentadecylene, hexadecylene, heptadecylene or octadecylene. The alkylene groups can, however, also be branched and, accordingly, are, for example, isopropylene, 1-methylpropylene, isobutylene, 2-methylbutylene, 3-methylbutylene or 2-methylpentylene. Alkylene groups in which one or two non-adjacent $CH_2$ groups have been replaced, preferably by —O—, —OCO—, —CO—O—, —CH-halogen— or —C(halogen)$_2$—, and also preferably by —CRR'—T—, —CHNO$_2$— or —CH=CNO$_2$—, are also preferred for Sp. Halogen R, R' and T in these formulae have the preferred meanings indicated.

If $R^1$ is an alkyl radical or alkoxy radical, this can be linear or branched. It is preferably linear, has 2, 3, 4, 5, 6 or 7 C atoms and is, accordingly, preferably ethyl, propyl, butyl, pentyl, hexyl, heptyl, ethoxy, propoxy, butoxy, pentoxy, hexyloxy or heptyloxy, and also methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl is preferably linear 2-oxapropyl (=methoxymethyl), 2-oxabutyl (=ethoxymethyl), 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If $R^1$ is an alkyl radical in which a CH2 group has been replaced by —CH=CH—, this radical can be linear or branched. It is preferably linear and has 2 to 10 C atoms and, accordingly, is, in particular, vinyl, prop-1-enyl, prop-2-enyl, but-1-enyl, but-2-enyl, but-3-enyl, pent-1-enyl, pent-2-enyl, pent-3-enyl, pent-4-enyl, hex-1-enyl, hex-2-enyl, hex-3-enyl, hex-4-enyl, hex-5-enyl, hept-1-enyl, hept-2-enyl, hept-3-enyl, hept-4-enyl, hept-5-enyl, hept-6-enyl, oct-1-enyl, oct-2-enyl, oct-3-enyl, oct-4-enyl, oct-5-enyl, oct-6-enyl, oct-7-enyl, non-1-enyl, non-2-enyl, non-3-enyl, non-4-enyl, non-5-enyl, non-6-enyl, non-7-enyl, non-8-enyl, dec-1-enyl, dec-2-enyl, dec-3-enyl, dec-4-enyl, dec-5-enyl, dec-6-enyl, dec-7-enyl, dec-8-enyl or dec-9-enyl.

Compounds of the formula XI having a branched wing group $R^1$ can occasionally be of importance as a result of reducing the tendency to crystallization, but are particularly of importance as chiral constituents of polymers, if they are optically active. Cholesteric polymers which can be used as thermochromic films, or polymers having tilted smectic phases which possess ferroelectric, piezoelectric, pyroelectric and/or non-linear optical properties of an even-numbered order, particularly second order, are obtained in this way.

Branched groups of this type as a rule contain not more than one chain branch. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexyloxy, 1-methylhexyloxy, 1-methylheptyloxy (=2-octyloxy), 2-oxa-3-methylbutyl, 3-oxa-4-methylpentyl, 4-methylhexyl, 2-nonyl, 2-decyl, 2-dodecyl, 6-methyloctyloxy, 6-methyloctanoyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

The formula XI embraces both the racemates of these compounds and the optical antipodes and mixtures thereof.

Amongst the compounds of the formula XI and all the partial formulae of XI, preferred compounds are those in which at least one of the radicals contained therein has one of the preferred meanings indicated.

The invention also relates to a process for the preparation of polymer materials according to claim 1 and 2.

Thus compounds of the formula XII

W-Spacer-M    XII in which M is a mesogenic group having a transversely polarizable structural element and W is a functional group capable of polymerization or grafting, can be polymerized or grafted onto polymers.

Polymerization is to be understood here as meaning both free-radical or ionic polymerization and polyaddition or polycondensation.

If W contains an alkylene group, the compounds of the formula XII can be polymerized by a free-radical or ionic mechanism. These starting compounds can also be copolymerized with further olefinically unsaturated compounds. Grafting is also possible.

If W is a hydroxyl, amino, mercapto, epoxide or carboxyl group or a reactive derivative thereof, the compounds of the formula XII can be grafted onto a polymeric backbone.

Polymerizable liquid-crystal materials of this type of the formula XII are in part known and in part they are also still novel.

The polymerizable liquid-crystal materials of the formula I', which also are a subject of the invention, are novel.

The invention therefore also relates to polymerizable liquid-crystal materials of the formula I'

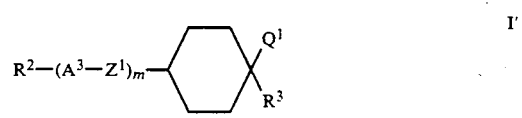

in which one of the radicals $R^2$ and $R^3$ is H or an alkyl group which has up to 15 C atoms and in which one or more $CH_2$ groups can also be replaced by a grouping belonging to the group comprising —O—, —S—, —O—CO—O—, —CO—, —CO—O—, —O—CO—, —CO—S—, —S—CO—, —CH=CH—(trans), —CRR'—T—, —C(halogen)₂—, —SO— and —SO₂—, 2 heteroatoms not being attached to one another, halogen, CN or —NCS,
and the other of the two radicals R² and R³ is then

—Q²—R⁴,

Q² is alkylene which has 3-18 C atoms and in which one or two non-adjacent CH₂ groups can also be replaced by —O—, —CO—, —O—CO—, —CO—O—, —CRR'—T—, —CH=N— or —CH=CH—, R⁴ is a vinyl group which is unsubstituted or substituted by 1, 2 or 3 F and/or Cl atoms and/or CH₃ groups, or is a carboxyl, hydroxyl, amino, mercapto or epoxide group, R is H or an alkyl group having up to 6 C atoms,
R' is halogen or CN,
T is —CO—O—, —O—CO— or a single bond,
Q¹ is alkyl or alkoxy having 1-5 C atoms, F, Cl, Br or CN,
Z¹ is —CO—O—, —O—CO—, —CH₂O—, —OCH₂—, —CH₂CH₂—, —CRR'—T— or a single bond,
the A³s independently of one another are unsubstituted or halogen-, CN- and/or CH₃-monosubstituted or -polysubstituted trans-1,4-cyclohexylene, in which one or two non-adjacent CH₂ groups can also be replaced by 0 and/or S and/or a

|
—CH₂—CH group can be replaced by

|
—N=C—, or 1,4-phenylene, in which one or more CH groups can also be replaced by N, and
m is 1, 2 or 3, subject to the proviso that, in the event that Q¹=CN, R⁴=unsubstituted vinyl and Q²=alkylene or alkyleneoxy, the alkylene group contains at least 4 C atoms.

A large number of liquid-crystal polymers are already known, for example polyacrylic and polymethacrylic acid esters modified by means of 4'-cyanobiphenyl-4-yl as a mesogenic group. Mesogenic compounds capable of reaction or polymerization are required for the preparation of liquid-crystal polymers of this type having mesogenic side groups.

Some starting materials which can be grafted onto a polymeric backbone, such as, for example:

R—⟨Cy⟩—⟨Phe⟩—(CH₂)ₙ—OH, n = 4-7 or

R—⟨Cy⟩—⟨Phe⟩—C(=O)—(CH₂)ₙ—COOH, n = 3-6 described in EP 58,981, or which can be polymerized after esterification with compounds containing an olefinically unsaturated group, are also known.

The object of the present invention was, therefore, also to find readily accessible, polymerizable liquid-crystal materials the polymer compositions of which exhibit liquid-crystal phases.

It has now been found that the compounds of the formula I' are excellently suitable as precursors for the preparation of polymer compositions exhibiting liquid-crystal phases, and these compositions exhibit surprisingly broad mesophase ranges and a double refraction which can vary within wide limits. In addition, they can easily be processed to give articles of any shape having anisotropic properties and exhibiting a high stability to chemicals.

The invention relates to the compounds of the formula I' and to their use as polymerizable liquid-crystal materials.

The invention also relates to the use of the compounds of the formula I' for the preparation of polymer compositions, characterized in claim 1, which exhibit liquid-crystal phases.

In the following text, for the sake of simplicity, in the formula I' and its partial formulae, Cy is a 1,4-cyclohexylene group in which it is also possible for one or two non-adjacent CH₂ groups to be replaced by 0 and/or S atoms, and/or for a

|
—CH₂ group to be replaced by

|
N=C— and Phe is a 1,4-phenylene group in which it is also possible for one or more CH groups to be replaced by N.

In the following text, Cyc is the cyclohexylene group of the formula I'

R²—(A³—Z¹)ₘ—⟨Cyc⟩⟨Q¹ (axial) / R³⟩   I' to which Q¹ (in the axial position) and R³ are attached. Cy and Phe can be present in an unsubstituted form or substituted by halogen, CN and/or CH₃.

The compounds of the formula I' embrace compounds having two rings (partial formulae I'a to I'b), having three rings (I'c to I'f) and having four rings (I'g to I'n):

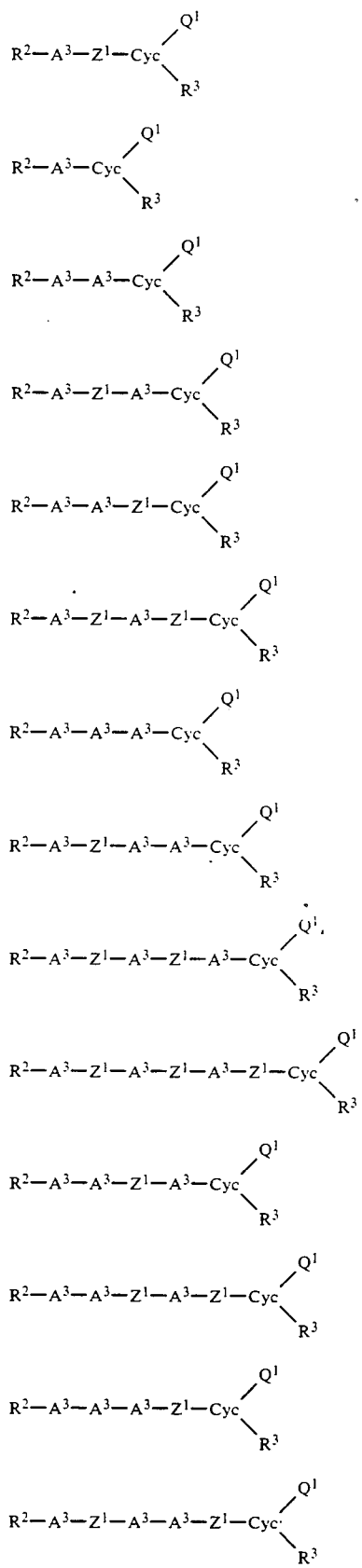

Amongst these the compounds of the formula I'a, I'b, I'c, I'd, I'e, I'f, I'g and I'h are particularly preferred;

compounds of the formulae I'a, I'b, I'c, I'e and I'f are especially preferred.

The preferred compounds of the formula I'a embrace those of the partial formulae I'aa to I'ad:

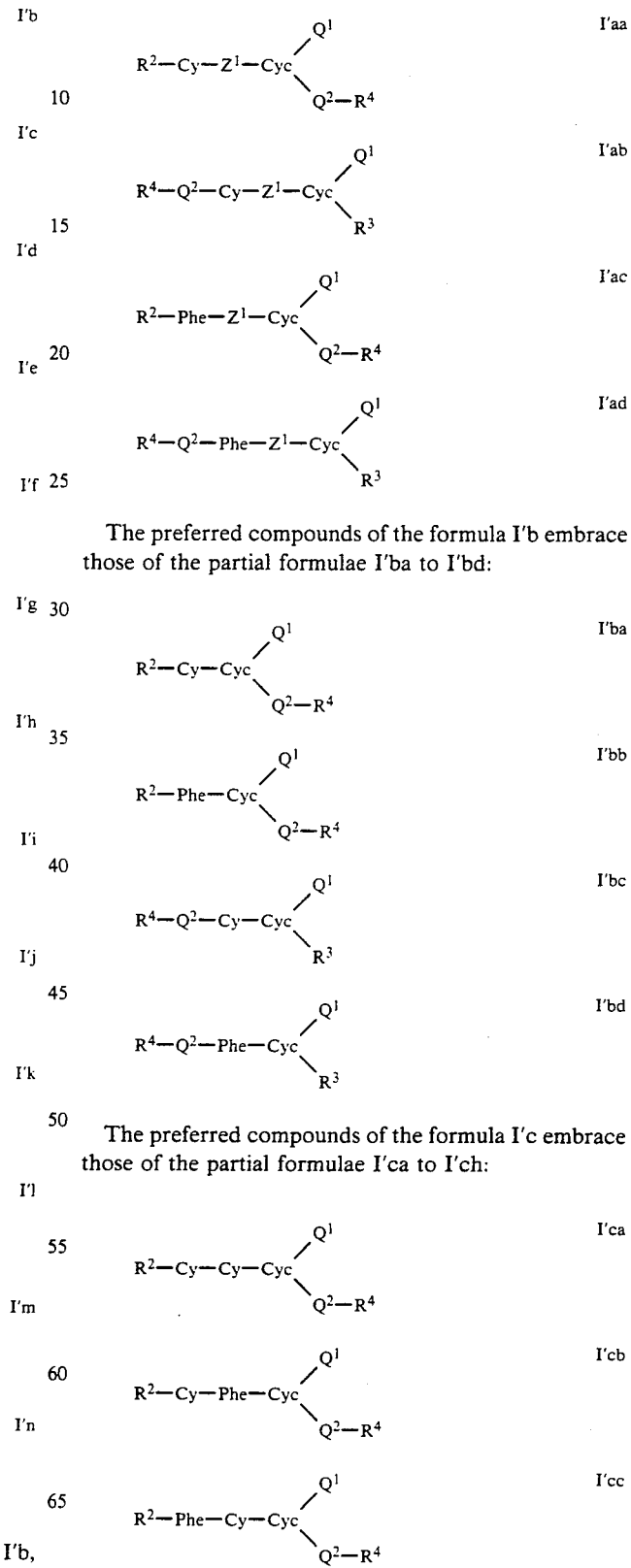

The preferred compounds of the formula I'b embrace those of the partial formulae I'ba to I'bd:

The preferred compounds of the formula I'c embrace those of the partial formulae I'ca to I'ch:

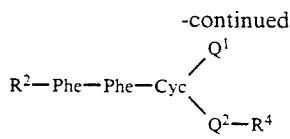  I'cd

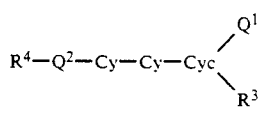  I'ce

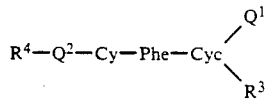  I'cf

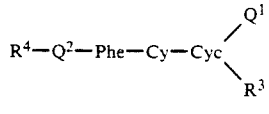  I'cg

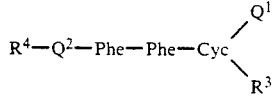  I'ch

The preferred compounds of the formula I'd embrace those of the partial formulae I'da to I'dh:

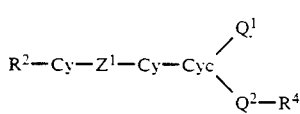  I'da

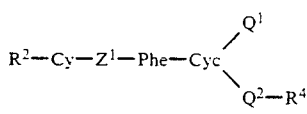  I'db

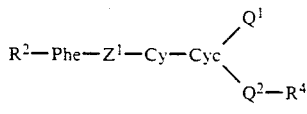  I'dc

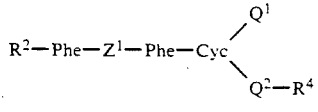  I'dd

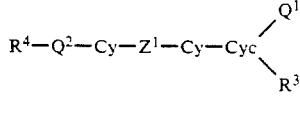  I'de

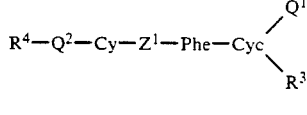  I'df

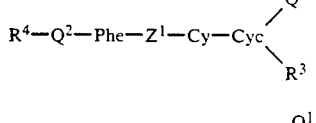  I'dg

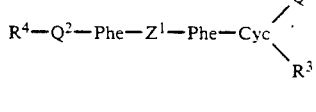  I'dh

The preferred compounds of the formula I'e embrace those of the partial formula I'ea to I'eh:

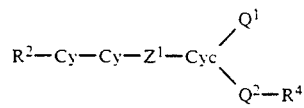  I'ea

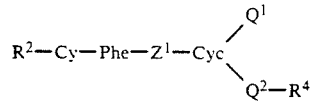  I'eb

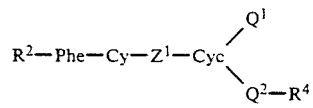  I'ec

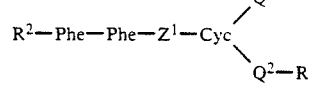  I'ed

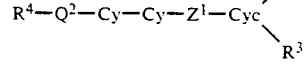  I'ee

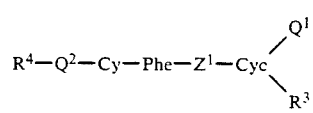  I'ef

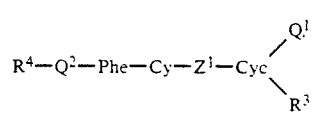  I'eg

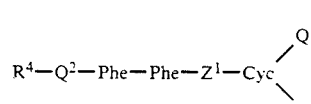  I'eh

Amongst these the compounds of the formulae I'ea, I'ed, I'ee and I'eh are particularly preferred.

The preferred compounds of the formula I'f embrace those of the partial formulae I'fa to I'fh:

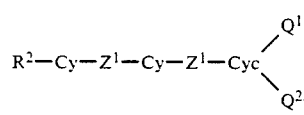  I'fa

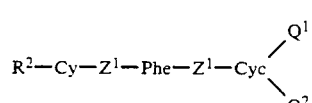  I'fb

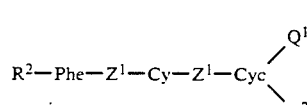  I'fc

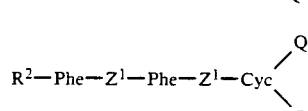  I'fd

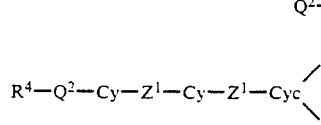  I'fe

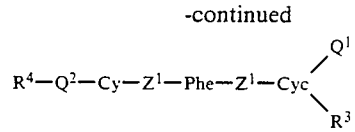 I'ff

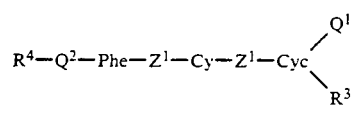 I'fg

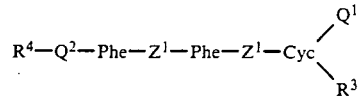 I'fh

The preferred compounds of the formula I'g embrace those of the partial formulae I'ga to I'gh:

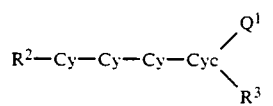 I'ga

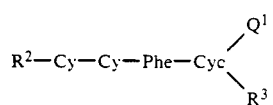 I'gb

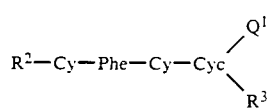 I'gc

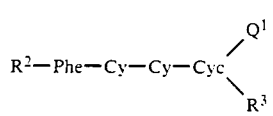 I'gd

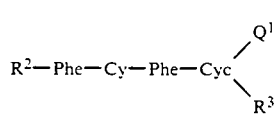 I'ge

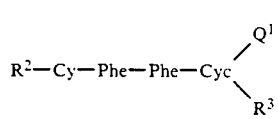 I'gf

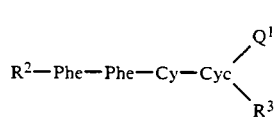 I'gg

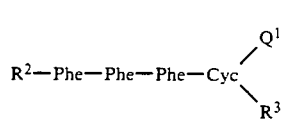 I'gh

The preferred compounds of the formula I'h embrace those of the partial formulae I'ha to I'hh:

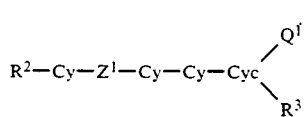 I'ha

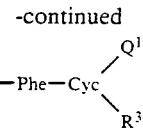 I'hb
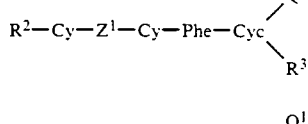

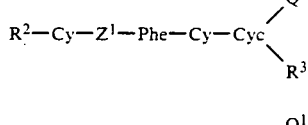 I'hc

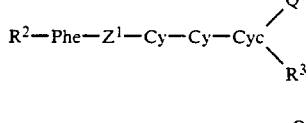 I'hd

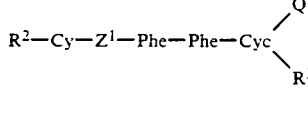 I'he

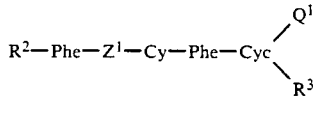 I'hf

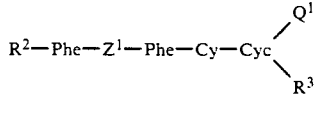 I'hg

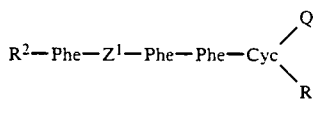 I'hh

The preferred compounds of the formula I'i embrace those of the partial formulae I'ia to I'ih:

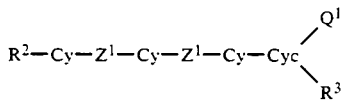 I'ia

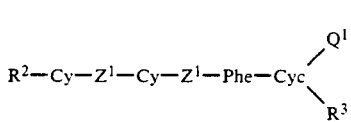 I'ib

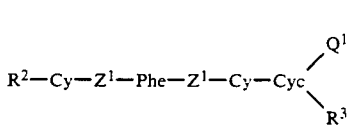 I'ic

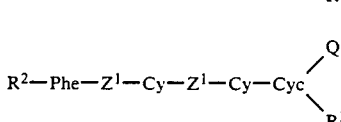 I'id

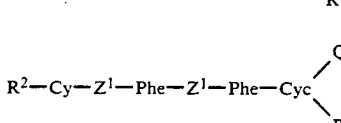 I'ie

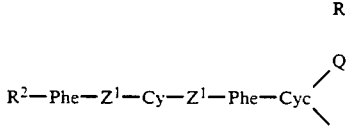 I'if

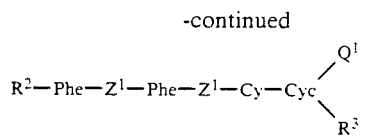 I'ig

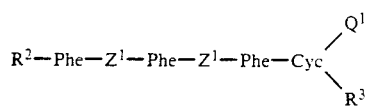 I'ih

The preferred compounds of the formula I'j embrace those of the partial formulae I'ja to I'jh:

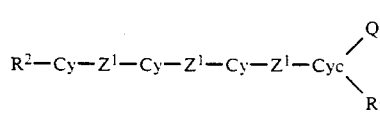 I'ja

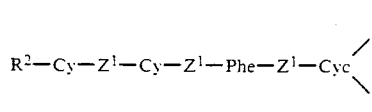 I'jb

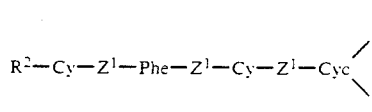 I'jc

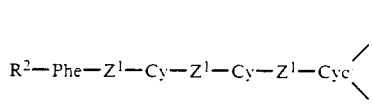 I'jd

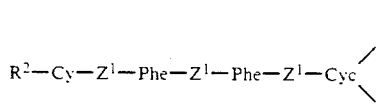 I'je

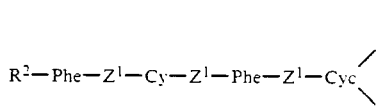 I'jf

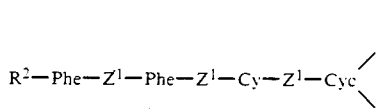 I'jg

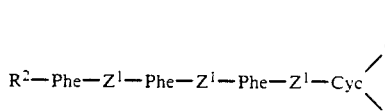 I'jh

The preferred compounds of the formula I'k embrace those of the partial formulae I'ka to I'kh:

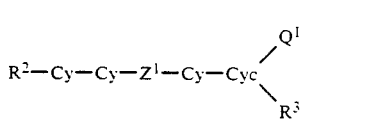 I'ka

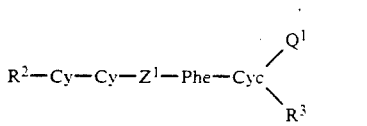 I'kb

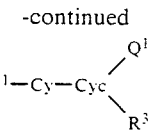 I'kc

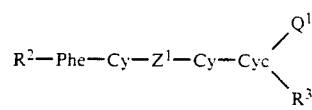 I'kd

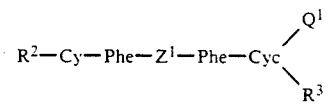 I'ke

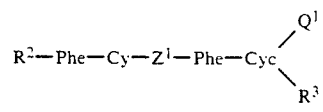 I'kf

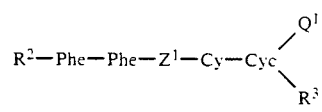 I'kg

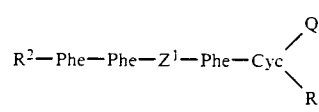 I'kh

The preferred compounds of the formula I'l embrace those of the partial formulae I'la to I'lh:

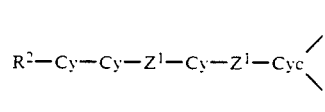 I'la

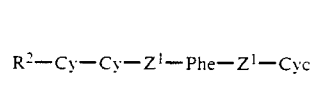 I'lb

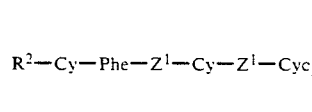 I'lc

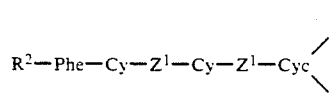 I'ld

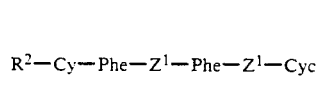 I'le

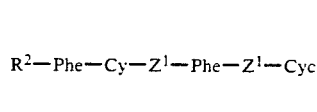 I'lf

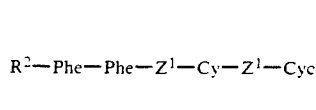 I'lg

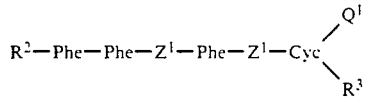 I'lh

The preferred compounds of the formula I'm embrace those of the partial formulae I'ma to I'mh:

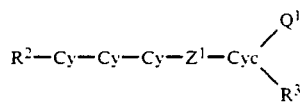 I'ma

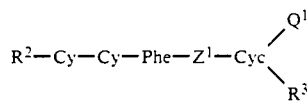 I'mb

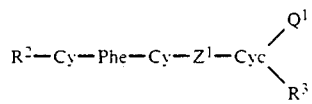 I'mc

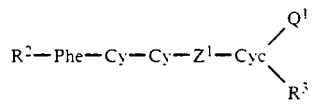 I'md

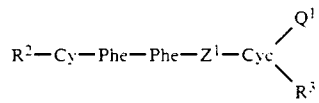 I'me

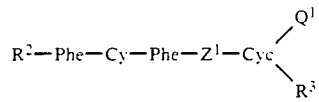 I'mf

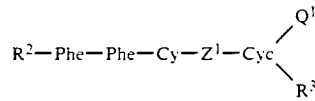 I'mg

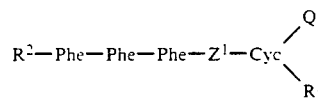 I'mh

The preferred compounds of the formula I'n embrace those of the partial formulae I'na to I'nh:

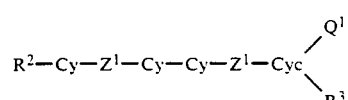 I'na

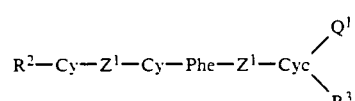 I'nb

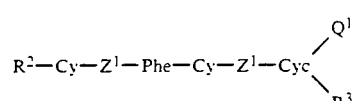 I'nc

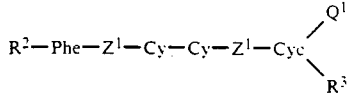 I'nd

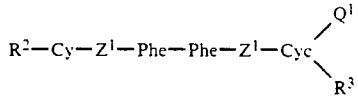 I'ne

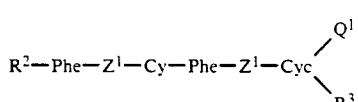 I'nf

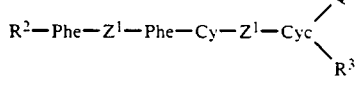 I'ng

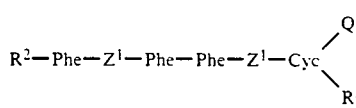 I'nh

In the preceding and following preferred partial formulae Cy is preferably unsubstituted or substituted 1,4-cyclohexylene, 1,3-dioxane-2,5-diyl, in particular 1,4-cyclohexylene, and Phe is preferably 1,4-phenylene, a pyridine-2,5-diyl group or a pyrimidine-2,5-diyl group, in particular 1,4-phenylene which is unsubstituted or substituted by halogen, CN and/or $CH_3$.

In the preceding and following formulae, $R^4$ (the same meanings apply to W in formula XII) is a vinyl, carboxyl, hydroxyl, amino, mercapto or epoxide group which is unsubstituted or substituted by 1, 2 or 3 F and/or Cl atoms and/or $CH_3$ groups, preferably a vinyl group which is unsubstituted or substituted by a $CH_3$ group, or a hydroxyl group.

$Q^2$ is alkylene having 3 to 18 C atoms, preferably 4 to 11 and particularly preferably 6 to 8 C atoms, and accordingly is preferably butylene, pentylene, hexylene, heptylene or octylene in which it is also possible for one or two non-adjacent $CH_2$ groups to be replaced, preferably by —O—, —CO—, —O—CO—, —CO—O— or —CRR'—T—.

The following groupings a)-k) are very particularly preferred for —$Q^2$—$R^4$—:
a) —$(CH_2)_{11}$—O—CO—C($CH_3$)=$CH_2$
b) —$(CH_2)_{11}$—OH
c) —$(CH_2)_9$—CH=$CH_2$
d) —O—$(CH_2)_6$—O—CO—C($CH_3$)=$CH_2$
e) —$(CH_2)_4$—CH=$CH_2$
f) —O—$(CH_2)_6$—OH
g) —O—$(CH_2)_{11}$—OH
h) —O—$(CH_2)_{11}$—O—CO—C($CH_3$)=$CH_2$
i) —$(CH_2)_4$—OH
j) —$(CH_2)_4$—O—CO—C($CH_3$)=$CH_2$
k) —$CH_2$—CH—O—$(CH_2)_9$—CH=$CH_2$ k)  —$CH_2$—$\underset{\underset{CH_3}{|}}{CH}$—O—$(CH_2)_9$—CH=$CH_2$ R' is halogen, i.e. fluorine, chlorine or bromine, or CN, preferably F, Cl or CN.

T is preferably —CO—O— or a single bond, and R is preferably H or methyl, and also ethyl, propyl, butyl, pentyl or hexyl.

Branched alkylene groups, preferably having 4 to 8 C atoms, are also preferred for $Q^2$, and these accordingly are preferably 1-methylpropylene, isobutylene, 2-methylbutylene, 3-methylbutylene, 2-methylpentylene or 2-methylhexylene. In these it is also possible once again for $CH_2$ groups to be replaced by the preferred groups indicated.

If $Q^1$ is CN, $Q^2$ is an alkylene or alkyleneoxy group and $R^4$ is an unsubstituted vinyl group, then $Q^2$ contains at least 4 C atoms and preferably has 6–10 C atoms.

$A^3$ preferably has a meaning mentioned for Cy or Phe.

$Z^1$ is preferably —CO—O—, —O—CO—, —CH$_2$—CH$_2$— or a single bond, and the group —CRR'—T— is also preferred, with R, R' and T having the preferred meanings indicated.

m is preferably 1 or 2.

$Q^1$ is preferably methyl, ethyl, propyl, methoxy, ethoxy, propoxy, F or CN, and also butyl, pentyl, butoxy, pentoxy, Cl or Br. The cyano group is very particularly preferred.

One of the radicals $R^2$ and $R^3$ has the meaning of —$Q^2$—$R^4$ in which $Q^2$ and $R^4$ have the preferred meanings indicated. The other radical in the preceding and following formulae I' is then preferably alkyl, alkoxy or oxaalkyl.

Compounds of the formula I' in which $R^2$ or $R^3$ is an alkyl group in which one or more $CH_2$ groups have been replaced, preferably by a —CO—, —CO—O—, —OCO—, —CRR'—T—, —C(halogen)$_2$— or —CH=CH'— group, are then also preferred. Halogen is preferably F or Cl. R, R' and T here have the preferred meanings indicated.

If $R^2$ or $R^3$ is an alkyl radical or an alkoxy radical, this radical can be linear or branched. It is preferably linear, has 2, 3, 4, 5, 6, 7 or 8 C atoms and, accordingly, is preferably ethyl, propyl, butyl, pentyl, hexyl, heptyl, octyl, ethoxy, propoxy, butoxy, pentoxy, hexyloxy, heptyloxy, or octyloxy, and also methyl, nonyl, decyl, undecyl, dodecyl, tridecyl, tetradecyl, pentadecyl, methoxy, nonyloxy, decyloxy, undecyloxy, dodecyloxy, tridecyloxy or tetradecyloxy.

Oxaalkyl is preferably linear 2-oxapropyl (=methoxymethyl), 2-oxabutyl (=ethoxymethyl), 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl.

If $R^2$ or $R^3$ is an alkyl radical in which a $CH_2$ group has been replaced by —CH=CH—, this radical can be linear or branched. It is preferably linear and has 2 to 10 C atoms. Accordingly, it is especially vinyl, prop-1-enyl, prop-2-enyl, but-1-, but-2- or but-3-enyl, pent-1-, pent-2-, pent-3- or pent-4-enyl, hex-1-, hex-2-, hex-3-, hex-4- or hex-5-enyl, hept-1-, hept-2-, hept-3-, hept-4-, hept-5- or hept-6-enyl, oct-1-, oct-2-, oct-3-, oct-4-, oct-5-, oct-6- or oct-7-enyl, non-1-, non-2-, non-3-, non-4-, non-5-, non-6-, non-7- or non-8-enyl or dec-1-, dec-2-, dec-3-, dec-4-, dec-5-, dec-6-, dec-7, dec-8- or dec-8-enyl.

Compounds of the formulae I' having a branched wing group $R^2$ or $R^3$ can occasionally be of interest as comonomers because they reduce the tendency to crystallization, but are particularly of interest as chiral constituents of polymers, if they are optically active. Cholesteric phases which can be used as thermochromic films, or polymers having tilted smectic phases are obtained in this way by means of these comonomers.

Branched groups of this type as a rule do not contain more than one chain branching. Preferred branched radicals $R^2$ or $R^3$ are isopropyl, 2-butyl (=1-methylpropyl), isobutyl (=2-methylpropyl), 2-methylbutyl, isopentyl, (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexyloxy, 1-methylhexyloxy, 2-octyloxy, 2-oxa-3-methylbutyl, 3-oxa-4-methylpentyl, 4-methylhexyl, 2-nonyl, 2-decyl, 2-dodecyl, 6-methyloctyloxy, 6-methyloctanoyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

The formula I' embraces not only the racemates of these compounds but also the optical antipodes and mixtures thereof.

Amongst the compounds of the formula I' and all the partial formulae thereof, preferred compounds are those in which at least one of the radicals contained therein has one of the preferred meanings indicated.

A minor group of particularly preferred compounds of the formula I' is formed by the following compounds of the formulae I'1 to I'15:

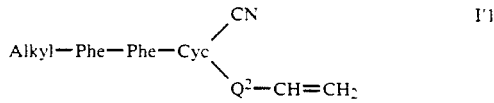

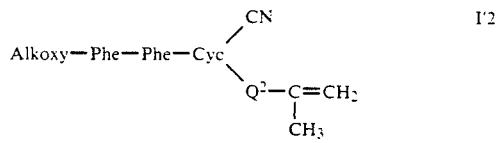

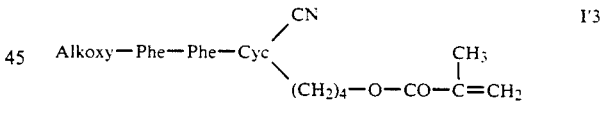

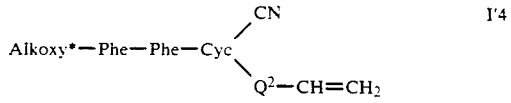

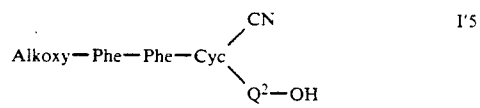

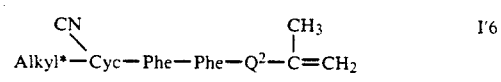

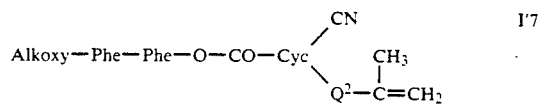

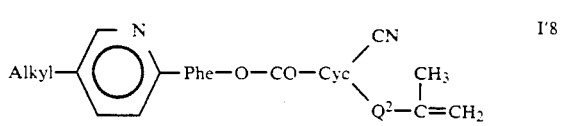

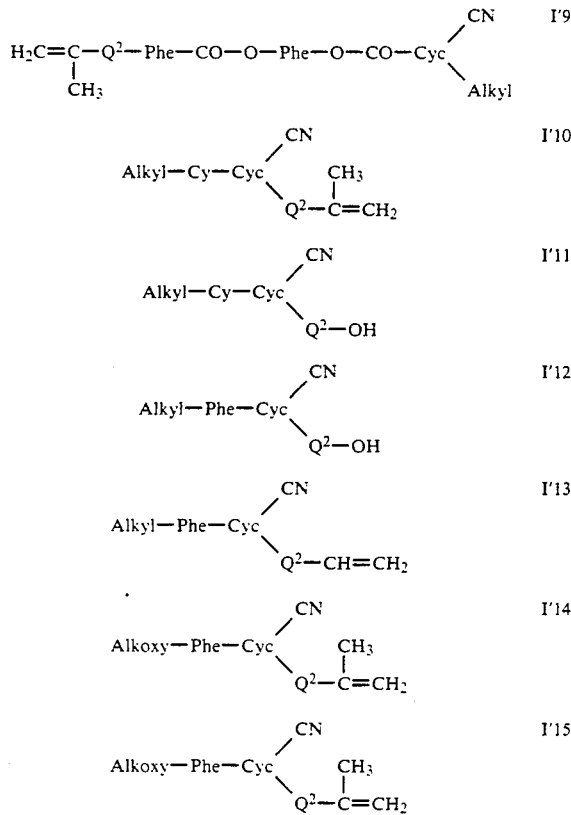

In these formulae alkyl* or alkoxy* is an optically active alkyl or alkoxy radical respectively.

The invention also relates to the use of the compounds of the formula I as precursors for the preparation of polymers which exhibit liquid-crystal phases, preferably polymer phases of the type characterized in claim 1.

The polymer materials according to the invention can also be prepared from the compounds of the formulae I' or XII by copolymerization with further olefinically unsaturated monomers. Examples of suitable comonomers are $C_1$-$C_{20}$-alkyl esters of acrylic and/or methacrylic acid, styrene, α-methylstyrene, 4-methylstyrene, acrylonitrile, methacrylonitrile and methylenemalonic esters.

If $R^4$ in formula I' or W in formula XII is a vinyl group, the polymerization is effected in the manner known per se by the action of radiant, heat or electrical energy and by the action of free-radical or ionic catalysts such as are described, for example, in Ocian, Principles of Polymerization, McGraw-Hill, New York, or the polymerization is effected as group transfer polymerization using silylketene acetals as the initiator and Lewis bases as a co-initiator (described, for example, by O. W. Webster et al., J. Am. Chem. Soc. 1983, 105, 5706-5708). UV, laser, X-ray and radioactive radiation is suitable for use as radiant energy. Electrical energy can be produced, for example, by electrolysis processes. Examples of free-radical catalysts are potassium persulfate, dibenzoyl peroxide, azobisisobutyronitrile, di-tert.-butyl peroxide and cyclohexanone peroxide. Ionic catalysts are organoalkali compounds, such as phenyllithium and naphthalenesodium, or Lewis acids, such as $BF_3$, $AlCl_3$, $SnCl_4$ and $TiCl_4$ or metal complexes in the form of aluminum or titanium compounds. The monomers can be polymerized in solution, suspension, emulsion or in bulk.

If $R^4$ or W is a hydroxyl, amino, mercapto, epoxide or carboxyl group or a reactive derivative thereof, the compounds of the formula I' or of the formula XII, respectively, can be either polymerized or polycondensed or can also be grafted onto a polymeric backbone.

In this respect $R^4$ or W are particularly preferably OH, $NH_2$, COOH or a reactive derivative, particularly OH or a reactive derivative of the carboxyl group. The grafting reaction can be carried out by methods known per se, such as, for example, esterification, amidation, transesterification, transamidation, acetylization or etherification, which are described in the literature [for example in standard works such as Houben-Weyl, Methoden der Org. Chemie ("Methods of organic chemistry"), Georg-Thieme-Verlag, Stuttgart, or C. M. Paleos et al., J. Polym. Sci. Polym. Chem. 19 (1981), 1427].

A preferred grafting reaction consists in reacting compounds of the formula I' or XII with organopolysiloxanes. This is effected, as is described, for example, in EP Patent Specification 0,060,335, by reacting linear or cyclic organo-hydrogen polysiloxanes with ethylenically unsaturated compounds of the formula I' or XII in approximately equimolar amounts, relative to the amount of siloxane hydrogen, in the presence of a catalyst which promotes the addition reaction between silane hydrogen and aliphatic multiple bonds.

Suitable polymeric backbones are, in principle, any polymers in which the chains exhibit a certain flexibility. These can be linear, branched or cyclic polymer chains. The degree of polymerization is normally at least 10, preferably 20-100. Oligomers, especially cyclic oligomers, having 3 to 15, especially 4 to 7, monomer units are also suitable, however.

It is preferable to employ polymers having C—C main chains, in particular polyacrylates, polymethacrylates, poly-α-halogenoacrylates, poly-α-cyanoacrylates, polyacrylamides, polyacrylonitriles or polymethylenemalonates. Preferred polymers are also those having heteroatoms in the main chain, for example polyethers, polyesters, polyamides, polyimides or polyurethanes or, in particular, polysiloxanes.

The polymer compositions, according to the invention, exhibiting liquid-crystal phases preferably contain 20-100% of mesogenic groups having a transversely polarizing structural element corresponding to the formulae I to X. A content of 50-100% is particularly preferred.

The compounds of the formula I' can be prepared by methods known per se, such as are described in the literature (for example in the standard works such as Houben-Weyl, Methoden der organischen Chemie ("Methods of organic chemistry"), Georg-Thieme-Verlag, Stuttgart), specifically under reaction conditions which are known and suitable for the reactions mentioned. In this regard it is also possible to make use of variants which are known per se but are not mentioned here in detail.

Thus compounds of the formula I' having the reactive groups $R^4$ can be obtained, for example in compounds which otherwise correspond to the formula I', by dehydrogenating an alkyl group to give the vinyl group, or reducing a carboxyl group to give the hydroxyl group, or converting a nitrile into the amino group. Epoxide groups are obtained by epoxidation of the corresponding cyclohexane derivatives using standard processes.

These preparative processes are known methods which are described in the literature (for example in standard works such as Houben-Weyl, Methoden der organischen Chemie ("Methods of organic chemistry"), Georg-Thieme-Verlag, Stuttgart), specifically under reaction conditions which are known and suitable for the reactions mentioned. In this regard it is also possible to make use of variants which are known per se but are not mentioned here in detail.

Compounds of the formula I' can, for example, be prepared by the following methods:

Compounds of the formula HX in which X is F, Cl, Br or CN can be added onto compounds of the formula II'

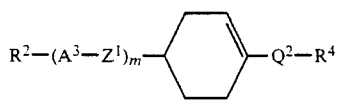

II' in which $R^2$, $A^3$, $Z^1$, m, $Q^2$ and $R^4$ have the meanings indicated. In this regard it is possible to make use of reaction conditions and variants which are known for addition reactions.

It is also possible to convert compounds which otherwise correspond to the formula I', but contain, instead of $R^4$, a saturated and/or non-reactive group into the compounds of the formula I' having a reactive group $R^4$ by oxidation, reduction or exchange reactions.

It is also possible to convert compounds of the formulae III' or IV'

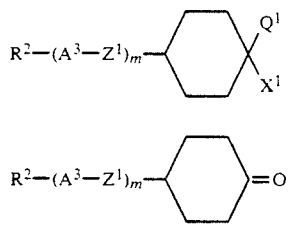

III'

IV' in which $R^2$, $A^3$, $Z^1$, m and $Q^1$ have the meanings indicated and $X^1$ is H or OH into compounds of the formula I' by reaction with reducing or alkylating agents, by reaction with alkyl halides or sulfonates and, if appropriate, subsequent oxidation, or by means of carboxylic acids or the reactive derivatives of carboxylic acids or carbonic acids.

If compounds of the formula I' in which $Q^1$ is OH are etherified by known methods, compounds of the formula I' in which $Q^1$ is alkoxy are obtained.

Nitriles of the formula I' in which $Q^1$ is CN are obtained by reacting compounds of the formula VI'

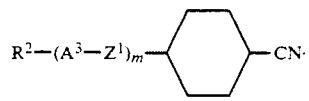

VI' with a compound of the formula VII'

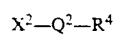

VII' in which $R^2$, $A^3$, $Z^1$, m, $Q^2$ and $R^4$ have the meanings indicated and X2 is Cl, Br, I, OH or a reactive esterified OH group.

This nitrile group can then be converted into the methyl group by reduction via the corresponding aldehyde.

The compounds of the formula I' can thus also be prepared by reducing a compound which otherwise corresponds to the formula I, but contains, instead of H atoms, one or more reducible groups and/or C—C bonds.

Suitable reducible groups are preferably —CH═CH— groups, and also, for example, free or esterified hydroxyl groups, halogen atoms attached to an aromatic nucleus or carbonyl groups. Preferred starting materials for the reduction correspond to the formula I', but can contain a —CH═CH— group instead of a —CH$_2$CH$_2$— group, and/or a —CO— group instead of a —CH$_2$— group, and/or a free or functionally modified (for example in the form of its p-toluenesulfonate) OH group instead of an H atom.

The reduction can be carried out, for example, by catalytic hydrogenation at temperatures between about 0° C. and about 200° and under pressures between about 1 and 200 bar, in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example PtO$_2$ or PdO), on a support (for example Pd on charcoal, calcium carbonate or strontium carbonate) or in a finely divided form.

Ketones can also be reduced by the method of Clemmensen (using zinc, amalgamated zinc or tin and hydrochloric acid, preferably in an aqueous alcoholic solution or in a heterogeneous phase with water/toluene at temperatures between about 80° and 120°) or Wolff-Kishner (using hydrazine, preferably in the presence of an alkali, such as KOH or NaOH, in a high-boiling solvent, such as diethylene glycol or triethylene glycol, at temperatures between about 100° and 200°) to give the corresponding compounds of the formula I' containing alkyl groups and/or —CH$_2$CH$_2$— bridges.

Reductions by means of complex hydrides are also possible. For example, arylsulfonyloxy groups can be removed reductively using LiAlH$_4$, in particular p-toluenesulfonyloxymethyl groups can be reduced to methyl groups, preferably in an inert solvent, such as diethyl ether or THF, at temperatures between about 0° and 100°. Double bonds can be hydrogenated (even in the presence of CN groups!) by means of NaBH$_4$ or tributyltin hydride in methanol.

Esters of the formula I' can also be obtained by esterifying corresponding carboxylic acids (or reactive derivatives thereof) with alcohols or phenols (or reactive derivatives thereof).

Suitable reactive derivatives of the carboxylic acids mentioned are, in particular, the acid halides, above all the chlorides and bromides, and also the anhydrides, for example also mixed anhydrides, azides or esters, in particular alkyl esters having 1–4 C atoms in the alkyl group. Suitable reactive derivatives of the alcohols or phenols mentioned are, in particular, the corresponding metal alcoholates or phenates, respectively, preferably of an alkali metal, such as Na or K.

The esterification is advantageously carried out in the presence of an inert solvent. Solvents which are very suitable are, in particular, ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenated hydrocarbons, such as carbon tetrachloride or tetrachloroethylene, and sulfoxides, such as dimethyl sulfoxide, or sulfolane. Water-immiscible solvents can, at the same time, advantageously be used for the removal by azeotropic distillation of the water formed in the esterification. Occasionally, an excess of an organic base, for example pyridine, quinoline or triethylamine, can also be used as the solvent for the esterification. The esterification can also be carried out in the absence of a solvent, for example merely by heating the components in the presence of sodium acetate. The reaction temperature is usually between −50° and +250°, preferably between −20° and 80°. At these temperatures the esterifications are, as a rule, complete after 15 minutes to 48 hours.

In an individual case, the reaction conditions for the esterification depend largely on the nature of the starting materials used. Thus a free carboxylic acid will, as a rule, be reacted with a free alcohol or phenol in the presence of a strong acid, for example a mineral acid, such as hydrochloric acid or sulfuric acid. Esterification in the presence of dicyclohexylcarbodiimide, if necessary with the addition of a base, such as, for example, 4-dimethylaminopyridine, is also possible. A preferred mode of reaction is the reaction of an acid anhydride or, in particular, an acid chloride with an alcohol, preferably in a basic medium, the bases of importance being, in particular, alkali metal hydroxides, such as sodium hydroxide or potassium hydroxide, alkali metal carbonates or bicarbonates, such as sodium carbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification consists in first converting the alcohol or the phenol into the sodium or potassium alcoholate or phenate, respectively, for example by treatment with ethanolic sodium hydroxide or potassium hydroxide solution, isolating this product and suspending it, together with sodium bicarbonate or potassium carbonate, in acetone or diethyl ether by stirring, and adding a solution of the acid chloride or anhydride in diethyl ether, acetone or DMF to this suspension, preferably at temperatures between about −25° and +20°.

Dioxane derivatives or dithiane derivatives of the formula I' are preferably prepared by reacting a corresponding aldehyde (or a reactive derivative thereof) with a corresponding 1,3-diol or a corresponding 1,3-dithiol, respectively, (or a reactive derivative thereof) preferably in the presence of an inert solvent, such as benzene or toluene, and/or a catalyst, for example a strong acid, such as sulfuric acid, benzenesulfonic acid or p-toluenesulfonic acid, at temperatures between 20° and about 150°, preferably between 80° and 120°. Suitable reactive derivatives of the starting materials are primarily acetals.

The aldehydes and 1,3-diols or 1,3-dithiols mentioned, and also their reactive derivatives, are in part known; they can all be prepared without difficulty from compounds known from the literature by standard processes of organic chemistry. For example, the aldehydes are accessible by oxidizing corresponding alcohols or by reducing corresponding carboxylic acids or derivatives thereof, the diols are accessible by reducing corresponding diesters, and the dithiols are accessible by reacting corresponding dihalides with NaSH.

Nitriles of the formula I' can be prepared by dehydrating corresponding acid amides, for example those in which there is a $CONH_2$ group instead of the radical X. The amides are accessible, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2Cl_2$, $COCl_2$, and also $P_2O_5$, $P_2S_5$, $AlCl_3$ (for example in the form of double compounds with NaCl), aromatic sulfonic acids and sulfonyl halides. The reaction can be carried out in the presence or absence of an inert solvent at temperatures between about 0° and 150°; examples of suitable solvents are bases, such as pyridine or triethylamine, aromatic hydrocarbons, such as benzene, toluene or xylene, or amides, such as DMF.

The abovementioned nitriles of the formula I can also be prepared by reacting corresponding acid halides, preferably the chlorides, with sulfamide, preferably in an inert solvent, such as tetramethylene sulfone, at temperatures between about 80° and 150°, preferably at 120°. After being worked up in a customary manner the nitriles can be isolated without further treatment.

Ethers of the formula I' are accessible by etherifying corresponding hydroxy compounds, preferably corresponding phenols, it being preferable first to convert the hydroxy compounds into a corresponding metal derivative, for example into the corresponding alkali metal alcoholate or alkali metal phenate by treatment with NaH, $NaNH_2$, NaOH, KOH, $Na_2CO_3$ or $K_2CO_3$. This alcoholate or phenate can then be reacted with the corresponding alkyl halide, alkyl sulfonate or dialkyl sulfate, preferably in an inert solvent, such as acetone, 1,2-dimethoxyethane, DMF or dimethyl sulfoxide or an excess of aqueous or aqueous alcoholic NaOH or KOH, at temperatures between about 20° and 100°.

Cyclohexanone derivatives of the formula I' are also accessible by acid-catalyzed rearrangements of the corresponding epoxides by processes known from the literature, for example by treatment with $BF_3$ etherate. The epoxides are accessible by epoxidation of the corresponding cyclohexane derivatives by standard processes.

Nitriles of formula I' can also be prepared by reacting corresponding chlorine or bromine compounds of the formula I' with a cyanide, preferably a metal cyanide, such as NaCN, KCN or $Cu_2(CN)_2$, for example in the presence of pyridine in an inert solvent, such as DMF or N-methylpyrrolidone, at temperatures between 20° and 200°.

Compounds of the formula XII having appropriate terminal functional groups, and also the corresponding monomers of the formula XI, which, instead of the polymer, have a functional group located on the spacer and correspond to the formula XI'

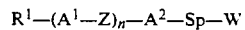     XI' in which $R^1$, $A^1$, Z, n, $A^2$, Sp and W have the meanings given, can be prepared analogously to the process discussed for the compounds of the formula I'. They can, therefore, also be prepared by methods known per se, such as are described in the literature (for example in the standard works, such as Houben-Weyl, Methoden der Organischen Chemie ("Methods of organic chemistry"), Georg-Thieme-Verlag, Stuttgart), specifically under reaction conditions which are known and suitable for the reactions mentioned. In this regard it is possible to make use of variants which are known per se but are not mentioned here in detail.

The low-molecular compounds of the formula I' or XII exhibit in some cases broad mesophase ranges. Compounds of the formula I' or XII which do not exhibit mesophases are, however, also suitable for the preparation of the polymer materials according to the invention.

The preparation of homopolymers or copolymers from the polymerizable compounds of the formula I', XI' or XII or polymerizable derivatives thereof is preferably carried out by free-radical polymerization. The reaction is initiated, for example, by UV irradiation or by free radical-formers. The monomers can be polymerized in solution or in bulk.

Copolymer materials, according to the invention, exhibiting liquid-crystal phases are obtained by copolymerizing polymerizable compounds of the formula I', XI' or XII or polymerizable derivatives thereof with monomers which do not carry mesogenic radicals, which carry other mesogenic radicals, which carry chiral radicals or which carry dyestuff radicals (German Offenlegungsschrift 3,211,400).

The copolymerization with monomers of this type, starting from a monomer mixture of concentration $X_1$, only results in a copolymer having an incorporation ratio corresponding to the monomer concentration $X_1$ if the copolymerization parameters of the monomer components are of a comparable order of magnitude. This is particularly important if a copolymer of a specific composition is to be prepared without problems, for example without taking account of the reaction kinetics. It is therefore preferable to select monomer components which have comparable copolymerization parameters, for instance alkyl acrylates or methacrylates which differ primarily in the substituents in the alkyl chain.

Copolymerization with monomers carrying no mesogenic radical results in general in a reduction in the glass temperature and in the clear point. It is often possible, by suitable selection of the spacer, to bring the mesophase range into the temperature range suitable for the particular end use.

Monomers having a chiral radical which can be used are, in principle, any compounds of this type which have asymmetric C atoms. In this respect, the asymmetric C atom can be located either in the wing group, between two rings or in the spacer group of the mesogenic radical.

Finally, numerous further possible variants arise because of the circumstance that the compounds according to the invention combine liquid-crystal properties with typical polymer properties, such as the capacity for forming layers, films and fibers, readiness of shaping and the like. These properties can be modified in a manner known per se by copolymerization or mixing with further components, by varying the molecular weight, by the addition of a very wide variety of inorganic or organic additives and metals, by crosslinking, for example to give an elastomer, and by many other treatments with which the polymer expert is familiar.

The polymer materials according to the invention can be used as starting material for the preparation of organic glasses having anisotropic properties which can be modified within wide ranges.

Applications of this type arise, for example, in the field of collecting devices for light and sunlight or in organic phototropic glasses. An important field of use also presents itself in the field of optical storage devices.

Further possible uses present themselves in the field of magnetic storage devices. In particular the materials according to the invention are themselves suitable as materials having non-linear optical properties or as a matrix for substances having non-linear optical properties for the production of non-linear optical structural elements.

The following examples serve to illustrate the invention, K indicating crystalline state, S indicating smectic phase (the index denotes the type of phase), N indicating nematic state, Ch indicating cholesteric phase and I indicating isotropic phase. The number standing between two symbols indicates the conversion temperature in degrees centigrade. M.p. denotes melting point and c.p. denotes clear point; G is glass-like state.

EXAMPLE 1

A solution of lithium diisopropylamine (prepared from 50 ml of THF, 13.2 g of diisopropylamine and 75 ml of 1.6M butyllithium solution in hexane) is added, at $-78°$ and under $N_2$, to a mixture of 13.1 g of trans,-trans,-4'-pentylbicyclohexyl-4-carbonitrile, 8.8 g of 3-bromopropanol and 75 ml of THF, and the mixture is stirred for 1 hour.

The mixture is warmed slowly to room temperature, water is added and the organic phase is worked up. 1-γ-hydroxypropyl-c-4-(trans-4-pentylcyclohexyl)-cyclohexane-1-r-carbonitrile of c.p. 63°, $S_A$ 110° I, is obtained by chromatography over silica gel and recrystallization from ethanol.

The following are prepared analogously from the corresponding starting compounds:
1-γ-hydroxypropyl-c-4-(trans-4-propylcyclohexyl)-cyclohexane-1-r-carbonitrile
1-γ-hydroxypropyl-c-4-(trans-4-butylcyclohexyl)-cyclohexane-1-r-carbonitrile
1-γ-hydroxypropyl-c-4-(trans-4-hexylcyclohexyl)-cyclohexane-1-r-carbonitrile
1-γ-hydroxypropyl-c-4-(trans-4-heptylcyclohexyl)-cyclohexane-1-r-carbonitrile
1-γ-hydroxypropyl-c-4-(trans-4-octylcyclohexyl)-cyclohexane-1-r-carbonitrile
1-γ-hydroxypropyl-c-4-(trans-4-nonylcyclohexyl)-cyclohexane-1-r-carbonitrile
1-δ-hydroxybutyl-c-4-(trans-4-propylcyclohexyl)-cyclohexane-1-r-carbonitrile
1-δ-hydroxybutyl-c-4-(trans-4-butylcyclohexyl)-cyclohexane-1-r-carbonitrile
1-δ-hydroxybutyl-c-4-(trans-4-pentylcyclohexyl)-cyclohexane-1-r-carbonitrile
1-δ-hydroxybutyl-c-4-(trans-4-hexylcyclohexyl)-cyclohexane-1-r-carbonitrile
1-δ-hydroxybutyl-c-4-(trans-4-heptylcyclohexyl)-cyclohexane-1-r-carbonitrile
1-δ-hydroxybutyl-c-4-(trans-4-octylcyclohexyl)-cyclohexane-1-r-carbonitrile
1-δ-hydroxybutyl-c-4-(trans-4-nonylcyclohexyl)-cyclohexane-1-r-carbonitrile
1-ε-hydroxypentyl-c-4-(trans-4-propylcyclohexyl)-cyclohexane-1-r-carbonitrile 1-ε-hydroxypentyl-c-4-(trans-4-butylcyclohexyl)-cyclohexane-1-r-carbonitrile
1-ε-hydroxypentyl-c-4-(trans-4-pentylcyclohexyl)-cyclohexane-1-r-carbonitrile
1-ε-hydroxypentyl-c-4-(trans-4-hexylcyclohexyl)-cyclohexane-1-r-carbonitrile
1-ε-hydroxypentyl-c-4-(trans-4-heptylcyclohexyl)-cyclohexane-1-r-carbonitrile
1-ε-hydroxypentyl-c-4-(trans-4-octylcyclohexyl)-cyclohexane-1-r-carbonitrile
1-ε-hydroxypentyl-c-4-(trans-4-nonylcyclohexyl)-cyclohexane-1-r-carbonitrile
1-γ-hydroxypropyl-c-4-(4-propylphenyl)-cyclohexane-1-r-carbonitrile
1-γ-hydroxypropyl-c-4-(4-butylphenyl)-cyclohexane-1-r-carbonitrile
1-γ-hydroxypropyl-c-4-(4-pentylphenyl)-cyclohexane-1-r-carbonitrile
1-γ-hydroxypropyl-c-4-(4-hexylphenyl)-cyclohexane-1-r-carbonitrile
1-γ-hydroxypropyl-c-4-(4-heptylphenyl)-cyclohexane-1-r-carbonitrile
1-γ-hydroxypropyl-c-4-(4-octylphenyl)-cyclohexane-1-r-carbonitrile
1-γ-hydroxypropyl-c-4-(4-nonylphenyl)-cyclohexane-1-r-carbonitrile
1-γ-hydroxypropyl-c-4-(4-decylphenyl)-cyclohexane-1-r-carbonitrile
1-γ-hydroxypropyl-c-4-(4-ethoxyphenyl)-cyclohexane-1-r-carbonitrile
1-γ-hydroxypropyl-c-4-(4-propoxyphenyl)-cyclohexane-1-r-carbonitrile
1-γ-hydroxypropyl-c-4-(4-butoxyphenyl)-cyclohexane-1-r-carbonitrile
1-γ-hydroxypropyl-c-4-(4-pentoxyphenyl)-cyclohexane-1-r-carbonitrile
1-γ-hydroxypropyl-c-4-(4-hexyloxyphenyl)-cyclohexane-1-r-carbonitrile
1-δ-hydroxybutyl-c-4-(4-propylphenyl)-cyclohexane-1-r-carbonitrile
1-δ-hydroxybutyl-c-4-(4-butylphenyl)-cyclohexane-1-r-carbonitrile
1-δ-hydroxybutyl-c-4-(4-pentylphenyl)-cyclohexane-1-r-carbonitrile
1-δ-hydroxybutyl-c-4-(4-hexylphenyl)-cyclohexane-1-r-carbonitrile
1-δ-hydroxybutyl-c-4-(4-heptylphenyl)-cyclohexane-1-r-carbonitrile
1-δ-hydroxybutyl-c-4-(4-octylphenyl)-cyclohexane-1-r-carbonitrile
1-δ-hydroxybutyl-c-4-(4-nonylphenyl)-cyclohexane-1-r-carbonitrile
1-δ-hydroxybutyl-c-4-(4-decylphenyl)-cyclohexane-1-r-carbonitrile
1-δ-hydroxybutyl-c-4-(4-ethoxyphenyl)-cyclohexane-1-r-carbonitrile
1-δ-hydroxybutyl-c-4-(4-propoxyphenyl)-cyclohexane-1-r-carbonitrile
1-δ-hydroxybutyl-c-4-(4-butoxyphenyl)-cyclohexane-1-r-carbonitrile
1-δ-hydroxybutyl-c-4-(4-pentoxyphenyl)-cyclohexane-1-r-carbonitrile
1-δ-hydroxybutyl-c-4-(4-hexyloxyphenyl)-cyclohexane-1-r-carbonitrile
1-ε-hydroxypentyl-c-4-(4-propylphenyl)-cyclohexane-1-r-carbonitrile
1-ε-hydroxypentyl-c-4-(4-butylphenyl)-cyclohexane-1-r-carbonitrile
1-ε-hydroxypentyl-c-4-(4-pentylphenyl)-cyclohexane-1-r-carbonitrile
1-ε-hydroxypentyl-c-4-(4-hexylphenyl)-cyclohexane-1-r-carbonitrile
1-ε-hydroxypentyl-c-4-(4-heptylphenyl)-cyclohexane-1-r-carbonitrile
1-ε-hydroxypentyl-c-4-(4-octylphenyl)-cyclohexane-1-r-carbonitrile
1-ε-hydroxypentyl-c-4-(4-nonylphenyl)-cyclohexane-1-r-carbonitrile
1-ε-hydroxypentyl-c-4-(4-decylphenyl)-cyclohexane-1-r-carbonitrile
1-ε-hydroxypentyl-c-4-(4-ethoxyphenyl)-cyclohexane-1-r-carbonitrile
1-ε-hydroxypentyl-c-4-(4-propoxyphenyl)-cyclohexane-1-r-carbonitrile
1-ε-hydroxypentyl-c-4-(4-butoxyphenyl)-cyclohexane-1-r-carbonitrile
1-ε-hydroxypentyl-c-4-(4-pentoxyphenyl)-cyclohexane-1-r-carbonitrile
1-ε-hydroxypentyl-c-4-(4-hexyloxyphenyl)-cyclohexane-1-r-carbonitrile

EXAMPLE 2

16.g g of 1-γ-cyanopropyl-4-c-(4-trans-pentylcyclohexyl)-cyclohexane-1-r-carbonitrile (described in German Offenlegungsschrift 3,320,024) are heated under reflux for 16 hours together with 10 g of KOH, 20 m (sic) of water and 40 ml of ethanol. The solution is cooled and neutralized, and the precipitate is filtered off with suction. Recrystallization from ethanol gives 3-[1-r-cyano-4-c-(4-trans-pentylcyclohexyl)-cyclohexyl]-butyric acid, m.p. 154°.

The following are prepared analogously:
3-[1-r-cyano-4-c-(4-trans-propylcyclohexyl)-cyclohexyl]-butyric acid
3-[1-r-cyano-4-c-(4-trans-butylcyclohexyl)-cyclohexyl]-butyric acid
3-[1-r-cyano-4-c-(4-trans-hexylcyclohexyl)-cyclohexyl]-butyric acid
3-[1-r-cyano-4-c-(4-trans-heptylcyclohexyl)-cyclohexyl]-butyric acid
3-[1-r-cyano-4-c-(4-trans-octylcyclohexyl)-cyclohexyl]-butyric acid
3-[1-r-cyano-4-c-(4-trans-nonylcyclohexyl)-cyclohexyl]-butyric acid
4-[1-r-cyano-4-c-(4-trans-propylcyclohexyl)-cyclohexyl]-valeric acid
4-[1-r-cyano-4-c-(4-trans-butylcyclohexyl)-cyclohexyl]-valeric acid
4-[1-r-cyano-4-c-(4-trans-pentylcyclohexyl)-cyclohexyl]-valeric acid
4-[1-r-cyano-4-c-(4-trans-hexylcyclohexyl)-cyclohexyl]-valeric acid
4-[1-r-cyano-4-c-(4-trans-heptylcyclohexyl)-cyclohexyl]-valeric acid
4-[1-r-cyano-4-c-(4-trans-octylcyclohexyl)-cyclohexyl]-valeric acid
4-[1-r-cyano-4-c-(4-trans-nonylcyclohexyl)-cyclohexyl]-valeric acid
5-[1-r-cyano-4-c-(4-trans-propylcyclohexyl)-cyclohexyl]-caproic acid
5-[1-r-cyano-4-c-(4-trans-butylcyclohexyl)-cyclohexyl]-caproic acid
5-[1-r-cyano-4-c-(4-trans-pentylcyclohexyl)-cyclohexyl]-caproic acid
5-[1-r-cyano-4-c-(4-trans-hexylcyclohexyl)-cyclohexyl]-caproic acid 5-[1-r-cyano-4-c-(4-trans-heptylcyclohexyl)-cyclohex-
  yl]-caproic acid
4-[1-r-cyano-4-c-(4-trans-octylcyclohexyl)-cyclohexyl]-
  caproic acid
5-[1-r-cyano-4-c-(4-trans-nonylcyclohexyl)-cyclohex-
  yl]-caproic acid.

EXAMPLE 3

6.3 mL a 1M solution of $BH_3$ . THF in THF are added at 0° to a solution in 10 mL of THF of 5 g of r-1-(3-butenyl)-t-4-(r-4-pentyl-t-1-cyclohexyl)-cyclohexyl-c-1-carbonitrile (which can be prepared from t-4-(r-4-pentyl-t-1-cyclohexyl)-cyclohexyl-r-1-carbonitrile and 1-bromo-3-butene in the presence of diisopropylamine and n-butyllithium in THF), and the mixture is stirred for a further hour.

1.6 ml of $H_2O$, 2.1 ml of 3M NaOH and 2.1 ml of 30% $H_2O_2$ are then added, and the mixture is stirred for 1 hour at room temperature.

Ether is added to the mixture and it is extracted with water. The organic phase is worked up and the residue is chromatographed over a silica gel column using 85:15 $CH_2Cl_2$/ethyl acetate. This gives r-1-(4-hydroxybutyl)-t-4-(r-4-pentyl-t-1-cyclohexyl)-cyclohexyl-c-1-carbonitrile of $S_A$ 100° I.

The following are prepared analogously:
r-1-(4-hydroxybutyl)-t-4-(r-4-ethyl-t-1-cyclohexyl)-
  cyclohexyl-c-1-carbonitrile
r-1-(4-hydroxybutyl)-t-4-(r-4-propyl-t-1-cyclohexyl)-
  cyclohexyl-c-1-carbonitrile
r-1-(4-hydroxybutyl)-t-4-(r-4-butyl-t-1-cyclohexyl)-
  cyclohexyl-c-1-carbonitrile
r-1-(4-hydroxybutyl)-t-4-(r-4-hexyl-t-1-cyclohexyl)-
  cyclohexyl-c-1-carbonitrile
r-1-(4-hydroxybutyl)-t-4-(r-4-heptyl-t-1-cyclohexyl)-
  cyclohexyl-c-1-carbonitrile
r-1-(4-hydroxybutyl)-t-4-(r-4-octyl-t-1-cyclohexyl)-
  cyclohexyl-c-1-carbonitrile .
r-1-(5-hydroxypentyl)-t-4-(r-4-ethyl-t-1-cyclohexyl)-
  cyclohexyl-c-1-carbonitrile
r-1-(5-hydroxypentyl)-t-4-(r-4-propyl-t-1-cyclohexyl)-
  cyclohexyl-c-1-carbonitrile
r-1-(5-hydroxypentyl)-t-4-(r-4-butyl-t-1-cyclohexyl)-
  cyclohexyl-c-1-carbonitrile
r-1-(5-hydroxypentyl)-t-4-(r-4-pentyl-t-1-cyclohexyl)-
  cyclohexyl-c-1-carbonitrile
r-1-(5-hydroxypentyl)-t-4-(r-4-hexyl-t-1-cyclohexyl)-
  cyclohexyl-c-1-carbonitrile
r-1-(5-hydroxypentyl)-t-4-(r-4-heptyl-t-1-cyclohexyl)-
  cyclohexyl-c-1-carbonitrile
r-1-(5-hydroxypentyl)-t-4-(r-4-octyl-t-1-cyclohexyl)-
  cyclohexyl-c-1-carbonitrile
r-1-(6-hydroxyhexyl)-t-4-(r-4-ethyl-t-1-cyclohexyl)-
  cyclohexyl-c-1-carbonitrile
r-1-(6-hydroxyhexyl)-t-4-(r-4-propyl-t-1-cyclohexyl)-
  cyclohexyl-c-1-carbonitrile
r-1-(6-hydroxyhexyl)-t-4-(r-4-butyl-t-1-cyclohexyl)-
  cyclohexyl-c-1-carbonitrile
r-1-(6-hydroxyhexyl)-t-4-(r-4-pentyl-t-1-cyclohexyl)-
  cyclohexyl-c-1-carbonitrile
r-1-(6-hydroxyhexyl)-t-4-(r-4-hexyl-t-1-cyclohexyl)-
  cyclohexyl-c-1-carbonitrile
r-1-(6-hydroxyhexyl)-t-4-(r-4-heptyl-t-1-cyclohexyl)-
  cyclohexyl-c-1-carbonitrile
r-1-(6-hydroxyhexyl)-t-4-(r-4-octyl-t-1-cyclohexyl)-
  cyclohexyl-c-1-carbonitrile
r-1-(7-hydroxyheptyl)-t-4-(r-4-ethyl-t-1-cyclohexyl)-
  cyclohexyl-c-1-carbonitrile
r-1-(7-hydroxyheptyl)-t-4-(r-4-propyl-t-1-cyclohexyl)-
  cyclohexyl-c-1-carbonitrile
r-1-(7-hydroxyheptyl)-t-4-(r-4-butyl-t-1-cyclohexyl)-
  cyclohexyl-c-1-carbonitrile
r-1-(7-hydroxyheptyl)-t-4-(r-4-pentyl-t-1-cyclohexyl)-
  cyclohexyl-c-1-carbonitrile
r-1-(7-hydroxyheptyl)-t-4-(r-4-hexyl-t-1-cyclohexyl)-
  cyclohexyl-c-1-carbonitrile
r-1-(7-hydroxyheptyl)-t-4-(r-4-heptyl-t-1-cyclohexyl)-
  cyclohexyl-c-1-carbonitrile
r-1-(7-hydroxyheptyl)-t-4-(r-4-octyl-t-1-cyclohexyl)-
  cyclohexyl-c-1-carbonitrile
r-1-(8-hydroxyoctyl)-t-4-(r-4-ethyl-t-1-cyclohexyl)-
  cyclohexyl-c-1-carbonitrile
r-1-(8-hydroxyoctyl)-t-4-(r-4-propyl-t-1-cyclohexyl)-
  cyclohexyl-c-1-carbonitrile
r-1-(8-hydroxyoctyl)-t-4-(r-4-butyl-t-1-cyclohexyl)-
  cyclohexyl-c-1-carbonitrile
r-1-(8-hydroxyoctyl)-t-4-(r-4-pentyl-t-1-cyclohexyl)-
  cyclohexyl-c-1-carbonitrile
r-1-(8-hydroxyoctyl)-t-4-(r-4-hexyl-t-1-cyclohexyl)-
  cyclohexyl-c-1-carbonitrile
r-1-(8-hydroxyoctyl)-t-4-(r-4-heptyl-t-1-cyclohexyl)-
  cyclohexyl-c-1-carbonitrile
r-1-(8-hydroxyoctyl)-t-4-(r-4-octyl-t-1-cyclohexyl)-
  cyclohexyl-c-1-carbonitrile
r-1-(9-hydroxynonyl)-t-4-(r-4-ethyl-t-1-cyclohexyl)-
  cyclohexyl-c-1-carbonitrile
r-1-(9-hydroxynonyl)-t-4-(r-4-propyl-t-1-cyclohexyl)-
  cyclohexyl-c-1-carbonitrile
r-1-(9-hydroxynonyl)-t-4-(r-4-butyl-t-1-cyclohexyl)-
  cyclohexyl-c-1-carbonitrile
r-1-(9-hydroxynonyl)-t-4-(r-4-pentyl-t-1-cyclohexyl)-
  cyclohexyl-c-1-carbonitrile
r-1-(9-hydroxynonyl)-t-4-(r-4-hexyl-t-1-cyclohexyl)-
  cyclohexyl-c-1-carbonitrile
r-1-(9-hydroxynonyl)-t-4-(r-4-heptyl-t-1-cyclohexyl)-
  cyclohexyl-c-1-carbonitrile
r-1-(9-hydroxynonyl)-t-4-(r-4-octyl-t-1-cyclohexyl)-
  cyclohexyl-c-1-carbonitrile
r-1-(10-hydroxydecyl)-t-4-(r-4-ethyl-t-1-cyclohexyl)-
  cyclohexyl-c-1-carbonitrile
r-1-(10-hydroxydecyl)-t-4-(r-4-propyl-t-1-cyclohexyl)-
  cyclohexyl-c-1-carbonitrile
r-1-(10-hydroxydecyl)-t-4-(r-4-butyl-t-1-cyclohexyl)-
  cyclohexyl-c-1-carbonitrile
r-1-(10-hydroxydecyl)-t-4-(r-4-pentyl-t-1-cyclohexyl)-
  cyclohexyl-c-1-carbonitrile
r-1-(10-hydroxydecyl)-t-4-(r-4-hexyl-t-1-cyclohexyl)-
  cyclohexyl-c-1-carbonitrile
r-1-(10-hydroxydecyl)-t-4-(r-4-heptyl-t-1-cyclohexyl)-
  cyclohexyl-c-1-carbonitrile
r-1-(10-hydroxydecyl)-t-4-(r-4-octyl-t-1-cyclohexyl)-
  cyclohexyl-c-1-carbonitrile
r-1-(11-hydroxyundecyl)-t-4-(r-4-ethyl-t-1-cyclohexyl)-
  cyclohexyl-c-1-carbonitrile
r-1-(11-hydroxyundecyl)-t-4-(r-4-propyl-t-1-cyclohex-
  yl)-cyclohexyl-c-1-carbonitrile
r-1-(11-hydroxyundecyl)-t-4-(r-4-butyl-t-1-cyclohexyl)-
  cyclohexyl-c-1-carbonitrile
r-1-(11-hydroxyundecyl)-t-4-(r-4-pentyl-t-1-cyclohex-
  yl)-cyclohexyl-c-1-carbonitrile
r-1-(11-hydroxyundecyl)-t-4-(r-4-hexyl-t-1-cyclohexyl)-
  cyclohexyl-c-1-carbonitrile
r-1-(11-hydroxyundecyl)-t-4-(r-4-heptyl-t-1-cyclohex-
  yl)-cyclohexyl-c-1-carbonitrile
r-1-(11-hydroxyundecyl)-t-4-(r-4-octyl-t-1-cyclohexyl)-
  cyclohexyl-c-1-carbonitrile

EXAMPLE 4

2.7 g of dicyclohexylcarbodiimide in 2 ml of $CH_2Cl_2$ are added at 0° to a solution of 3.9 g of r-1-(4-hydroxybutyl)-t-4-(r-4-pentyl-t-1-cyclohexyl)-cyclohexyl-c-1-carbonitrile (for preparation see Example 3), 1.0 g of methacrylic acid, 143 mg of 4-dimethylaminopyridine and 3 mg of 2,6-di-tert.-butyl-4-methylphenol in 20 ml of $CH_2Cl_2$, and the mixture is then stirred for a further 2 hours at room temperature. The precipitate is filtered off, the filtrate is concentrated and the residue is chromatographed over a silica gel column using 99:1 $CH_2Cl_2$/ethyl acetate. Recrystallization gives 4-[c-1-cyano-r-4-(r-4-pentyl-t-1-cyclohexyl)-t-1-cyclohexyl]-butyl methacrylate of m.p. 36°–37°.

The following are prepared analogously:

4-[c-1-cyano-r-4-(r-4-ethyl-t-1-cyclohexyl)-t-1-cyclohexyl]-butyl methacrylate
4-[c-1-cyano-r-4-(r-4-propyl-t-1-cyclohexyl)-t-1-cyclohexyl]-butyl methacrylate
4-[c-1-cyano-r-4-(r-4-butyl-t-1-cyclohexyl)-t-1-cyclohexyl]-butyl methacrylate
4-[c-1-cyano-r-4-(r-4-hexyl-t-1-cyclohexyl)-t-1-cyclohexyl]-butyl methacrylate
4-[c-1-cyano-r-4-(r-4-heptyl-t-1-cyclohexyl)-t-1-cyclohexyl]-butyl methacrylate
4-[c-1-cyano-r-4-(r-4octyl-t-1-cyclohexyl)-t-1-cyclohexyl]-butyl methacrylate
5-[c-1-cyano-r-4-(r-4-ethyl-t-1-cyclohexyl)-t-1-cyclohexyl]-pentyl methacrylate
5-[c-1-cyano-r-4-(r-4-propyl-t-1-cyclohexyl)-t-1-cyclohexyl]-pentyl methacrylate
5-[c-1-cyano-r-4-(r-4-butyl-t-1-cyclohexyl)-t-1-cyclohexyl]-pentyl methacrylate
5-[c-1-cyano-r-4-(r-4-hexyl-t-1-cyclohexyl)-t-1-cyclohexyl]-pentyl methacrylate
5-[c-1-cyano-r-4-(r-4-heptyl-t-1-cyclohexyl)-t-1-cyclohexyl]-pentyl methacrylate
5-[c-1-cyano-r-4-(r-4-octyl-t-1-cyclohexyl)-t-1-cyclohexyl]-pentyl methacrylate
6-[c-1-cyano-r-4-(r-4-ethyl-t-1-cyclohexyl)-t-1-cyclohexyl]-hexyl methacrylate
6-[c-1-cyano-r-4-(r-4-propyl-t-1-cyclohexyl)-t-1-cyclohexyl]-hexyl methacrylate
6-[c-1-cyano-r-4-(r-4-butyl-t-1-cyclohexyl)-t-1-cyclohexyl]-hexyl methacrylate
6-[c-1-cyano-r-4-(r-4-pentyl-t-1-cyclohexyl)-t-1-cyclohexyl]-hexyl methacrylate
6-[c-1-cyano-r-4-(r-4-hexyl-t-1-cyclohexyl)-t-1-cyclohexyl]-hexyl methacrylate
6-[c-1-cyano-r-4-(r-4-heptyl-t-1-cyclohexyl)-t-1-cyclohexyl]-hexyl methacrylate
6-[c-1-cyano-r-4-(r-4-octyl-t-1-cyclohexyl)-t-1-cyclohexyl]-hexyl methacrylate
7-[c-1-cyano-r-4-(r-4-ethyl-t-1-cyclohexyl)-t-1-cyclohexyl]-heptyl methacrylate
7-[c-1-cyano-r-4-(r-4-propyl-t-1-cyclohexyl)-t-1-cyclohexyl]-heptyl methacrylate
7-[c-1-cyano-r-4-(r-4-butyl-t-1-cyclohexyl)-t-1-cyclohexyl]-heptyl methacrylate
7-[c-1-cyano-r-4-(r-4-pentyl-t-1-cyclohexyl)-t-1-cyclohexyl]-heptyl methacrylate
7-[c-1-cyano-r-4-(r-4-hexyl-t-1-cyclohexyl)-t-1-cyclohexyl]-heptyl methacrylate
7-[c-1-cyano-r-4-(r-4-heptyl-t-1-cyclohexyl)-t-1-cyclohexyl]-heptyl methacrylate
7-[c-1-cyano-r-4-(r-4-octyl-t-1-cyclohexyl)-t-1-cyclohexyl]-heptyl methacrylate
8-[c-1-cyano-r-4-(r-4-ethyl-t-1-cyclohexyl)-t-1-cyclohexyl]-octyl methacrylate
8-[c-1-cyano-r-4-(r-4-propyl-t-1-cyclohexyl)-t-1-cyclohexyl]-octyl methacrylate
8-[c-1-cyano-r-4-(r-4-butyl-t-1-cyclohexyl)-t-1-cyclohexyl]-octyl methacrylate
8-[c-1-cyano-r-4-(r-4-hexyl-t-1-cyclohexyl)-t-1-cyclohexyl]-octyl methacrylate
8-[c-1-cyano-r-4-(r-4-heptyl-t-1-cyclohexyl)-t-1-cyclohexyl]-octyl methacrylate
8-[c-1-cyano-r-4-(r-4-octyl-t-1-cyclohexyl)-t-1-cyclohexyl]-octyl methacrylate
9-[c-1-cyano-r-4-(r-4-ethyl-t-1-cyclohexyl)-t-1-cyclohexyl]-nonyl methacrylate
9-[c-1-cyano-r-4-(r-4-propyl-t-1-cyclohexyl)-t-1-cyclohexyl]-nonyl methacrylate
9-[c-1-cyano-r-4-(r-4-butyl-t-1-cyclohexyl)-t-1-cyclohexyl]-nonyl methacrylate
9-[c-1-cyano-r-4-(r-4-hexyl-t-1-cyclohexyl)-t-1-cyclohexyl]-nonyl methacrylate
9-[c-1-cyano-r-4-(r-4-heptyl-t-1-cyclohexyl)-t-1-cyclohexyl]-nonyl methacrylate
9-[c-1-cyano-r-4-(r-4-octyl-t-1-cyclohexyl)-t-1-cyclohexyl]-nonyl methacrylate
10-[c-1-cyano-r-4-(r-4-ethyl-t-1-cyclohexyl)-t-1-cyclohexyl]-decyl methacrylate
10-[c-1-cyano-r-4-(r-4-propyl-t-1-cyclohexyl)-t-1-cyclohexyl]-decyl methacrylate
10-[c-1-cyano-r-4-(r-4-butyl-t-1-cyclohexyl)-t-1-cyclohexyl]-decyl methacrylate
10-[c-1-cyano-r-4-(r-4-hexyl-t-1-cyclohexyl)-t-1-cyclohexyl]-decyl methacrylate
10-[c-1-cyano-r-4-(r-4-heptyl-t-1-cyclohexyl)-t-1-cyclohexyl]-decyl methacrylate
10-[c-1-cyano-r-4-(r-4-octyl-t-1-cyclohexyl)-t-1-cyclohexyl]-decyl methacrylate
3-[c-1-cyano-r-4-(r-4-ethyl-t-1-cyclohexyl)-t-1-cyclohexyl]-propyl methacrylate
3-[c-1-cyano-r-4-(r-4-propyl-t-1-cyclohexyl)-t-1-cyclohexyl]-propyl methacrylate
3-[c-1-cyano-r-4-(r-4-butyl-t-1-cyclohexyl)-t-1-cyclohexyl]-propyl methacrylate
3-[c-1-cyano-r-4-(r-4-hexyl-t-1-cyclohexyl)-t-1-cyclohexyl]-propyl methacrylate
3-[c-1-cyano-r-4-(r-4-heptyl-t-1-cyclohexyl)-t-1-cyclohexyl]-propyl methacrylate
3-[c-1-cyano-r-4-(r-4-octyl-t-1-cyclohexyl)-t-1-cyclohexyl]-propyl methacrylate

EXAMPLE 5 a) 20 ml of a 15% solution of n-butyllithium in hexane are added, at 0° and with stirring, to a mixture of 3.5 g of diisopropylamine and 30 ml of THF. This mixture is then added at $-70°$ to a solution of 10.3 g of 4-[4'-octyloxy-1,1'-biphenyl-4-yl]-cyclohexylcarbonitrile and 30 ml of THF, and stirring is continued for a further 2 hours. 4.3 g of 1-bromo-3-butene are then added and the reaction mixture is allowed to warm up to 0°.

5 ml of ethanol are added and the mixture is poured into ice water and acidified with 2N HCl. It is extracted with tert.-butyl methyl ether, and the organic phases are worked up. Purification by chromatography over silica get (9:1 petroleum ether/ethyl acetate) and recrystallization give c-4-[4'-octyloxy-1,1'-biphenyl-4-yl]-1-(3-butenyl)-r-1-cyclohexylcarbonitrile of K 69°, $S_C$ 87°, $S_A$ 111°, N 161°.

b) 5.4 g of a 1M solution of borane-THF adduct in THF are added at 0° to a mixture of 6.0 g of olefin, prepared as in a), and 12 ml of THF, and stirring is continued for 1 hour. 1.4 ml of water, 1.8 ml of 3N NaOH and 1.8 ml of 30% $H_2O_2$ are then added and the mixture is stirred for 1 hour at room temperature.

The mixture is poured into water and extracted with tert.-butyl methyl ether, the organic phases are worked up and the residue is chromatographed over silica gel using 85:15 $CH_2Cl_2$/ethyl acetate. Recrystallization from ethanol gives c-4-[4'-octyloxy-1,1'-biphenyl-4-yl]-1-(4-hydroxybutyl)-r-1-cyclohexylcarbonitrile of K 96°, $S_C$ 119°, $S_A$ 151°, N 164° I.

The following are prepared analogously:

c-4-[4'-ethoxy-1,1'-biphenyl-4-yl]-1-(4-hydroxybutyl)-r-1-cyclohexylcarbonitrile
c-4-[4'-propoxy-1,1'-biphenyl-4-yl]-1-(4-hydroxybutyl)-r-1-cyclohexylcarbonitrile
c-4-[4'-butoxy-1,1'-biphenyl-4-yl]-1-(4-hydroxybutyl)-1-cyclohexylcarbonitrile
c-4-[4'-pentyloxy-1,1'-biphenyl-4-yl]-1-(4-hydroxybutyl)r-1-cyclohexylcarbonitrile
c-4-[4'-hexyloxy-1,1'-biphenyl-4-yl]-1-(4-hydroxybutyl)-r-1-cyclohexylcarbonitrile
c-4-[4'-heptyloxy-1,1'-biphenyl-4-yl]-1-(4-hydroxybutyl)-r-1-cyclohexylcarbonitrile
c-4-[4'-ethyl-1,1'-biphenyl-4-yl]-1-(4-hydroxybutyl)-r-1-cyclohexylcarbonitrile
c-4-[4'-propyl-1,1'-biphenyl-4-yl]-1-(4-hydroxybutyl)-r-1-cyclohexylcarbonitrile
c-4-[4'-butyl-1,1'-biphenyl-4-yl]-1-(4-hydroxybutyl)-r-1-cyclohexylcarbonitrile
c-4-[4'-pentyl-1,1'-biphenyl-4-yl]-1-(4-hydroxybutyl)-r-1-cyclohexylcarbonitrile
c-4-[4'-ethoxy-1,1'-biphenyl-4-yl]-1-(5-hydroxypentyl)-r-1-cyclohexylcarbonitrile
c-4-[4'-propoxy-1,1'-biphenyl-4-yl]-1-(5-hydroxypentyl)-r-1-cyclohexylcarbonitrile
c-4-[4'-butoxy-1,1'-biphenyl-4-yl]-1-(5-hydroxypentyl)-r-1-cyclohexylcarbonitrile
c-4-[4'-pentyloxy-1,1'-biphenyl-4-yl]-1-(5-hydroxypentyl)-r-1-cyclohexylcarbonitrile
c-4-[4'-hexyloxy-1,1'-biphenyl-4-yl]-1-(5-hydroxypentyl)-r-1-cyclohexylcarbonitrile
c-4-[4'-heptyloxy-1,1'-biphenyl-4-yl]-1-(5-hydroxypentyl)-r-1-cyclohexylcarbonitrile
c-4-[4'-octyloxy-1,1'-biphenyl-4-yl]-1-(5-hydroxypentyl)-r-1-cyclohexylcarbonitrile
c-4-[4'-ethyl-1,1'-biphenyl-4-yl]-1-(5-hydroxypentyl)-r-1-cyclohexylcarbonitrile
c-4-[4'-propyl-1,1'-biphenyl-4-yl]-1-(5-hydroxypentyl)-r-1-cyclohexylcarbonitrile
c-4-[4'-butyl-1,1'-biphenyl-4-yl]-1-(5-hydroxypentyl)-r-1-cyclohexylcarbonitrile
c-4-[4'-pentyl-1,1'-biphenyl-4-yl]-1-(5-hydroxypentyl)-r-1-cyclohexylcarbonitrile
c-4-[4'-ethoxy-1,1'-biphenyl-4-yl]-1-(6-hydroxyhexyl)-r-1-cyclohexylcarbonitrile
c-4-[4'-propoxy-1,1'-biphenyl-4-yl]-1-(6-hydroxyhexyl)-r-1-cyclohexylcarbonitrile
c-4-[4'-butoxy-1,1'-biphenyl-4-yl]-1-(6-hydroxyhexyl)-r-1-cyclohexylcarbonitrile
c-4-[4'-pentyloxy-1,1'-biphenyl-4-yl]-1-(6-hydroxyhexyl)-r-1-cyclohexylcarbonitrile
c-4-[4'-hexyloxy-1,1'-biphenyl-4-yl]-1-(6-hydroxyhexyl)-r-1-cyclohexylcarbonitrile
c-4-[4'-heptyloxy-1,1'-biphenyl-4-yl]-1-(6-hydroxyhexyl)-r-1-cyclohexylcarbonitrile
c-4-[4'-octyloxy-1,1'-biphenyl-4-yl]-1-(6-hydroxyhexyl)-r-1-cyclohexylcarbonitrile
c-4-[4'-ethyl-1,1'-biphenyl-4-yl]-1-(6-hydroxyhexyl)-r-1-cyclohexylcarbonitrile
c-4-[4'-propyl-1,1'-biphenyl-4-yl]-1-(6-hydroxyhexyl)-r-1-cyclohexylcarbonitrile
c-4-[4'-butyl-1,1'-biphenyl-4-yl]-1-(6-hydroxyhexyl)-r-1-cyclohexylcarbonitrile
c-4-[4'-pentyl-1,1'-biphenyl-4-yl]-1-(6-hydroxyhexyl)-r-1-cyclohexylcarbonitrile
c-4-[4'-ethoxy-1,1'-biphenyl-4-yl]-1-(7-hydroxyheptyl)-r-1-cyclohexylcarbonitrile
c-4-[4'-propoxy-1,1'-biphenyl-4-yl]-1-(7-hydroxyheptyl)-r-1-cyclohexylcarbonitrile
c-4-[4'-butoxy-1,1'-biphenyl-4-yl]-1-(7-hydroxyheptyl)-r-1-cyclohexylcarbonitrile
c-4-[4'-pentyloxy-1,1'-biphenyl-4-yl]-1-(7-hydroxyheptyl)-r-1-cyclohexylcarbonitrile
c-4-[4'-hexyloxy-1,1'-biphenyl-4-yl]-1-(7-hydroxyheptyl)-r-1-cyclohexylcarbonitrile
c-4-[4'-heptyloxy-1,1'-biphenyl-4-yl]-1-(7-hydroxyheptyl)-r-1-cyclohexylcarbonitrile
c-4-[4'-octyloxy-1,1'-biphenyl-4-yl]-1-(7-hydroxyheptyl)-r-1-cyclohexylcarbonitrile
c-4-[4'-ethyl-1,1'-biphenyl-4-yl]-1-(7-hydroxyheptyl)-r-1-cyclohexylcarbonitrile
c-4-[4'-propyl-1,1'-biphenyl-4-yl]-1-(7-hydroxyheptyl)-r-1-cyclohexylcarbonitrile
c-4-[4'-butyl-1,1'-biphenyl-4-yl]-1-(7-hydroxyheptyl)-r-1-cyclohexylcarbonitrile
c-4-[4'-pentyl-1,1'-biphenyl-4-yl]-1-(7-hydroxyheptyl)-r-1-cyclohexylcarbonitrile
c-4-[4'-ethoxy-1,1'-biphenyl-4-yl]-1-(8-hydroxyoctyl)-r-1-cyclohexylcarbonitrile
c-4-[4'-propoxy-1,1'-biphenyl-4-yl]-1-(8-hydroxyoctyl)-r-1-cyclohexylcarbonitrile
c-4-[4'-butoxy-1,1'-biphenyl-4-yl]-1-(8-hydroxyoctyl)-r-1-cyclohexylcarbonitrile
c-4-[4'-pentyloxy-1,1'-biphenyl-4-yl]-1-(8-hydroxyoctyl)-r-1-cyclohexylcarbonitrile
c-4-[4'-hexyloxy-1,1'-biphenyl-4-yl]-1-(8-hydroxyoctyl)-r-1-cyclohexylcarbonitrile
c-4-[4'-heptyloxy-1,1'-biphenyl-4-yl]-1-(8-hydroxyoctyl)-r-1-cyclohexylcarbonitrile
c-4-[4'-octyloxy-1,1'-biphenyl-4-yl]-1-(8-hydroxyoctyl)-r-1-cyclohexylcarbonitrile
c-4-[4'-ethyl-1,1'-biphenyl-4-yl]-1-(8-hydroxyoctyl)-r-1-cyclohexylcarbonitrile
c-4-[4'-propyl-1,1'-biphenyl-4-yl]-1-(8-hydroxyoctyl)-r-1-cyclohexylcarbonitrile
c-4-[4'-butyl-1,1'-biphenyl-4-yl]-1-(8-hydroxyoctyl)-r-1-cyclohexylcarbonitrile
c-4-[4'-pentyl-1,1'-biphenyl-4-yl]-1-(8-hydroxyoctyl)-r-1-cyclohexylcarbonitrile
c-4-[4'-ethoxy-1,1'-biphenyl-4-yl]-1-(9-hydroxynonyl)-r-1-cyclohexylcarbonitrile
c-4-[4'-propoxy-1,1'-biphenyl-4-yl]-1-(9-hydroxynonyl)-r-1-cyclohexylcarbonitrile
c-4-[4'-butoxy-1,1'-biphenyl-4-yl]-1-(9-hydroxynonyl)-r-1-cyclohexylcarbonitrile
c-4-[4'-pentyloxy-1,1'-biphenyl-4-yl]-1-(9-hydroxynonyl)-r-1-cyclohexylcarbonitrile
c-4-[4'-hexyloxy-1,1'-biphenyl-4-yl]-1-(9-hydroxynonyl)-r-1-cyclohexylcarbonitrile
c-4-[4'-heptyloxy-1,1'-biphenyl-4-yl]-1-(9-hydroxynonyl)-r-1-cyclohexylcarbonitrile
c-4-[4'-octyloxy-1,1'-biphenyl-4-yl]-1-(9-hydroxynonyl)-r-1-cyclohexylcarbonitrile
c-4-[4'-ethyl-1,1'-biphenyl-4-yl]-1-(9-hydroxynonyl)-r-1-cyclohexylcarbonitrile c-4-[4'-propyl-1,1'-biphenyl-4-yl]-1-(9-hydroxynonyl)-r-1-cyclohexylcarbonitrile
c-4-[4'-butyl-1,1'-biphenyl-4-yl]-1-(9-hydroxynonyl)-r-1-cyclohexylcarbonitrile
c-4-[4'-pentyl-1,1'-biphenyl-4-yl]-1-(9-hydroxynonyl)-r-1-cyclohexylcarbonitrile
c-4-[4'-ethoxy-1,1'-biphenyl-4-yl]-1-(10-hydroxydecyl)-r-1-cyclohexylcarbonitrile
c-4-[4'-propoxy-1,1'-biphenyl-4-yl]-1-(10-hydroxydecyl)-r-1-cyclohexylcarbonitrile
c-4-[4'-butoxy-1,1'-biphenyl-4-yl]-1-(10-hydroxydecyl)-r-1-cyclohexylcarbonitrile
c-4-[4'-pentyloxy-1,1'-biphenyl-4-yl]-1-(10-hydroxydecyl)-r-1-cyclohexylcarbonitrile
c-4-[4'-hexyloxy-1,1'-biphenyl-4-yl]-1-(10-hydroxydecyl)-r-1-cyclohexylcarbonitrile
c-4-[4'-heptyloxy-1,1'-biphenyl-4-yl]-1-(10-hydroxydecyl)-r-1-cyclohexylcarbonitrile
c-4-[4'-octyloxy-1,1'-biphenyl-4-yl]-1-(10-hydroxydecyl)-r-1-cyclohexylcarbonitrile
c-4-[4'-ethyl-1,1'-biphenyl-4-yl]-1-(10-hydroxydecyl)-r-1-cyclohexylcarbonitrile
c-4-[4'-propyl-1,1'-biphenyl-4-yl]-1-(10-hydroxydecyl)-r-1-cyclohexylcarbonitrile
c-4-[4'-butyl-1,1'-biphenyl-4-yl]-1-(10-hydroxydecyl)-r-1-cyclohexylcarbonitrile
c-4-[4'-pentyl-1,1'-biphenyl-4-yl]-1-(10-hydroxydecyl)-r-1-cyclohexylcarbonitrile
c-4-[4'-ethoxy-1,1'-biphenyl-4-yl]-1-(11-hydroxyundecyl)-r-1-cyclohexylcarbonitrile
c-4-[4'-propoxy-1,1'-biphenyl-4-yl]-1-(11-hydroxyundecyl)-r-1-cyclohexylcarbonitrile
c-4-[4'-butoxy-1,1'-biphenyl-4-yl]-1-(11-hydroxyundecyl)-r-1-cyclohexylcarbonitrile
c-4-[4'-pentyloxy-1,1'-biphenyl-4-yl]-1-(11-hydroxyundecyl)-r-1-cyclohexylcarbonitrile
c-4-[4'-hexyloxy-1,1'-biphenyl-4-yl]-1-(11-hydroxyundecyl)-r-1-cyclohexylcarbonitrile
c-4-[4'-heptyloxy-1,1'-biphenyl-4-yl]-1-(11-hydroxyundecyl)-r-1-cyclohexylcarbonitrile
c-4-[4'-octyloxy-1,1'-biphenyl-4-yl]-1-(11-hydroxyundecyl)-r-1-cyclohexylcarbonitrile
c-4-[4'-ethyl-1,1'-biphenyl-4-yl]-1-(11-hydroxyundecyl)-r-1-cyclohexylcarbonitrile
c-4-[4'-propyl-1,1'-biphenyl-4-yl]-1-(11-hydroxyundecyl)-r-1-cyclohexylcarbonitrile
c-4-[4'-butyl-1,1'-biphenyl-4-yl]-1-(11-hydroxyundecyl)-r-1-cyclohexylcarbonitrile
c-4-[4'-pentyl-1,1'-biphenyl-4-yl]-1-(11-hydroxyundecyl)-r-1-cyclohexylcarbonitrile
c-4-[4'-(2-methylbutoxy)-1,1'-biphenyl-4-yl]-1-(11-hydroxyundecyl)-r-1-cyclohexylcarbonitrile, optically active
c-4-[4'-(2-methylbutoxy)-1,1'-biphenyl-4-yl]-1-(10-hydroxydecyl)-r-1-cyclohexylcarbonitrile, optically active
c-4-[4'-(2-methylbutoxy)-1,1'-biphenyl-4-yl]-1-(9-hydroxynonyl)-r-1-cyclohexylcarbonitrile, optically active
c-4-[4'-(2-methylbutoxy)-1,1'-biphenyl-4-yl]-1-(8-hydroxyoctyl)-r-1-cyclohexylcarbonitrile, optically active
c-4-[4'-(2-methylbutoxy)-1,1'-biphenyl-4-yl]-1-(7-hydroxyheptyl)-r-1-cyclohexylcarbonitrile, optically active
c-4-[4'-(2-octyloxy)-1,1'-biphenyl-4-yl]-1-(11-hydroxyundecyl)-r-1-cyclohexylcarbonitrile, optically active
c-4-[4'-(2-octyloxy)-1,1'-biphenyl-4-yl]-1-(10-hydroxydecyl)-r-1-cyclohexylcarbonitrile, optically active
c-4-[4'-(2-octyloxy)-1,1'-biphenyl-4-yl]-1-(9-hydroxynonyl)-r-1-cyclohexylcarbonitrile, optically active
c-4-[4'-(2-octyloxy)-1,1'-biphenyl-4-yl]-1-(8-hydroxyoctyl)-r-1-cyclohexylcarbonitrile, optically active
c-4-[4'-(2-octyloxy)-1,1'-biphenyl-4-yl]-1-(7-hydroxyheptyl)-r-1-cyclohexylcarbonitrile, optically active

EXAMPLE 6

A solution of 1.08 g of dicyclohexylcarbodiimide (DCCI) in 2 ml of $CH_2Cl_2$ are added at 0° to a mixture of 2.2 g of c-4-[4'-octyloxy-1,1'-biphenyl-4-yl]-1-(4-hydroxybutyl)-r-1-cyclohexylcarbonitrile (for preparation see Example 5), 0.41 g of methacrylic acid, 58 mg of 4-dimethylaminopyridine, 2 mg of 2,6-di-tert.-butyl-4-methylphenol and 10 ml of $CH_2Cl_2$, and the mixture is then stirred for 2 hours at room temperature. The precipitate is filtered off, the filtrate is concentrated and the residue is chromatographed over silica gel using 9:1 petroleum ether/ethyl acetate. Recrystallization gives c-4-[4'-octyloxy-1,1'-biphenyl-4-yl]-1-(4-methacryloyloxybutyl)-r-1-cyclohexylcarbonitrile of K 81°, $S_A$ 124°, N 126° I [$S_C$ 39° $S_A$].

The following are prepared analogously:
c-4-[4'-ethoxy-1,1'-biphenyl-4-yl]-1-(4-methacryloyloxybutyl)-r-1-cyclohexylcarbonitrile
c-4-[4'-propoxy-1,1'-biphenyl-4-yl]-1-(4-methacryloyloxybutyl)-r-1-cyclohexylcarbonitrile
c-4-[4'-butoxy-1,1'-biphenyl-4-yl]-1-(4-methacryloyloxybutyl)-r-1-cyclohexylcarbonitrile
c-4-[4'-pentyloxy-1,1'-biphenyl-4-yl]-1-(4-methacryloyloxybutyl)-r-1-cyclohexylcarbonitrile
c-4-[4'-hexyloxy-1,1'-biphenyl-4-yl]-1-(4-methacryloyloxybutyl)-r-1-cyclohexylcarbonitrile
c-4-[4'-heptyloxy-1,1'-biphenyl-4-yl]-1-(4-methacryloyloxybutyl)-r-1-cyclohexylcarbonitrile
c-4-[4'-ethyl-1,1'-biphenyl-4-yl]-1-(4-methacryloyloxybutyl)-r-1-cyclohexylcarbonitrile
c-4-[4'-propyl-1,1'-biphenyl-4-yl]-1-(4-methacryloyloxybutyl)-r-1-cyclohexylcarbonitrile
c-4-[4'-butyl-1,1'-biphenyl-4-yl]-1-(4-methacryloyloxybutyl)-r-1-cyclohexylcarbonitrile
c-4-[4'-pentyl-1,1'-biphenyl-4-yl]-1-(4-methacryloyloxybutyl)-r-1-cyclohexylcarbonitrile
c-4-[4'-ethoxy-1,1'-biphenyl-5-yl]-1-(5-methacryloyloxypentyl)-r-1-cyclohexylcarbonitrile
c-4-[4'-propoxy-1,1'-biphenyl-5-yl]-1-(5-methacryloyloxypentyl)-r-1-cyclohexylcarbonitrile
c-4-[4'-butoxy-1,1'-biphenyl-5-yl]-1-(5-methacryloyloxypentyl)-r-1-cyclohexylcarbonitrile
c-4-[4'-pentyloxy-1,1'-biphenyl-5-yl]-1-(5-methacryloyloxypentyl)-r-1-cyclohexylcarbonitrile
c-4-[4'-hexyloxy-1,1'-biphenyl-5-yl]-1-(5-methacryloyloxypentyl)-r-1-cyclohexylcarbonitrile
c-4-[4'-heptyloxy-1,1'-biphenyl-5-yl]-1-(5-methacryloyloxypentyl)-r-1-cyclohexylcarbonitrile
c-4-[4'-octyloxy-1,1'-biphenyl-5-yl]-1-(5-methacryloyloxypentyl)-r-1-cyclohexylcarbonitrile
c-4-[4'-ethyl-1,1'-biphenyl-5-yl]-1-(5-methacryloyloxypentyl)-r-1-cyclohexylcarbonitrile
c-4-[4'-propyl-1,1'-biphenyl-5-yl]-1-(5-methacryloyloxypentyl)-r-1-cyclohexylcarbonitrile
c-4-[4'-butyl-1,1'-biphenyl-5-yl]-1-(5-methacryloyloxypentyl)-r-1-cyclohexylcarbonitrile
c-4-[4'-pentyl-1,1'-biphenyl-5-yl]-1-(5-methacryloyloxypentyl)-r-1-cyclohexylcarbonitrile c-4-[4'-ethoxy-1,1'-biphenyl-4-yl]-1-(6-methacryloyloxyhexyl)-r-1-cyclohexylcarbonitrile
c-4-[4'-propoxy-1,1'-biphenyl-4-yl]-1-(6-methacryloyloxyhexyl)-r-1-cyclohexylcarbonitrile
c-4-[4'-butoxy-1,1'-biphenyl-4-yl]-1-(6-methacryloyloxyhexyl)-r-1-cyclohexylcarbonitrile
c-4-[4'-pentyloxy-1,1'-biphenyl-4-yl]-1-(6-methacryloyloxyhexyl)-r-1-cyclohexylcarbonitrile
c-4-[4'-hexyloxy-1,1'-biphenyl-4-yl]-1-(6-methacryloyloxyhexyl)-r-1-cyclohexylcarbonitrile
c-4-[4'-heptyloxy-1,1'-biphenyl-4-yl]-1-(6-methacryloyloxyhexyl)-r-1-cyclohexylcarbonitrile
c-4-[4'-octyloxy-1,1'-biphenyl-4-yl]-1-(6-methacryloyloxyhexyl)-r-1-cyclohexylcarbonitrile
c-4-[4'-ethyl-1,1'-biphenyl-4-yl]-1-(6-methacryloyloxyhexyl)-r-1-cyclohexylcarbonitrile
c-4-[4'-propyl-1,1'-biphenyl-4-yl]-1-(6-methacryloyloxyhexyl)-r-1-cyclohexylcarbonitrile
c-4-[4'-butyl-1,1'-biphenyl-4-yl]-1-(6-methacryloyloxyhexyl)-r-1-cyclohexylcarbonitrile
c-4-[4'-pentyl-1,1'-biphenyl-4-yl]-1-(6-methacryloyloxyhexyl)-r-1-cyclohexylcarbonitrile
c-4-[4'-ethoxy-1,1'-biphenyl-4-yl]-1-(7-methacryloyloxyheptyl)-r-1-cyclohexylcarbonitrile
c-4-[4'-propoxy-1,1'-biphenyl-4-yl]-1-(7-methacryloyloxyheptyl)-r-1-cyclohexylcarbonitrile
c-4-[4'-butoxy-1,1'-biphenyl-4-yl]-1-(7-methacryloyloxyheptyl)-r-1-cyclohexylcarbonitrile
c-4-[4'-pentyloxy-1,1'-biphenyl-4-yl]-1-(7-methacryloyloxyheptyl)-r-1-cyclohexylcarbonitrile
c-4-[4'-hexyloxy-1,1'-biphenyl-4-yl]-1-(7-methacryloyloxyheptyl)-r-1-cyclohexylcarbonitrile
c-4-[4'-heptyloxy-1,1'-biphenyl-4-yl]-1-(7-methacryloyloxyheptyl)-r-1-cyclohexylcarbonitrile
c-4-[4'-octyloxy-1,1'-biphenyl-4-yl]-1-(7-methacryloyloxyheptyl)-r-1-cyclohexylcarbonitrile
c-4-[4'-ethyl-1,1'-biphenyl-4-yl]-1-(7-methacryloyloxyheptyl)-r-1-cyclohexylcarbonitrile
c-4-[4'-propyl-1,1'-biphenyl-4-yl]-1-(7-methacryloyloxyheptyl)-r-1-cyclohexylcarbonitrile
c-4-[4'-butyl-1,1'-biphenyl-4-yl]-1-(7-methacryloyloxyheptyl)-r-1-cyclohexylcarbonitrile
c-4-[4'-pentyl-1,1'-biphenyl-4-yl]-1-(7-methacryloyloxyheptyl)-r-1-cyclohexylcarbonitrile
c-4-[4'-ethoxy-1,1'-biphenyl-4-yl]-1-(8-methacryloyloxyoctyl)-r-1-cyclohexylcarbonitrile
c-4-[4'-propoxy-1,1'-biphenyl-4-yl]-1-(8-methacryloyloxyoctyl)-r-1-cyclohexylcarbonitrile
c-4-[4'-butoxy-1,1'-biphenyl-4-yl]-1-(8-methacryloyloxyoctyl)-r-1-cyclohexylcarbonitrile
c-4-[4'-pentyloxy-1,1'-biphenyl-4-yl]-1-(8-methacryloyloxyoctyl)-r-1-cyclohexylcarbonitrile
c-4-[4'-hexyloxy-1,1'-biphenyl-4-yl]-1-(8-methacryloyloxyoctyl)-r-1-cyclohexylcarbonitrile
c-4-[4'-heptyloxy-1,1'-biphenyl-4-yl]-1-(8-methacryloyloxyoctyl)-r-1-cyclohexylcarbonitrile
c-4-[4'-octyloxy-1,1'-biphenyl-4-yl]-1-(8-methacryloyloxyoctyl)-r-1-cyclohexylcarbonitrile
c-4-[4'-ethyl-1,1'-biphenyl-4-yl]-1-(8-methacryloyloxyoctyl)-r-1-cyclohexylcarbonitrile
c-4-[4'-propyl-1,1'-biphenyl-4-yl]-1-(8-methacryloyloxyoctyl)-r-1-cyclohexylcarbonitrile
c-4-[4'-butyl-1,1'-biphenyl-4-yl]-1-(8-methacryloyloxyoctyl)-r-1-cyclohexylcarbonitrile
c-4-[4'-pentyl-1,1'-biphenyl-4-yl]-1-(8-methacryloyloxyoctyl)-r-1-cyclohexylcarbonitrile
c-4-[4'-ethoxy-1,1'-biphenyl-4-yl]-1-(9-methacryloyloxynonyl)-r-1-cyclohexylcarbonitrile
c-4-[4'-propoxy-1,1'-biphenyl-4-yl]-1-(9-methacryloyloxynonyl)-r-1-cyclohexylcarbonitrile
c-4-[4'-butoxy-1,1'-biphenyl-4-yl]-1-(9-methacryloyloxynonyl)-r-1-cyclohexylcarbonitrile
c-4-[4'-pentyloxy-1,1'-biphenyl-4-yl]-1-(9-methacryloyloxynonyl)-r-1-cyclohexylcarbonitrile
c-4-[4'-hexyloxy-1,1'-biphenyl-4-yl]-1-(9-methacryloyloxynonyl)-r-1-cyclohexylcarbonitrile
c-4-[4'-heptyloxy-1,1'-biphenyl-4-yl]-1-(9-methacryloyloxynonyl)-r-1-cyclohexylcarbonitrile
c-4-[4'-octyloxy-1,1'-biphenyl-4-yl]-1-(9-methacryloyloxynonyl)-r-1-cyclohexylcarbonitrile
c-4-[4'-ethyl-1,1'-biphenyl-4-yl]-1-(9-methacryloyloxynonyl)-r-1-cyclohexylcarbonitrile
c-4-[4'-propyl-1,1'-biphenyl-4-yl]-1-(9-methacryloyloxynonyl)-r-1-cyclohexylcarbonitrile
c-4-[4'-butyl-1,1'-biphenyl-4-yl]-1-(9-methacryloyloxynonyl)-r-1-cyclohexylcarbonitrile
c-4-[4'-pentyl-1,1'-biphenyl-4-yl]-1-(9-methacryloyloxynonyl)-r-1-cyclohexylcarbonitrile
c-4-[4'-ethoxy-1,1'-biphenyl-4-yl]-1-(10-methacryloyloxydecyl)-r-1-cyclohexylcarbonitrile
c-4-[4'-propoxy-1,1'-biphenyl-4-yl]-1-(10-methacryloyloxydecyl)-r-1-cyclohexylcarbonitrile
c-4-[4'-butoxy-1,1'-biphenyl-4-yl]-1-(10-methacryloyloxydecyl)-r-1-cyclohexylcarbonitrile
c-4-[4'-pentyloxy-1,1'-biphenyl-4-yl]-1-(10-methacryloyloxydecyl)-r-1-cyclohexylcarbonitrile
c-4-[4'-hexyloxy-1,1'-biphenyl-4-yl]-1-(10-methacryloyloxydecyl)-r-1-cyclohexylcarbonitrile
c-4-[4'-heptyloxy-1,1'-biphenyl-4-yl]-1-(10-methacryloyloxydecyl)-r-1-cyclohexylcarbonitrile
c-4-[4'-octyloxy-1,1'-biphenyl-4-yl]-1-(10-methacryloyloxydecyl)-r-1-cyclohexylcarbonitrile
c-4-[4'-ethyl-1,1'-biphenyl-4-yl]-1-(10-methacryloyloxydecyl)-r-1-cyclohexylcarbonitrile
c-4-[4'-propyl-1,1'-biphenyl-4-yl]-1-(10-methacryloyloxydecyl)-r-1-cyclohexylcarbonitrile
c-4-[4'-butyl-1,1'-biphenyl-4-yl]-1-(10-methacryloyloxydecyl)-r-1-cyclohexylcarbonitrile
c-4-[4'-pentyl-1,1'-biphenyl-4-yl]-1-(10-methacryloyloxydecyl)-r-1-cyclohexylcarbonitrile
c-4-[4'-ethoxy-1,1'-biphenyl-4-yl]-1-(11-methacryloyloxyundecyl)-r-1-cyclohexylcarbonitrile
c-4-[4'-propoxy-1,1'-biphenyl-4-yl]-1-(11-methacryloyloxyundecyl)-r-1-cyclohexylcarbonitrile
c-4-[4'-butoxy-1,1'-biphenyl-4-yl]-1-(11-methacryloyloxyundecyl)-r-1-cyclohexylcarbonitrile
c-4-[4'-pentyloxy-1,1'-biphenyl-4-yl]-1-(11-methacryloyloxyundecyl)-r-1-cyclohexylcarbonitrile
c-4-[4'-hexyloxy-1,1'-biphenyl-4-yl]-1-(11-methacryloyloxyundecyl)-r-1-cyclohexylcarbonitrile
c-4-[4'-heptyloxy-1,1'-biphenyl-4-yl]-1-(11-methacryloyloxyundecyl)-r-1-cyclohexylcarbonitrile
c-4-[4'-octyloxy-1,1'-biphenyl-4-yl]-1-(11-methacryloyloxyundecyl)-r-1-cyclohexylcarbonitrile
c-4-[4'-ethyl-1,1'-biphenyl-4-yl]-1-(11-methacryloyloxyundecyl)-r-1-cyclohexylcarbonitrile
c-4-[4'-propyl-1,1'-biphenyl-4-yl]-1-(11-methacryloyloxyundecyl)-r-1-cyclohexylcarbonitrile
c-4-[4'-butyl-1,1'-biphenyl-4-yl]-1-(11-methacryloyloxyundecyl)-r-1-cyclohexylcarbonitrile
c-4-[4'-pentyl-1,1'-biphenyl-4-yl]-1-(11-methacryloyloxyundecyl)-r-1-cyclohexylcarbonitrile
c-4-[4'-(2-methylbutoxy)-1,1'-biphenyl-4-yl]-1-(11-methacryloyloxyundecyl)-r-1-cyclohexylcarbonitrile, optically active c-4-[4'-(2-methylbutoxy)-1,1'-biphenyl-4-yl]-1-(10-methacryloyloxydecyl)-r-1-cyclohexylcarbonitrile, optically active c-4-[4'-(2-methylbutoxy)-1,1'-biphenyl-4-yl]-1-(9-methacryloyloxynonyl)-r-1-cyclohexylcarbonitrile, optically active c-4-[4'-(2-methylbutoxy)-1,1'-biphenyl-4-yl]-1-(8-methacryloyloxyoctyl)-r-1-cyclohexylcarbonitrile, optically active c-4-[4'-(2-methylbutoxy)-1,1'-biphenyl-4-yl]-1-(7-methacryloyloxyheptyl)-r-1-cyclohexylcarbonitrile, optically active c-4-[4'-(2-octyloxy-1,1'-biphenyl-4-yl]-1-(11-methacryloyloxyundecyl)-r-1-cyclohexylcarbonitrile, optically active c-4-[4'-(2-octyloxy-1,1'-biphenyl-4-yl]-1-(10-methacryloyloxydecyl)-r-1-cyclohexylcarbonitrile, optically active c-4-[4'-(2-octyloxy-1,1'-biphenyl-4-yl]-1-(9-methacryloyloxynonyl)-r-1-cyclohexylcarbonitrile, optically active c-4-[4'-(2-octyloxy-1,1'-biphenyl-4-yl]-1-(8-methacryloyloxyoctyl)-r-1-cyclohexylcarbonitrile, optically active c-4-[4'-(2-octyloxy-1,1'-biphenyl-4-yl]-1-(7-methacryloyloxyheptyl)-r-1-cyclohexylcarbonitrile, optically active

EXAMPLE 7

The corresponding
c-4-[4'-octyloxy-1,1'-biphenyl-4-yl]-1-(4-acryloyloxybutyl)-r-1-cyclohexylcarbonitrile is obtained analogously to Example 6 from c-4-[4'-octyloxy-1,1'-biphenyl-4-yl]-1-(4-hydroxybutyl)-r-1-cyclohexylcarbonitrile and acrylic acid.

The following are prepared analogously:

c-4-[4'-ethoxy-1,1'-biphenyl-4-yl]-1-(4-acryloyloxybutyl)-r-1-cyclohexylcarbonitrile c-4-[4'-propoxy-1,1'-biphenyl-4-yl]-1-(4-acryloyloxybutyl)-r-1-cyclohexylcarbonitrile c-4-[4'-butoxy-1,1'-biphenyl-4-yl]-1-(4-acryloyloxybutyl)-r-1-cyclohexylcarbonitrile c-4-[4'-pentyloxy-1,1'-biphenyl-4-yl]-1-(4-acryloyloxybutyl)-r-1-cyclohexylcarbonitrile c-4-[4'-hexyloxy-1,1'-biphenyl-4-yl]-1-(4-acryloyloxybutyl)-r-1-cyclohexylcarbonitrile c-4-[4'-heptyloxy-1,1'-biphenyl-4-yl]-1-(4-acryloyloxybutyl)-r-1-cyclohexylcarbonitrile c-4-[4'-ethyl-1,1'-biphenyl-4-yl]-1-(4-acryloyloxybutyl)-r-1-cyclohexylcarbonitrile c-4-[4'-propyl-1,1'-biphenyl-4-yl]-1-(4-acryloyloxybutyl)-r-1-cyclohexylcarbonitrile c-4-[4'-butyl-1,1'-biphenyl-4-yl]-1-(4-acryloyloxybutyl)-r-1-cyclohexylcarbonitrile c-4-[4'-pentyl-1,1'-biphenyl-4-yl]-1-(4-acryloyloxybutyl)-r-1-cyclohexylcarbonitrile c-4-[4'-ethoxy-1,1'-biphenyl-5-yl]-1-(5-acryloyloxypentyl)-r-1-cyclohexylcarbonitrile c-4-[4'-propoxy-1,1'-biphenyl-5-yl]-1-(5-acryloyloxypentyl)-r-1-cyclohexylcarbonitrile c-4-[4'-butoxy-1,1'-biphenyl-5-yl]-1-(5-acryloyloxypentyl)-r-1-cyclohexylcarbonitrile c-4-[4'-pentyloxy-1,1'-biphenyl-5-yl]-1-(5-acryloyloxypentyl)-r-1-cyclohexylcarbonitrile c-4-[4'-hexyloxy-1,1'-biphenyl-5-yl]-1-(5-acryloyloxypentyl)-r-1-cyclohexylcarbonitrile c-4-[4'-heptyloxy-1,1'-biphenyl-5-yl]-1-(5-acryloyloxypentyl)-r-1-cyclohexylcarbonitrile c-4-[4'-octyloxy-1,1'-biphenyl-5-yl]-1-(5-acryloyloxypentyl)-r-1-cyclohexylcarbonitrile c-4-[4'-ethyl-1,1'-biphenyl-5-yl]-1-(5-acryloyloxypentyl)-r-1-cyclohexylcarbonitrile c-4-[4'-propyl-1,1'-biphenyl-5-yl]-1-(5-acryloyloxypentyl)-r-1-cyclohexylcarbonitrile c-4-[4'-butyl-1,1'-biphenyl-5-yl]-1-(5-acryloyloxypentyl)-r-1-cyclohexylcarbonitrile c-4-[4'-pentyl-1,1'-biphenyl-5-yl]-1-(5-acryloyloxypentyl)-r-1-cyclohexylcarbonitrile c-4-[4'-ethoxy-1,1'-biphenyl-4-yl]-1-(6-acryloyloxyhexyl)-r-1-cyclohexylcarbonitrile c-4-[4'-propoxy-1,1'-biphenyl-4-yl]-1-(6-acryloyloxyhexyl)-r-1-cyclohexylcarbonitrile c-4-[4'-butoxy-1,1'-biphenyl-4-yl]-1-(6-acryloyloxyhexyl)-r-1-cyclohexylcarbonitrile c-4-[4,-pentyloxy-1,1'-biphenyl-4-yl]-1-(6-acryloyloxyhexyl)-r-1-cyclohexylcarbonitrile c-4-[4'-hexyloxy-1,1'-biphenyl-4-yl]-1-(6-acryloyloxyhexyl)-r-1-cyclohexylcarbonitrile c-4-[4'-heptyloxy-1,1'-biphenyl-4-yl]-1-(6-acryloyloxyhexyl)-r-1-cyclohexylcarbonitrile c-4-[4'-octyloxy-1,1'-biphenyl-4-yl]-1-(6-acryloyloxyhexyl)-r-1-cyclohexylcarbonitrile c-4-[4'-ethyl-1,1'-biphenyl-4-yl]-1-(6-acryloyloxyhexyl)-r-1-cyclohexylcarbonitrile c-4-[4'-propyl-1,1'-biphenyl-4-yl]-1-(6-acryloyloxyhexyl)-r-1-cyclohexylcarbonitrile c-4-[4'-butyl-1,1'-biphenyl-4-yl]-1-(6-acryloyloxyhexyl)-r-1-cyclohexylcarbonitrile c-4-[4'-pentyl-1,1'-biphenyl-4-yl]-1-(6-acryloyloxyhexyl)-r-1-cyclohexylcarbonitrile c-4-[4'-ethoxy-1,1'-biphenyl-4-yl]-1-(7-acryloyloxyheptyl)-r-1-cyclohexylcarbonitrile c-4-[4'-propoxy-1,1'-biphenyl-4-yl]-1-(7-acryloyloxyheptyl)-r-1-cyclohexylcarbonitrile c-4-[4'-butoxy-1,1'-biphenyl-4-yl]-1-(7-acryloyloxyheptyl)-r-1-cyclohexylcarbonitrile c-4-[4'-pentyloxy-1,1'-biphenyl-4-yl]-1-(7-acryloyloxyheptyl)-r-1-cyclohexylcarbonitrile c-4-[4'-hexyloxy-1,1'-biphenyl-4-yl]-1-(7-acryloyloxyheptyl)-r-1-cyclohexylcarbonitrile c-4-[4'-heptyloxy-1,1'-biphenyl-4-yl]-1-(7-acryloyloxyheptyl)-r-1-cyclohexylcarbonitrile c-4-[4'-octyloxy-1,1'-biphenyl-4-yl]-1-(7-acryloyloxyheptyl)-r-1-cyclohexylcarbonitrile c-4-[4'-ethyl-1,1'-biphenyl-4-yl]-1-(7-acryloyloxyheptyl)-r-1-cyclohexylcarbonitrile c-4-[4'-propyl-1,1'-biphenyl-4-yl]-1-(7-acryloyloxyheptyl)-r-1-cyclohexylcarbonitrile c-4-[4'-butyl-1,1'-biphenyl-4-yl]-1-(7-acryloyloxyheptyl)-r-1-cyclohexylcarbonitrile c-4-[4'-pentyl-1,1'-biphenyl-4-yl]-1-(7-acryloyloxyheptyl)-r-1-cyclohexylcarbonitrile c-4-[4'-ethoxy-1,1'-biphenyl-4-yl]-1-(8-acryloyloxyoctyl)-r-1-cyclohexylcarbonitrile c-4-[4'-propoxy-1,1'-biphenyl-4-yl]-1-(8-acryloyloxyoctyl)-r-1-cyclohexylcarbonitrile c-4-[4'-butoxy-1,1'-biphenyl-4-yl]-1-(8-acryloyloxyoctyl)-r-1-cyclohexylcarbonitrile c-4-[4'-pentyloxy-1,1'-biphenyl-4-yl]-1-(8-acryloyloxyoctyl)-r-1-cyclohexylcarbonitrile c-4-[4'-hexyloxy-1,1'-biphenyl-4-yl]-1-(8-acryloyloxyoctyl)-r-1-cyclohexylcarbonitrile c-4-[4'-heptyloxy-1,1'-biphenyl-4-yl]-1-(8-acryloyloxyoctyl)-r-1-cyclohexylcarbonitrile c-4-[4'-octyloxy-1,1'-biphenyl-4-yl]-1-(8-acryloyloxyoctyl)-r-1-cyclohexylcarbonitrile
c-4-[4'-ethyl-1,1'-biphenyl-4-yl]-1-(8-acryloyloxyoctyl)-r-1-cyclohexylcarbonitrile
c-4-[4'-propyl-1,1'-biphenyl-4-yl]-1-(8-acryloyloxyoctyl)-r-1-cyclohexylcarbonitrile
c-4-[4'-butyl-1,1'-biphenyl-4-yl]-1-(8-acryloyloxyoctyl)-r-1-cyclohexylcarbonitrile
c-4-[4'-pentyl-1,1'-biphenyl-4-yl]-1-(8-acryloyloxyoctyl)-r-1-cyclohexylcarbonitrile
c-4-[4'-ethoxy-1,1'-biphenyl-4-yl]-1-(9-acryloyloxynonyl)-r-1-cyclohexylcarbonitrile
c-4-[4'-propoxy-1,1'-biphenyl-4-yl]-1-(9-acryloyloxynonyl)-r-1-cyclohexylcarbonitrile
c-4-[4'-butoxy-1,1'-biphenyl-4-yl]-1-(9-acryloyloxynonyl)-r-1-cyclohexylcarbonitrile
c-4-[4'-pentyloxy-1,1'-biphenyl-4-yl]-1-(9-acryloyloxynonyl)-r-1-cyclohexylcarbonitrile
c-4-[4'-hexyloxy-1,1'-biphenyl-4-yl]-1-(9-acryloyloxynonyl)-r-1-cyclohexylcarbonitrile
c-4-[4'-heptyloxy-1,1'-biphenyl-4-yl]-1-(9-acryloyloxynonyl)-r-1-cyclohexylcarbonitrile
c-4-[4'-octyloxy-1,1'-biphenyl-4-yl]-1-(9-acryloyloxynonyl)-r-1-cyclohexylcarbonitrile
c-4-[4'-ethyl-1,1'-biphenyl-4-yl]-1-(9-acryloyloxynonyl)-r-1-cyclohexylcarbonitrile
c-4-[4'-propyl-1,1'-biphenyl-4-yl]-1-(9-acryloyloxynonyl)-r-1-cyclohexylcarbonitrile
c-4-[4'-butyl-1,1'-biphenyl-4-yl]-1-(9-acryloyloxynonyl)-r-1-cyclohexylcarbonitrile
c-4-[4'-pentyl-1,1'-biphenyl-4-yl]-1-(9-acryloyloxynonyl)-r-1-cyclohexylcarbonitrile
c-4-[4'-ethoxy-1,1'-biphenyl-4-yl]-1-(10-acryloyloxydecyl)-r-1-cyclohexylcarbonitrile
c-4-[4'-propoxy-1,1'-biphenyl-4-yl]-1-(10-acryloyloxydecyl)-r-1-cyclohexylcarbonitrile
c-4-[4'-butoxy-1,1'-biphenyl-4-yl]-1-(10-acryloyloxydecyl)-r-1-cyclohexylcarbonitrile
c-4-[4'-pentyloxy-1,1'-biphenyl-4-yl]-1-(10-acryloyloxydecyl)-r-1-cyclohexylcarbonitrile
c-4-[4'-hexyloxy-1,1'-biphenyl-4-yl]-1-(10-acryloyloxydecyl)-r-1-cyclohexylcarbonitrile
c-4-[4'-heptyloxy-1,1'-biphenyl-4-yl]-1-(10-acryloyloxydecyl)-r-1-cyclohexylcarbonitrile
c-4-[4'-octyloxy-1,1'-biphenyl-4-yl]-1-(10-acryloyloxydecyl)-r-1-cyclohexylcarbonitrile
c-4-[4'-ethyl-1,1'-biphenyl-4-yl]-1-(10-acryloyloxydecyl)-r-1-cyclohexylcarbonitrile
c-4-[4'-propyl-1,1'-biphenyl-4-yl]-1-(10-acryloyloxydecyl)-r-1-cyclohexylcarbonitrile
c-4-[4'-butyl-1,1'-biphenyl-4-yl]-1-(10-acryloyloxydecyl)-r-1-cyclohexylcarbonitrile
c-4-[4'-pentyl-1,1'-biphenyl-4-yl]-1-(10-acryloyloxydecyl)-r-1-cyclohexylcarbonitrile
c-4-[4'-ethoxy-1,1'-biphenyl-4-yl]-1-(11-acryloyloxyundecyl)-r-1-cyclohexylcarbonitrile
c-4-[4'-propoxy-1,1'-biphenyl-4-yl]-1-(11-acryloyloxyundecyl)-r-1-cyclohexylcarbonitrile
c-4-[4'-butoxy-1,1'-biphenyl-4-yl]-1-(11-acryloyloxyundecyl)-r-1-cyclohexylcarbonitrile
c-4-[4'-pentyloxy-1,1'-biphenyl-4-yl]-1-(11-acryloyloxyundecyl)-r-1-cyclohexylcarbonitrile
c-4-[4'-hexyloxy-1,1'-biphenyl-4-yl]-1-(11-acryloyloxyundecyl)-r-1-cyclohexylcarbonitrile
c-4-[4'-heptyloxy-1,1'-biphenyl-4-yl]-1-(11-acryloyloxyundecyl)-r-1-cyclohexylcarbonitrile
c-4-[4'-octyloxy-1,1'-biphenyl-4-yl]-1-(11-acryloyloxyundecyl)-r-1-cyclohexylcarbonitrile
c-4-[4'-ethyl-1,1'-biphenyl-4-yl]-1-(11-acryloyloxyundecyl)-r-1-cyclohexylcarbonitrile
c-4-[4'-propyl-1,1'-biphenyl-4-yl]-1-(11-acryloyloxyundecyl)-r-1-cyclohexylcarbonitrile
c-4-[4'-butyl-1,1'-biphenyl-4-yl]-1-(11-acryloyloxyundecyl)-r-1-cyclohexylcarbonitrile
c-4-[4'-pentyl-1,1'-biphenyl-4-yl]-1-(11-acryloyloxyundecyl)-r-1-cyclohexylcarbonitrile
c-4-[4'-(2-methylbutoxy)-1,1'-biphenyl-4-yl]-1-(11-acryloylundecyl)-r-1-cyclohexylcarbonitrile, optically active
c-4-[4'-(2-methylbutoxy)-1,1'-biphenyl-4-yl]-1-(10-acryloyloxydecyl)-r-1-cyclohexylcarbonitrile, optically active
c-4-[4'-(2-methylbutoxy)-1,1'-biphenyl-4-yl]-1-(9-acryloyloxynonyl)-r-1-cyclohexylcarbonitrile, optically active
c-4-[4'-(2-methylbutoxy)-1,1'-biphenyl-4-yl]-1-(8-acryloyloxyoctyl)-r-1-cyclohexylcarbonitrile, optically active
c-4-[4'-(2-methylbutoxy)-1,1'-biphenyl-4-yl]-1-(7-acryloyloxyheptyl)-r-1-cyclohexylcarbonitrile, optically active
c-4-[4'-(2-octyloxy)-1,1'-biphenyl-4-yl]-1-(11-acryloyloxyundecyl)-r-1-cyclohexylcarbonitrile, optically active
c-4-[4'-(2-octyloxy)-1,1'-biphenyl-4-yl]-1-(10-acryloyloxydecyl)-r-1-cyclohexylcarbonitrile, optically active
c-4-[4'-(2-octyloxy)-1,1'-biphenyl-4-yl]-1-(9-acryloyloxynonyl)-r-1-cyclohexylcarbonitrile, optically active
c-4-[4'-(2-octyloxy)-1,1'-biphenyl-4-yl]-1-(8-acryloyloxyoctyl)-r-1-cyclohexylcarbonitrile, optically active
c-4-[4'-(2-octyloxy)-1,1'-biphenyl-4-yl]-1-(7-acryloyloxyheptyl)-r-1-cyclohexylcarbonitrile, optically active

EXAMPLE 8

A mixture of 3.0 g of r-1-cyano-c-4-(4'-hydroxy-1,1'-biphenyl-4-yl)-1-octylcyclohexane, 2.0 g of 11-bromoundecanol, 0.7 g of potassium hydroxide, 2 mg of potassium iodide and 60 ml of ethanol is heated at the boil for 3 days. The reaction mixture is evaporated, the residue is suspended in 100 ml of H$_2$O, the suspension is filtered and the residue is recrystallized to give c-4-[4'-(11-hydroxyundecyloxy)-1,1'-biphenyl-4-yl]-1-octyl-r-1-cyclohexylcarbonitrile.

The following are prepared analogously:
c-4-[4'-(3-hydroxypropoxy)-1,1'-biphenyl-4-yl]-1-octyl-r-1-cyclohexylcarbonitrile
c-4-[4'-(4-hydroxybutoxy)-1,1'-biphenyl-4-yl]-1-octyl-r-1-cyclohexylcarbonitrile
c-4-[4'-(5-hydroxypentyloxy)-1,1'-biphenyl-4-yl]-1-octyl-r-1-cyclohexylcarbonitrile
c-4-[4'-(6-hydroxyhexyloxy)-1,1'-biphenyl-4-yl]-1-octyl-r-1-cyclohexylcarbonitrile
c-4-[4'-(7-hydroxyheptyloxy)-1,1'-biphenyl-4-yl]-1-octyl-r-1-cyclohexylcarbonitrile
c-4-[4'-(8-hydroxyoctyloxy)-1,1'-biphenyl-4-yl]-1-octyl-r-1-cyclohexylcarbonitrile
c-4-[4'-(9-hydroxynonyloxy)-1,1'-biphenyl-4-yl]-1-octyl-r-1-cyclohexylcarbonitrile
c-4-[4'-(10-hydroxydecyloxy)-1,1'-biphenyl-4-yl]-1-octyl-r-1-cyclohexylcarbonitrile
c-4-[4'-(5-hydroxypentoxy)-1,1'-biphenyl-4-yl]-1-heptyl-r-1-cyclohexylcarbonitrile
c-4-[4'-(6-hydroxyhexyloxy)-1,1'-biphenyl-4-yl]-1-heptyl-r-1-cyclohexylcarbonitrile c-4-[4'-(7-hydroxyheptyloxy)-1,1'-biphenyl-4-yl]-1-heptyl-r-1-cyclohexylcarbonitrile
c-4-[4'-(8-hydroxyoctyloxy)-1,1'-biphenyl-4-yl]-1-heptyl-r-1-cyclohexylcarbonitrile
c-4-[4'-(9-hydroxynonyloxy)-1,1'-biphenyl-4-yl]-1-heptyl-r-1-cyclohexylcarbonitrile
c-4-[4'-(10-hydroxydecyloxy)-1,1'-biphenyl-4-yl]-1-heptyl-r-1-cyclohexylcarbonitrile
c-4-[4'-(11-hydroxyundecyloxy)-1,1'-biphenyl-4-yl]-1-heptyl-r-1-cyclohexylcarbonitrile
c-4-[4'-(6-hydroxyhexyloxy)-1,1'-biphenyl-4-yl]-1-hexyl-r-1-cyclohexylcarbonitrile
c-4-[4'-(7-hydroxyheptyloxy)-1,1'-biphenyl-4-yl]-1-hexyl-r-1-cyclohexylcarbonitrile
c-4-[4'-(8-hydroxyoctyloxy)-1,1'-biphenyl-4-yl]-1-hexyl-r-1-cyclohexylcarbonitrile
c-4-[4'-(9-hydroxynonyloxy)-1,1'-biphenyl-4-yl]-1-hexyl-r-1-cyclohexylcarbonitrile
c-4-[4'-(10-hydroxydecyloxy)-1,1'-biphenyl-4-yl]-1-hexyl-r-1-cyclohexylcarbonitrile
c-4-[4'-(11-hydroxyundecyloxy)-1,1'-biphenyl-4-yl]-1-hexyl-r-1-cyclohexylcarbonitrile

EXAMPLE 9

A mixture of 2.3 g of c-4-[4'-11-hydroxyundecyloxy)-1,1'-biphenyl-4-yl]-1-octyl-r-1-cyclohexylcarbonitrile, 4.8 g of methacrylic acid, 0.2 g of hydroquinone, 0.2 g of p-toluenesulfonic acid monohydrate and 60 ml of chloroform is heated under a water separator for 3 days. The reaction solution is washed, dried and evaporated. Chromatographing the residue over silica gel using 98:2 dichloromethane/methanol gives c-4-[4'-(11-methacryloyloxyundecyloxy)-1,1'-biphenyl-4-yl]-1-octyl-r-1-cyclohexylcarbonitrile of K 49°, $S_C$ 71°, $S_A$ 106°, N 108° I.

The following are prepared analogously:
c-4-[4'-(3-methacryloyloxypropoxy)-1,1'-biphenyl-4-yl]-1-octyl-r-1-cyclohexylcarbonitrile
c-4-[4'-(4-methacryloyloxybutoxy)-1,1'-biphenyl-4-yl]-1-octyl-r-1-cyclohexylcarbonitrile
c-4-[4'-(5-methacryloyloxypentyloxy)-1,1'-biphenyl-4-yl]-1-octyl-r-1-cyclohexylcarbonitrile
c-4-[4'-(6-methacryloyloxyhexyloxy)-1,1'-biphenyl-4-yl]-1-octyl-r-1-cyclohexylcarbonitrile
c-4-[4'-(7-methacryloyloxyheptyloxy)-1,1'-biphenyl-4-yl]-1-octyl-r-1-cyclohexylcarbonitrile
c-4-[4'-(8-methacryloyloxyoctyloxy)-1,1'-biphenyl-4-yl]-1-octyl-r-1-cyclohexylcarbonitrile
c-4-[4'-(9-methacryloyloxynonyloxy)-1,1'-biphenyl-4-yl]-1-octyl-r-1-cyclohexylcarbonitrile
c-4-[4'-(10-methacryloyloxydecyloxy)-1,1'-biphenyl-4-yl]-1-octyl-r-1-cyclohexylcarbonitrile
c-4-[4'-(5-methacryloyloxypentoxy)-1,1'-biphenyl-4-yl]-1-heptyl-r-1-cyclohexylcarbonitrile
c-4-[4'-(6-methacryloyloxyhexyloxy)-1,1'-biphenyl-4-yl]-1-heptyl-r-1-cyclohexylcarbonitrile
c-4-[4'-(7-methacryloyloxyheptyloxy)-1,1'-biphenyl-4-yl]-1-heptyl-r-1-cyclohexylcarbonitrile
c-4-[4'-(8-methacryloyloxyoctyloxy)-1,1'-biphenyl-4-yl]-1-heptyl-r-1-cyclohexylcarbonitrile
c-4-[4'-(9-methacryloyloxynonyloxy)-1,1'-biphenyl-4-yl]-1-heptyl-r-1-cyclohexylcarbonitrile
c-4-[4'-(10-methacryloyloxydecyloxy)-1,1'-biphenyl-4-yl]-1-heptyl-r-1-cyclohexylcarbonitrile
c-4-[4'-(11-methacryloyloxyundecyloxy)-1,1'-biphenyl-4-yl]-1-heptyl-r-1-cyclohexylcarbonitrile
c-4-[4'-(5-methacryloyloxypentoxy)-1,1'-biphenyl-4-yl]-1-hexyl-r-1-cyclohexylcarbonitrile
c-4-[4'-(6-methacryloyloxyhexyloxy)-1,1'-biphenyl-4-yl]-1-hexyl-r-1-cyclohexylcarbonitrile
c-4-[4'-(7-methacryloyloxyheptyloxy)-1,1'-biphenyl-4-yl]-1-hexyl-r-1-cyclohexylcarbonitrile
c-4-[4'-(8-methacryloyloxyoctyloxy)-1,1'-biphenyl-4-yl]-1-hexyl-r-1-cyclohexylcarbonitrile
c-4-[4'-(9-methacryloyloxynonyloxy)-1,1'-biphenyl-4-yl]-1-hexyl-r-1-cyclohexylcarbonitrile
c-4-[4'-(10-methacryloyloxydecyloxy)-1,1'-biphenyl-4-yl]-1-hexyl-r-1-cyclohexylcarbonitrile
c-4-[4'-(11-methacryloyloxyundecyloxy)-1,1'-biphenyl-4-yl]-1-hexyl-r-1-cyclohexylcarbonitrile

EXAMPLE 10

The corresponding c-4-[4'-(11-acryloyloxyundecyloxy)-1,1'-biphenyl-4-yl]-1-octyl-r-1-cyclohexylcarbonitrile is obtained analogously to Example 9 by reacting c-4-[4'-(11-hydroxyundecyloxy)-1,1'-biphenyl-4-yl]-1-octyl-r-1-cyclohexylcarbonitrile with acrylic acid.

The following are prepared analogously:
c-4-[4'-(3-acryloyloxypropoxy)-1,1'-biphenyl-4-yl]-1-octyl-r-1-cyclohexylcarbonitrile
c-4-[4'-(4-acryloyloxybutoxy)-1,1'-biphenyl-4-yl]-1-octyl-r-1-cyclohexylcarbonitrile
c-4-[4'-(5-acryloyloxypentyloxy)-1,1'-biphenyl-4-yl]-1-octyl-r-1-cyclohexylcarbonitrile
c-4-[4'-(6-acryloyloxyhexyloxy)-1,1'-biphenyl-4-yl]-1-octyl-r-1-cyclohexylcarbonitrile
c-4-[4'-(7-acryloyloxyheptyloxy)-1,1'-biphenyl-4-yl]-1-octyl-r-1-cyclohexylcarbonitrile
c-4-[4'-(8-acryloyloxyoctyloxy)-1,1'-biphenyl-4-yl]-1-octyl-r-1-cyclohexylcarbonitrile
c-4-[4'-(9-acryloyloxynonyloxy)-1,1'-biphenyl-4-yl]-1-octyl-r-1-cyclohexylcarbonitrile
c-4-[4'-(10-acryloyloxydecyloxy)-1,1'-biphenyl-4-yl]-1-octyl-r-1-cyclohexylcarbonitrile
c-4-[4'-(5-acryloyloxypentyloxy)-1,1'-biphenyl-4-yl]-1-heptyl-r-1-cyclohexylcarbonitrile
c-4-[4'-(6-acryloyloxyhexyloxy)-1,1'-biphenyl-4-yl]-1-heptyl-r-1-cyclohexylcarbonitrile
c-4-[4'-(7-acryloyloxyheptyloxy)-1,1'-biphenyl-4-yl]-1-heptyl-r-1-cyclohexylcarbonitrile
c-4-[4'-(8-acryloyloxyoctyloxy)-1,1'-biphenyl-4-yl]-1-heptyl-r-1-cyclohexylcarbonitrile
c-4-[4'-(9-acryloyloxynonyloxy)-1,1'-biphenyl-4-yl]-1-heptyl-r-1-cyclohexylcarbonitrile
c-4-[4'-(10-acryloyloxydecyloxy)-1,1'-biphenyl-4-yl]-1-heptyl-r-1-cyclohexylcarbonitrile
c-4-[4'-(11-acryloyloxyundecyloxy)-1,1'-biphenyl-4-yl]-1-heptyl-r-1-cyclohexylcarbonitrile
c-4-[4'-(6-acryloyloxyhexyloxy)-1,1'-biphenyl-4-yl]-1-pentyl-r-1-cyclohexylcarbonitrile
c-4-[4'-(7-acryloyloxyheptyloxy)-1,1'-biphenyl-4-yl]-1-pentyl-r-1-cyclohexylcarbonitrile
c-4-[4'-(8-acryloyloxyoctyloxy)-1,1'-biphenyl-4-yl]-1-pentyl-r-1-cyclohexylcarbonitrile
c-4-[4'-(9-acryloyloxynonyloxy)-1,1'-biphenyl-4-yl]-1-pentyl-r-1-cyclohexylcarbonitrile
c-4-[4'-(10-acryloyloxydecyloxy)-1,1'-biphenyl-4-yl]-1-pentyl-r-1-cyclohexylcarbonitrile
c-4-[4'-(11-acryloyloxyundecyloxy)-1,1'-biphenyl-4-yl]-1-pentyl-r-1-cyclohexylcarbonitrile

EXAMPLE 11 a) 275 ml of a 1.6 molar solution of n-butyllithium in hexane are added at 0° to a solution of 46.5 g of diisopropylamine in 400 ml of THF. This solution is then added at −70° C. to a mixture of 30.6 g of 4-cyanocyclohexylcarboxylic acid in THF, the mixture is stirred for 2 hours, 39.1 g of 1-bromo-5-hexene are then added and the mixture is allowed to warm up to 0°. 35 ml of ethanol are added, the mixture is poured onto ice and extracted with tert.-butyl methyl ether, and the aqueous phase is acidified with 2N HCl and extracted again. The organic phase is worked up to give, after recrystallization from ethanol, c-4-cyano-t-4-(5-hexenyl)-r-1-cyclohexylcarboxylic acid.

b) A solution of 14.8 g of DCCI in 10 ml of CH$_2$Cl$_2$ is added at 0° to a mixture of 16.5 g of the carboxylic acid obtained under a), 20.9 g of 4-hydroxy-4'-octyloxy-1,1'-biphenyl, 855 mg of 4-dimethylaminopyridine and 80 ml of CH$_2$Cl$_2$, and the mixture is stirred for 18 hours at room temperature. The precipitate is removed and the filtrate is worked up to give, after recrystallization, 4'-octyloxy-1,1'-biphenyl-4-yl c-4-cyano-t-(5-hexenyl)-r-1-cyclohexylcarboxylate.

The following are prepared analogously:
4'-heptyloxy-1,1'-biphenyl-4-yl c-4-cyano-t-4-(5-hexenyl)-r-1-cyclohexylcarboxylate
4'-hexyloxy-1,1'-biphenyl-4-yl c-4-cyano-t-4-(5-hexenyl)-r-1-cyclohexylcarboxylate
4'-pentyloxy-1,1'-biphenyl-4-yl c-4-cyano-t-4-(5-hexenyl)-r-1-cyclohexylcarboxylate
4'-butoxy-1,1'-biphenyl-4-yl c-4-cyano-t-4-(5-hexenyl)-r-1-cyclohexylcarboxylate
4'-propoxy-1,1'-biphenyl-4-yl. c-4-cyano-t-4-(5-hexenyl)-r-1-cyclohexylcarboxylate
4'-pentyl-1,1'-biphenyl-4-yl c-4-cyano-t-4-(5-hexenyl)-r-1-cyclohexylcarboxylate
4'-hexyl-1,1'-biphenyl-4-yl c-4-cyano-t-4-(5-hexenyl)-r-1-cyclohexylcarboxylate
4'-heptyl-1,1'-biphenyl-4-yl c-4-cyano-t-4-(5-hexenyl)-r-1-cyclohexylcarboxylate
4'-octyloxy-1,1'-biphenyl-4-yl c-4-cyano-t-4-(6-heptenyl)-r-1-cyclohexylcarboxylate
4'-heptyloxy-1,1'-biphenyl-4-yl c-4-cyano-t-4-(6-heptenyl)-r-1-cyclohexylcarboxylate
4'-hexyloxy-1,1'-biphenyl-4-yl c-4-cyano-t-4-(6-heptenyl)-r-1-cyclohexylcarboxylate
4'-pentyloxy-1,1'-biphenyl-4-yl c-4-cyano-t-4-(6-heptenyl)-r-1-cyclohexylcarboxylate
4'-butoxy-1,1'-biphenyl-4-yl c-4-cyano-t-4-(6-heptenyl)-r-1-cyclohexylcarboxylate
4'-propoxy-1,1'-biphenyl-4-yl c-4-cyano-t-4-(6-heptenyl)-r-1-cyclohexylcarboxylate
4'-pentyl-1,1'-biphenyl-4-yl c-4-cyano-t-4-(6-heptenyl)-r-1-cyclohexylcarboxylate
4'-hexyl-1,1'-biphenyl-4-yl c-4-cyano-t-4-(6-heptenyl)-r-1-cyclohexylcarboxylate
4'-heptyl-1,1'-biphenyl-4-yl c-4-cyano-t-4-(6-heptenyl)-r-1-cyclohexylcarboxylate
4'-octyloxy-1,1'-biphenyl-4-yl c-4-cyano-t-4-(7-octenyl)-r-1-cyclohexylcarboxylate
4'-heptyloxy-1,1'-biphenyl-4-yl c-4-cyano-t-4-(7-octenyl)-r-1-cyclohexylcarboxylate
4'-hexyloxy-1,1'-biphenyl-4-yl c-4-cyano-t-4-(7-octenyl)-r-1-cyclohexylcarboxylate
4'-pentyloxy-1,1'-biphenyl-4-yl c-4-cyano-t-4-(7-octenyl)-r-1-cyclohexylcarboxylate
4'-butoxy-1,1'-biphenyl-4-yl c-4-cyano-t-4-(7-octenyl)-r-1-cyclohexylcarboxylate
4'-propoxy-1,1'-biphenyl-4-yl c-4-cyano-t-4-(7-octenyl)-r-1-cyclohexylcarboxylate
4'-pentyl-1,1'-biphenyl-4-yl c-4-cyano-t-4-(7-octenyl)-r-1-cyclohexylcarboxylate
4'-hexyl-1,1'-biphenyl-4-yl c-4-cyano-t-4-(7-octenyl)-r-1-cyclohexylcarboxylate
4'-heptyl-1,1'-biphenyl-4-yl c-4-cyano-t-4-(7-octenyl)-r-1-cyclohexylcarboxylate
4'-octyloxy-1,1'-biphenyl-4-yl c-4-cyano-t-4-(8-nonenyl)-r-1-cyclohexylcarboxylate
4'-heptyloxy-1,1'-biphenyl-4-yl c-4-cyano-t-4-(8-nonenyl)-r-1-cyclohexylcarboxylate
4'-hexyloxy-1,1'-biphenyl-4-yl c-4-cyano-t-4-(8-nonenyl)-r-1-cyclohexylcarboxylate
4'-pentyloxy-1,1'-biphenyl-4-yl c-4-cyano-t-4-(8-nonenyl)-r-1-cyclohexylcarboxylate
4'-butoxy-1,1'-biphenyl-4-yl c-4-cyano-t-4-(8-nonenyl)-r-1-cyclohexylcarboxylate
4'-propoxy-1,1'-biphenyl-4-yl c-4-cyano-t-4-(8-nonenyl)-r-1-cyclohexylcarboxylate
4'-pentyl-1,1'-biphenyl-4-yl c-4-cyano-t-4-(8-nonenyl)-r-1-cyclohexylcarboxylate
4'-hexyl-1,1'-biphenyl-4-yl c-4-cyano-t-4-(8-nonenyl)-r-1-cyclohexylcarboxylate
4'-heptyl-1,1'-biphenyl-4-yl c-4-cyano-t-4-(8-nonenyl)-r-1-cyclohexylcarboxylate
4'-octyloxy-1,1'-biphenyl-4-yl c-4-cyano-t-4-(9-decenyl)-r-1-cyclohexylcarboxylate
4'-heptyloxy-1,1'-biphenyl-4-yl c-4-cyano-t-4-(9-decenyl)-r-1-cyclohexylcarboxylate
4'-hexyloxy-1,1'-biphenyl-4-yl c-4-cyano-t-4-(9-decenyl)-r-1-cyclohexylcarboxylate
4'-pentyloxy-1,1'-biphenyl-4-yl c-4-cyano-t-4-(9-decenyl)-r-1-cyclohexylcarboxylate
4'-butoxy-1,1'-biphenyl-4-yl c-4-cyano-t-4-(9-decenyl)-r-1-cyclohexylcarboxylate
4'-propoxy-1,1'-biphenyl-4-yl c-4-cyano-t-4-(9-decenyl)-r-1-cyclohexylcarboxylate
4'-pentyl-1,1'-biphenyl-4-yl c-4-cyano-t-4-(9-decenyl)-r-1-cyclohexylcarboxylate
4'-hexyl-1,1'-biphenyl-4-yl c-4-cyano-t-4-(9-decenyl)-r-1-cyclohexylcarboxylate
4'-heptyl-1,1'-biphenyl-4-yl c-4-cyano-t-4-(9-decenyl)-r-1-cyclohexylcarboxylate
4'-octyloxy-1,1'-biphenyl-4-yl c-4-cyano-t-4-(10-undecenyl)-r-1-cyclohexylcarboxylate
4'-heptyloxy-1,1'-biphenyl-4-yl c-4-cyano-t-4-(10-undecenyl)-r-1-cyclohexylcarboxylate
4'-hexyloxy-1,1'-biphenyl-4-yl c-4-cyano-t-4-(10-undecenyl)-r-1-cyclohexylcarboxylate
4'-pentyloxy-1,1'-biphenyl-4-yl c-4-cyano-t-4-(10-undecenyl)-r-1-cyclohexylcarboxylate
4'-butoxy-1,1'-biphenyl-4-yl c-4-cyano-t-4-(10-undecenyl)-r-1-cyclohexylcarboxylate
4'-propoxy-1,1'-biphenyl-4-yl c-4-cyano-t-4-(10-undecenyl)-r-1-cyclohexylcarboxylate
4'-pentyl-1,1'-biphenyl-4-yl c-4-cyano-t-4-(10-undecenyl)-r-1-cyclohexylcarboxylate
4'-hexyl-1,1'-biphenyl-4-yl c-4-cyano-t-4-(10-undecenyl)-r-1-cyclohexylcarboxylate
4'-heptyl-1,1'-biphenyl-4-yl c-4-cyano-t-4-(10-undecenyl)-r-1-cyclohexylcarboxylate

EXAMPLE 12

The corresponding alcohol 4'-octyloxy-1,1'-biphenyl-4-yl c-4-cyano-t-4-(6-hydroxyhexyl)-r-1-cyclohexylcarboxylate is obtained analogously to Example 5b) from 4'-octyloxy-1,1'-biphenyl-4-yl c-4-cyano-t-4-hexen-5-yl-r-1-cyclohexylcarboxylate.

The following are prepared analogously:
4'-heptyloxy-1,1'-biphenyl-4-yl c-4-cyano-t-4-(6-hydroxyhexyl)-r-1-cyclohexylcarboxylate 4'-hexyloxy-1,1'-biphenyl-4-yl c-4-cyano-t-4-(6-hydroxyhexyl)-r-1-cyclohexylcarboxylate
4'-pentyloxy-1,1'-biphenyl-4-yl c-4-cyano-t-4-(6-hydroxyhexyl)-r-1-cyclohexylcarboxylate
4'-butoxy-1,1'-biphenyl-4-yl c-4-cyano-t-4-(6-hydroxyhexyl)-r-1-cyclohexylcarboxylate
4'-propoxy-1,1'-biphenyl-4-yl c-4-cyano-t-4-(6-hydroxyhexyl)-r-1-cyclohexylcarboxylate
4'-pentyl-1,1'-biphenyl-4-yl c-4-cyano-t-4-(6-hydroxyhexyl)-r-1-cyclohexylcarboxylate
4'-hexyl-1,1'-biphenyl-4-yl c-4-cyano-t-4-(6-hydroxyhexyl)-r-1-cyclohexylcarboxylate
4'-heptyl-1,1'-biphenyl-4-yl c-4-cyano-t-4-(6-hydroxyhexyl)-r-1-cyclohexylcarboxylate
4'-octyloxy-1,1'-biphenyl-4-yl c-4-cyano-t-4-(7-hydroxyheptyl)-r-1-cyclohexylcarboxylate
4'-heptyloxy-1,1'-biphenyl-4-yl c-4-cyano-t-4-(7-hydroxyheptyl)-r-1-cyclohexylcarboxylate
4'-hexyloxy-1,1'-biphenyl-4-yl c-4-cyano-t-4-(7-hydroxyheptyl)-r-1-cyclohexylcarboxylate
4'-pentyloxy-1,1'-biphenyl-4-yl c-4-cyano-t-4-(7-hydroxyheptyl)-r-1-cyclohexylcarboxylate
4'-butoxy-1,1'-biphenyl-4-yl c-4-cyano-t-4-(7-hydroxyheptyl)-r-1-cyclohexylcarboxylate
4'-propoxy-1,1'-biphenyl-4-yl c-4-cyano-t-4-(7-hydroxyheptyl)-r-1-cyclohexylcarboxylate
4'-pentyl-1,1'-biphenyl-4-yl c-4-cyano-t-4-(7-hydroxyheptyl)-r-1-cyclohexylcarboxylate
4'-hexyl-1,1'-biphenyl-4-yl c-4-cyano-t-4-(7-hydroxyheptyl)-r-1-cyclohexylcarboxylate
4'-heptyl-1,1'-biphenyl-4-yl c-4-cyano-t-4-(7-hydroxyheptyl)-r-1-cyclohexylcarboxylate
4'-octyloxy-1,1'-biphenyl-4-yl c-4-cyano-t-4-(8-hydroxyoctyl)-r-1-cyclohexylcarboxylate
4'-heptyloxy-1,1'-biphenyl-4-yl c-4-cyano-t-4-(8-hydroxyoctyl)-r-1-cyclohexylcarboxylate
4'-hexyloxy-1,1'-biphenyl-4-yl c-4-cyano-t-4-(8-hydroxyoctyl)-r-1-cyclohexylcarboxylate
4'-pentyloxy-1,1'-biphenyl-4-yl c-4-cyano-t-4-(8-hydroxyoctyl)-r-1-cyclohexylcarboxylate
4'-butoxy-1,1'-biphenyl-4-yl c-4-cyano-t-4-(8-hydroxyoctyl)-r-1-cyclohexylcarboxylate
4'-propoxy-1,1'-biphenyl-4-yl c-4-cyano-t-4-(8-hydroxyoctyl)-r-1-cyclohexylcarboxylate
4'-pentyl-1,1'-biphenyl-4-yl c-4-cyano-t-4-(8-hydroxyoctyl)-r-1-cyclohexylcarboxylate
4'-hexyl-1,1'-biphenyl-4-yl c-4-cyano-t-4-(8-hydroxyoctyl)-r-1-cyclohexylcarboxylate
4'-heptyl-1,1'-biphenyl-4-yl c-4-cyano-t-4-(8-hydroxyoctyl)-r-1-cyclohexylcarboxylate
4'-octyloxy-1,1'-biphenyl-4-yl c-4-cyano-t-4-(9-hydroxynonyl)-r-1-cyclohexylcarboxylate
4'-heptyloxy-1,1'-biphenyl-4-yl c-4-cyano-t-4-(9-hydroxynonyl)-r-1-cyclohexylcarboxylate
4'-hexyloxy-1,1'-biphenyl-4-yl c-4-cyano-t-4-(9-hydroxynonyl)-r-1-cyclohexylcarboxylate
4'-pentyloxy-1,1'-biphenyl-4-yl c-4-cyano-t-4-(9-hydroxynonyl)-r-1-cyclohexylcarboxylate
4'-butoxy-1,1'-biphenyl-4-yl c-4-cyano-t-4-(9-hydroxynonyl)-r-1-cyclohexylcarboxylate
4'-propoxy-1,1'-biphenyl-4-yl c-4-cyano-t-4-(9-hydroxynonyl)-r-1-cyclohexylcarboxylate
4'-pentyl-1,1'-biphenyl-4-yl c-4-cyano-t-4-(9-hydroxynonyl)-r-1-cyclohexylcarboxylate
4'-hexyl-1,1'-biphenyl-4-yl c-4-cyano-t-4-(9-hydroxynonyl)-r-1-cyclohexylcarboxylate
4'-heptyl-1,1'-biphenyl-4-yl c-4-cyano-t-4-(9-hydroxynonyl)-r-1-cyclohexylcarboxylate
4'-octyloxy-1,1'-biphenyl-4-yl c-4-cyano-t-4-(10-hydroxydecyl)-r-1-cyclohexylcarboxylate
4'-heptyloxy-1,1'-biphenyl-4-yl c-4-cyano-t-4-(10-hydroxydecyl)-r-1-cyclohexylcarboxylate
4'-hexyloxy-1,1'-biphenyl-4-yl c-4-cyano-t-4-(10-hydroxydecyl)-r-1-cyclohexylcarboxylate
4'-pentyloxy-1,1'-biphenyl-4-yl c-4-cyano-t-4-(10-hydroxydecyl)-r-1-cyclohexylcarboxylate
4'-butoxy-1,1'-biphenyl-4-yl c-4-cyano-t-4-(10-hydroxydecyl)-r-1-cyclohexylcarboxylate
4'-propoxy-1,1'-biphenyl-4-yl c-4-cyano-t-4-(10-hydroxydecyl)-r-1-cyclohexylcarboxylate
4'-pentyl-1,1'-biphenyl-4-yl c-4-cyano-t-4-(10-hydroxydecyl)-r-1-cyclohexylcarboxylate
4'-hexyl-1,1'-biphenyl-4-yl c-4-cyano-t-4-(10-hydroxydecyl)-r-1-cyclohexylcarboxylate
4'-heptyl-1,1'-biphenyl-4-yl c-4-cyano-t-4-(10-hydroxydecyl)-r-1-cyclohexylcarboxylate
4'-octyloxy-1,1'-biphenyl-4-yl c-4-cyano-t-4-(11-hydroxyundecyl)-r-1-cyclohexylcarboxylate
4'-heptyloxy-1,1'-biphenyl-4-yl c-4-cyano-t-4-(11-hydroxyundecyl)-r-1-cyclohexylcarboxylate
4'-hexyloxy-1,1'-biphenyl-4-yl c-4-cyano-t-4-(11-hydroxyundecyl)-r-1-cyclohexylcarboxylate
4'-pentyloxy-1,1'-biphenyl-4-yl c-4-cyano-t-4-(11-hydroxyundecyl)-r-1-cyclohexylcarboxylate
4'-butoxy-1,1'-biphenyl-4-yl c-4-cyano-t-4-(11-hydroxyundecyl)-r-1-cyclohexylcarboxylate
4'-propoxy-1,1'-biphenyl-4-yl c-4-cyano-t-4-(11-hydroxyundecyl)-r-1-cyclohexylcarboxylate
4'-pentyl-1,1'-biphenyl-4-yl c-4-cyano-t-4-(11-hydroxyundecyl)-r-1-cyclohexylcarboxylate
4'-hexyl-1,1'-biphenyl-4-yl c-4-cyano-t-4-(11-hydroxyundecyl)-r-1-cyclohexylcarboxylate
4'-heptyl-1,1'-biphenyl-4-yl c-4-cyano-t-4-(11-hydroxyundecyl)-r-1-cyclohexylcarboxylate

EXAMPLE 13

The corresponding 4'-octyloxy-1,1'-biphenyl-4-yl c-4-cyano-t-4-(6-methacryloyloxyhexyl)-r-1-cyclohexylcarboxylate is obtained analogously to Example 6 by reacting 4'-octyloxy-1,1'-biphenyl-4-yl c-4-cyano-t-4-(6-hydroxyhexyl)-r-1-cyclohexylcarboxylate with methacrylic acid in the presence of DCCI.

The following are prepared analogously:
4'-heptyloxy-1,1'-biphenyl-4-yl c-4-cyano-t-4-(6-methacryloyloxyhexyl)-r-1-cyclohexylcarboxylate
4'-hexyloxy-1,1'-biphenyl-4-yl c-4-cyano-t-4-(6-methacryloyloxyhexyl)-r-1-cyclohexylcarboxylate
4'-pentyloxy-1,1'-biphenyl-4-yl c-4-cyano-t-4-(6-methacryloyloxyhexyl)-r-1-cyclohexylcarboxylate
4'-butoxy-1,1'-biphenyl-4-yl c-4-cyano-t-4-(6-methacryloyloxyhexyl)-r-1-cyclohexylcarboxylate
4'-propoxy-1,1'-biphenyl-4-yl c-4-cyano-t-4-(6-methacryloyloxyhexyl)-r-1-cyclohexylcarboxylate
4'-pentyl-1,1'-biphenyl-4-yl c-4-cyano-t-4-(6-methacryloyloxyhexyl)-r-1-cyclohexylcarboxylate
4'-hexyl-1,1'-biphenyl-4-yl c-4-cyano-t-4-(6-methacryloyloxyhexyl)-r-1-cyclohexylcarboxylate
4'-heptyl-1,1'-biphenyl-4-yl c-4-cyano-t-4-(6-methacryloyloxyhexyl)-r-1-cyclohexylcarboxylate
4'-octyloxy-1,1'-biphenyl-4-yl c-4-cyano-t-4-(7-methacryloyloxyheptyl)-r-1-cyclohexylcarboxylate
4'-heptyloxy-1,1'-biphenyl-4-yl c-4-cyano-t-4-(7-methacryloyloxyheptyl)-r-1-cyclohexylcarboxylate
4'-hexyloxy-1,1'-biphenyl-4-yl c-4-cyano-t-4-(7-methacryloyloxyheptyl)-r-1-cyclohexylcarboxylate 4'-pentyloxy-1,1'-biphenyl-4-yl c-4-cyano-t-4-(7-methacryloyloxyheptyl)-r-1-cyclohexylcarboxylate 4'-butoxy-1,1'-biphenyl-4-yl c-4-cyano-t-4-(7-methacryloyloxyheptyl)-r-1-cyclohexylcarboxylate 4'-propoxy-1,1'-biphenyl-4-yl c-4-cyano-t-4-(7-methacryloyloxyheptyl)-r-1-cyclohexylcarboxylate 4'-pentyl-1,1'-biphenyl-4-yl c-4-cyano-t-4-(7-methacryloyloxyheptyl)-r-1-cyclohexylcarboxylate 4'-hexyl-1,1'-biphenyl-4-yl c-4-cyano-t-4-(7-methacryloyloxyheptyl)-r-1-cyclohexylcarboxylate 4'-heptyl-1,1'-biphenyl-4-yl c-4-cyano-t-4-(7-methacryloyloxyheptyl)-r-1-cyclohexylcarboxylate 4'-octyloxy-1,1'-biphenyl-4-yl c-4-cyano-t-4-(8-methacryloyloxyoctyl)-r-1-cyclohexylcarboxylate 4'-heptyloxy-1,1'-biphenyl-4-yl c-4-cyano-t-4-(8-methacryloyloxyoctyl)-r-1-cyclohexylcarboxylate 4'-hexyloxy-1,1'-biphenyl-4-yl c-4-cyano-t-4-(8-methacryloyloxyoctyl)-r-1-cyclohexylcarboxylate 4'-pentyloxy-1,1'-biphenyl-4-yl c-4-cyano-t-4-(8-methacryloyloxyoctyl)-r-1-cyclohexylcarboxylate 4'-butoxy-1,1'-biphenyl-4-yl c-4-cyano-t-4-(8-methacryloyloxyoctyl)-r-1-cyclohexylcarboxylate 4'-propoxy-1,1'-biphenyl-4-yl c-4-cyano-t-4-(8-methacryloyloxyoctyl)-r-1-cyclohexylcarboxylate 4'-pentyl-1,1'-biphenyl-4-yl c-4-cyano-t-4-(8-methacryloyloxyoctyl)-r-1-cyclohexylcarboxylate 4'-hexyl-1,1'-biphenyl-4-yl c-4-cyano-t-4-(8-methacryloyloxyoctyl)-r-1-cyclohexylcarboxylate 4'-heptyl-1,1'-biphenyl-4-yl c-4-cyano-t-4-(8-methacryloyloxyoctyl)-r-1-cyclohexylcarboxylate 4'-octyloxy-1,1'-biphenyl-4-yl c-4-cyano-t-4-(9-methacryloyloxynonyl)-r-1-cyclohexylcarboxylate 4'-heptyloxy-1,1'-biphenyl-4-yl c-4-cyano-t-4-(9-methacryloyloxynonyl)-r-1-cyclohexylcarboxylate 4'-hexyloxy-1,1'-biphenyl-4-yl c-4-cyano-t-4-(9-methacryloyloxynonyl)-r-1-cyclohexylcarboxylate 4'-pentyloxy-1,1'-biphenyl-4-yl c-4-cyano-t-4-(9-methacryloyloxynonyl)-r-1-cyclohexylcarboxylate 4'-butoxy-1,1'-biphenyl-4-yl c-4-cyano-t-4-(9-methacryloyloxynonyl)-r-1-cyclohexylcarboxylate 4'-propoxy-1,1'-biphenyl-4-yl c-4-cyano-t-4-(9-methacryloyloxynonyl)-r-1-cyclohexylcarboxylate 4'-pentyl-1,1'-biphenyl-4-yl c-4-cyano-t-4-(9-methacryloyloxynonyl)-r-1-cyclohexylcarboxylate 4'-hexyl-1,1'-biphenyl-4-yl c-4-cyano-t-4-(9-methacryloyloxynonyl)-r-1-cyclohexylcarboxylate 4'-heptyl-1,1'-biphenyl-4-yl c-4-cyano-t-4-(9-methacryloyloxynonyl)-r-1-cyclohexylcarboxylate 4'-octyloxy-1,1'-biphenyl-4-yl c-4-cyano-t-4-(10-methacryloyloxydecyl)-r-1-cyclohexylcarboxylate 4'-heptyloxy-1,1'-biphenyl-4-yl c-4-cyano-t-4-(10-methacryloyloxydecyl)-r-1-cyclohexylcarboxylate 4'-hexyloxy-1,1'-biphenyl-4-yl c-4-cyano-t-4-(10-methacryloyloxydecyl)-r-1-cyclohexylcarboxylate 4'-pentyloxy-1,1'-biphenyl-4-yl c-4-cyano-t-4-(10-methacryloyloxydecyl)-r-1-cyclohexylcarboxylate 4'-butoxy-1,1'-biphenyl-4-yl c-4-cyano-t-4-(10-methacryloyloxydecyl)-r-1-cyclohexylcarboxylate 4'-propoxy-1,1'-biphenyl-4-yl c-4-cyano-t-4-(10-methacryloyloxydecyl)-r-1-cyclohexylcarboxylate 4'-pentyl-1,1'-biphenyl-4-yl c-4-cyano-t-4-(10-methacryloyloxydecyl)-r-1-cyclohexylcarboxylate 4'-hexyl-1,1'-biphenyl-4-yl c-4-cyano-t-4-(10-methacryloyloxydecyl)-r-1-cyclohexylcarboxylate 4'-heptyl-1,1'-biphenyl-4-yl c-4-cyano-t-4-(10-methacryloyloxydecyl)-r-1-cyclohexylcarboxylate 4'-octyloxy-1,1'-biphenyl-4-yl c-4-cyano-t-4-(11-methacryloyloxyundecyl)-r-1-cyclohexylcarboxylate 4'-heptyloxy-1,1'-biphenyl-4-yl c-4-cyano-t-4-(11-methacryloyloxyundecyl)-r-1-cyclohexylcarboxylate 4'-hexyloxy-1,1'-biphenyl-4-yl c-4-cyano-t-4-(11-methacryloyloxyundecyl)-r-1-cyclohexylcarboxylate 4'-pentyloxy-1,1'-biphenyl-4-yl c-4-cyano-t-4-(11-methacryloyloxyundecyl)-r-1-cyclohexylcarboxylate 4'-butoxy-1,1'-biphenyl-4-yl c-4-cyano-t-4-(11-methacryloyloxyundecyl)-r-1-cyclohexylcarboxylate 4'-propoxy-1,1'-biphenyl-4-yl c-4-cyano-t-4-(11-methacryloyloxyundecyl)-r-1-cyclohexylcarboxylate 4'-pentyl-1,1'-biphenyl-4-yl c-4-cyano-t-4-(11-methacryloyloxyundecyl)-r-1-cyclohexylcarboxylate 4'-hexyl-1,1'-biphenyl-4-yl c-4-cyano-t-4-(11-methacryloyloxyundecyl)-r-1-cyclohexylcarboxylate 4'-heptyl-1,1'-biphenyl-4-yl c-4-cyano-t-4-(11-methacryloyloxyundecyl)-r-1-cyclohexylcarboxylate

EXAMPLE 14

The corresponding 4'-octyloxy-1,1'-biphenyl-4-yl c-4-cyano-t-4-(6-acryloyloxyhexyl)-r-1-cyclohexylcarboxylate is obtained analogously to Example 13 by reacting the hydroxy compound with acrylic acid.

The following are prepared analogously:

4-heptyloxy-1,1'-biphenyl-4-yl c-4-cyano-t-4-(6-acryloyloxyhexyl)-r-1-cyclohexylcarboxylate 4'-hexyloxy-1,1'-biphenyl-4-yl c-4-cyano-t-4-(6-acryloyloxyhexyl)-r-1-cyclohexylcarboxylate 4'-pentyloxy-1,1'-biphenyl-4-yl c-4-cyano-t-4-(6-acryloyloxyhexyl)-r-1-cyclohexylcarboxylate 4'-butoxy-1,1'-biphenyl-4-yl c-4-cyano-t-4-(6-acryloyloxyhexyl)-r-1-cyclohexylcarboxylate 4'-propoxy-1,1'-biphenyl-4-yl c-4-cyano-t-4-(6-acryloyloxyhexyl)-r-1-cyclohexylcarboxylate 4'-pentyl-1,1'-biphenyl-4-yl c-4-cyano-t-4-(6-acryloyloxyhexyl)-r-1-cyclohexylcarboxylate 4'hexyl-1,1'-biphenyl-4-yl c-4-cyano-t-4-(6-acryloyloxyhexyl)-r-1-cyclohexylcarboxylate 4'-heptyl-1,1'-biphenyl-4-yl c-4-cyano-t-4-(6-acryloyloxyhexyl)-r-1-cyclohexylcarboxylate 4'-octyloxy-1,1'-biphenyl-4-yl c-4-cyano-t-4-(7-acryloyloxyheptyl)-r-1-cyclohexylcarboxylate 4'-heptyloxy-1,1'-biphenyl-4-yl c-4-cyano-t-4-(7-acryloyloxyheptyl)-r-1-cyclohexylcarboxylate 4'-hexyloxy-1,1'-biphenyl-4-yl c-4-cyano-t-4-(7-acryloyloxyheptyl)-r-1-cyclohexylcarboxylate 4'-pentyloxy-1,1'-biphenyl-4-yl c-4-cyano-t-4-(7-acryloyloxyheptyl)-r-1-cyclohexylcarboxylate 4'-butoxy-1,1'-biphenyl-4-yl c-4-cyano-t-4-(7-acryloyloxyheptyl)-r-1-cyclohexylcarboxylate 4'-propoxy-1,1'-biphenyl-4-yl c-4-cyano-t-4-(7-acryloyloxyheptyl)-r-1-cyclohexylcarboxylate 4'-pentyl-1,1'-biphenyl-4-yl c-4-cyano-t-4-(7-acryloyloxyheptyl-)-r-1-cyclohexylcarboxylate 4'-hexyl-1,1'-biphenyl-4-yl c-4-cyano-t-4-(7-acryloyloxyheptyl)-r-1-cyclohexylcarboxylate 4'-heptyl-1,1'-biphenyl-4-yl c-4-cyano-t-4-(7-acryloyloxyheptyl)-r-1-cyclohexylcarboxylate 4'-octyloxy-1,1'-biphenyl-4-yl c-4-cyano-t-4-(8-acryloyloxyoctyl)-r-1-cyclohexylcarboxylate 4'-heptyloxy-1,1'-biphenyl-4-yl c-4-cyano-t-4-(8-acryloyloxyoctyl)-r-1-cyclohexylcarboxylate 4'-hexyloxy-1,1'-biphenyl-4-yl c-4-cyano-t-4-(8-acryloyloxyoctyl)-r-1-cyclohexylcarboxylate 4'-pentyloxy-1,1'-biphenyl-4-yl c-4-cyano-t-4-(8-acryloyloxyoctyl)-r-1-cyclohexylcarboxylate 4'-butoxy-1,1'-biphenyl-4-yl c-4-cyano-t-4-(8-acryloyloxyoctyl)-r-1-cyclohexylcarboxylate 4'-propoxy-1,1'-biphenyl-4-yl c-4-cyano-t-4-(8-acryloyloxyoctyl)-r-1-cyclohexylcarboxylate 4'-pentyl-1,1'-biphenyl-4-yl c-4-cyano-t-4-(8-acryloyloxyoctyl)-r-1-cyclohexylcarboxylate 4'-hexyl-1,1'-biphenyl-4-yl c-4-cyano-t-4-(8-acryloyloxyoctyl)-r-1-cyclohexylcarboxylate 4'-heptyl-1,1'-biphenyl-4-yl c-4-cyano-t-4-(8-acryloyloxyoctyl)-r-1-cyclohexylcarboxylate 4'-octyloxy-1,1'-biphenyl-4-yl c-4-cyano-t-4-(9-acryloyloxynonyl)-r-1-cyclohexylcarboxylate 4'-heptyloxy-1,1'-biphenyl-4-yl c-4-cyano-t-4-(9-acryloyloxynonyl)-r-1-cyclohexylcarboxylate 4'-hexyloxy-1,1'-biphenyl-4-yl c-4-cyano-t-4-(9-acryloyloxynonyl)-r-1-cyclohexylcarboxylate 4'-pentyloxy-1,1'-biphenyl-4-yl c-4-cyano-t-4-(9-acryloyloxynonyl)-r-1-cyclohexylcarboxylate 4'-butoxy-1,1'-biphenyl-4-yl c-4-cyano-t-4-(9acryloyloxynonyl)-r-1-cyclohexylcarboxylate 4'-propoxy-1,1'-biphenyl-4-yl c-4-cyano-t-4-(9-acryloyloxynonyl)-r-1-cyclohexylcarboxylate 4'-pentyl-1,1'-biphenyl-4-yl c-4-cyano-t-4-(9-acryloyloxynonyl)-r-1-cyclohexylcarboxylate 4'-hexyl-1,1'-biphenyl-4-yl c-4-cyano-t-4-(9-acryloyloxynonyl)-r-1-cyclohexylcarboxylate 4'-heptyl-1,1'-biphenyl-4-yl c-4-cyano-t-4-(9-acryloyloxynonyl)-r-1-cyclohexylcarboxylate 4'-octyloxy-1,1'-biphenyl-4-yl c-4-cyano-t-4-(10-acryloyloxydecyl)-r-1-cyclohexylcarboxylate 4'-heptyloxy-1,1'-biphenyl-4-yl c-4-cyano-t-4-(10-acryloyloxydecyl)-r-1-cyclohexylcarboxylate 4'-hexyloxy-1,1'-biphenyl-4-yl c-4-cyano-t-4-(10-acryloyloxydecyl)-r-1-cyclohexylcarboxylate 4'-pentyloxy-1,1'-biphenyl-4-yl c-4-cyano-t-4-(10-acryloyloxydecyl)-r-1-cyclohexylcarboxylate 4'-butoxy-1,1'-biphenyl-4-yl c-4-cyano-t-4-(10-acryloyloxydecyl)-r-1-cyclohexylcarboxylate 4'-propoxy-1,1'-biphenyl-4-yl c-4-cyano-t-4-(10-acryloyloxydecyl)-r-1-cyclohexylcarboxylate 4'-pentyl-1,1'-biphenyl-4-yl c-4-cyano-t-4-(10-acryloyloxydecyl)-r-1-cyclohexylcarboxylate 4'-hexyl-1,1'-biphenyl-4-yl c-4-cyano-t-4-(10-acryloyloxydecyl)-r-1-cyclohexylcarboxylate 4'-heptyl-1,1'-biphenyl-4-yl c-4-cyano-t-4-(10-acryloyloxydecyl)-r-1-cyclohexylcarboxylate 4'-octyloxy-1,1'-biphenyl-4-yl c-4-cyano-t-4-(11-acryloyloxyundecyl)-r-1-cyclohexylcarboxylate 4'-heptyloxy-1,1'-biphenyl-4-yl c-4-cyano-t-4-(11-acryloyloxyundecyl)-r-1-cyclohexylcarboxylate 4'-hexyloxy-1,1'-biphenyl-4-yl c-4-cyano-t-4-(11-acryloyloxyundecyl)-r-1-cyclohexylcarboxylate 4'-pentyloxy-1,1'-biphenyl-4-yl c-4-cyano-t-4-(11-acryloyloxyundecyl)-r-1-cyclohexylcarboxylate 4'-butoxy-1,1'-biphenyl-4-yl c-4-cyano-t-4-(11-acryloyloxyundecyl)-r-1-cyclohexylcarboxylate 4'-propoxy-1,1'-biphenyl-4-yl c-4-cyano-t-4-(11-acryloyloxyundecyl)-r-1-cyclohexylcarboxylate 4'-pentyl-1,1'-biphenyl-4-yl c-4-cyano-t-4-(11-acryloyloxyundecyl)-r-1-cyclohexylcarboxylate 4'-hexyl-1,1'-biphenyl-4-yl c-4-cyano-t-4-(11-acryloyloxyundecyl)-r-1-cyclohexylcarboxylate 4'-heptyl-1,1'-biphenyl-4-yl c-4-cyano-t-4-(11-acryloyloxyundecyl)-r-1-cyclohexylcarboxylate

EXAMPLE 15

A solution of 4.6 g of 4-(6-methacryloyloxyhexyloxy)benzoic acid and 10 mg of 2,6-di-tert.-butyl-4-methylphenol in 20 ml of thionyl chloride is stirred, the excess thionyl chloride is removed in vacuo, the residue is taken up in 20 ml of THF, and this solution is added at 0° to a mixture of 4.04 g of 4-(5-heptylpyridin-2-yl)-phenol, 3 ml of triethylamine and 50 ml of THF. After 18 hours' stirring at room temperature, 100 ml of $CH_2Cl_2$ are added and the mixture is extracted with water. The organic phase is worked up to give, after purification by chromatography over silica gel, 4-(5-heptylpyridin-2-yl)-phenyl 4-(6-methacryloyloxyhexyloxy)-benzoate.

The following are prepared analogously:

4-(5-ethylpyridin-2-yl)-phenyl 4-(6-methacryloyloxyhexyloxy)-benzoate 4-(5-propylpyridin-2-yl)-phenyl 4-(6-methacryloyloxyhexyloxy)-benzoate 4-(5-butylpyridin-2-yl)-phenyl 4-(6-methacryloyloxyhexyloxy)-benzoate 4-(5-pentylpyridin-2-yl)-phenyl 4-(6-methacryloyloxyhexyloxy)-benzoate 4-(5-hexylpyridin-2-yl)-phenyl 4-(6-methacryloyloxyhexyloxy)-benzoate 4-(5-ethoxypyridin-2-yl)-phenyl 4-(6-methacryloyloxyhexyloxy)-benzoate 4-(5-propoxypyridin-2-yl)-phenyl 4-(6-methacryloyloxyhexyloxy)-benzoate 4-(5-butoxypyridin-2-yl)-phenyl 4-(6-methacryloyloxyhexyloxy)-benzoate 4-(5-pentyloxypyridin-2-yl)-phenyl 4-(6-methacryloyloxyhexyloxy)-benzoate 4-(5-heptylpyridin-2-yl)-phenyl 4-(7-methacryloyloxyheptyloxy)-benzoate 4-(5-ethylpyridin-2-yl)-phenyl 4-(7-methacryloyloxyheptyloxy)-benzoate 4-(5-propylpyridin-2-yl)-phenyl 4-(7-methacryloyloxyheptyloxy)-benzoate 4-(5-butylpyridin-2-yl)-phenyl 4-(7-methacryloyloxyheptyloxy)-benzoate 4-(5-pentylpyridin-2-yl)-phenyl 4-(7-methacryloyloxyheptyloxy)-benzoate 4-(5-hexylpyridin-2-yl)-phenyl 4-(7-methacryloyloxyheptyloxy)-benzoate 4-(5-ethoxypyridin-2-yl)-phenyl 4-(7-methacryloyloxyheptyloxy)-benzoate 4-(5-propoxypyridin-2-yl)-phenyl 4-(7-methacryloyloxyheptyloxy)-benzoate 4-(5-butoxypyridin-2-yl)-phenyl 4-(7-methacryloyloxyheptyloxy)-benzoate 4-(5-pentyloxypyridin-2-yl)-phenyl 4-(7-methacryloyloxyheptyloxy)-benzoate 4-(5-heptylpyridin-2-yl)-phenyl 4-(8-methacryloyloxyoctyloxy)-benzoate 4-(5-ethylpyridin-2-yl)-phenyl 4-(8-methacryloyloxyoctyloxy)-benzoate 4-(5-propylpyridin-2-yl)-phenyl 4-(8-methacryloyloxyoctyloxy)-benzoate 4-(5-butylpyridin-2-yl)-phenyl 4-(8-methacryloyloxyoctyloxy)-benzoate 4-(5-pentylpyridin-2-yl)-phenyl 4-(8-methacryloyloxyoctyloxy)-benzoate 4-(5-hexylpyridin-2-yl)-phenyl 4-(8-methacryloyloxyoctyloxy)-benzoate 4-(5-ethoxypyridin-2-yl)-phenyl 4-(8-methacryloyloxyoctyloxy)-benzoate 4-(5-propoxypyridin-2-yl)-phenyl 4-(8-methacryloyloxyoctyloxy)-benzoate 4-(5-butoxypyridin-2-yl)-phenyl 4-(8-methacryloyloxyoctyloxy)-benzoate 4-(5-pentyloxypyridin-2-yl)-phenyl 4-(8-methacryloyloxyoctyloxy)-benzoate 4-(5-heptylpyridin-2-yl)-phenyl 4-(9-methacryloyloxynonyloxy)-benzoate
4-(5-ethylpyridin-2-yl)-phenyl 4-(9-methacryloyloxynonyloxy)-benzoate
4-(5-propylpyridin-2-yl)-phenyl 4-(9-methacryloyloxynonyloxy)-benzoate
4-(5-butylpyridin-2-yl)-phenyl 4-(9-methacryloyloxynonyloxy)-benzoate
4-(5-pentylpyridin-2-yl)-phenyl 4-(9-methacryloyloxynonyloxy)-benzoate
4-(5-hexylpyridin-2-yl)-phenyl 4-(9-methacryloyloxynonyloxy)-benzoate
4-(5-ethoxypyridin-2-yl)-phenyl 4-(9-methacryloyloxynonyloxy)-benzoate
4-(5-propoxypyridin-2-yl)-phenyl 4-(9-methacryloyloxynonyloxy)-benzoate
4-(5-butoxypyridin-2-yl)-phenyl 4-(9-methacryloyloxynonyloxy)-benzoate
4-(5-pentyloxypyridin-2-yl)-phenyl 4-(9-methacryloyloxynonyloxy)-benzoate
4-(5-heptylpyridin-2-yl)-phenyl 4-(10-methacryloyloxydecyloxy)-benzoate
4-(5-ethylpyridin-2-yl)-phenyl 4-(10-methacryloyloxydecyloxy)-benzoate
4-(5-propylpyridin-2-yl)-phenyl 4-(10-methacryloyloxydecyloxy)-benzoate
4-(5-butylpyridin-2-yl)-phenyl 4-(10-methacryloyloxydecyloxy)-benzoate
4-(5-pentylpyridin-2-yl)-phenyl 4-(10-methacryloyloxydecyloxy)-benzoate
4-(5-hexylpyridin-2-yl)-phenyl 4-(10-methacryloyloxydecyloxy-)-benzoate
4-(5-ethoxypyridin-2-yl)-phenyl 4-(10-methacryloyloxydecyloxy)-benzoate
4-(5-propoxypyridin-2-yl)-phenyl 4-(10-methacryloyloxydecyloxy)-benzoate
4-(5-butoxypyridin-2-yl)-phenyl 4-(10-methacryloyloxydecyloxy)-benzoate
4-(5-pentyloxypyridin-2-yl)-phenyl 4-(10-methacryloyloxydecyloxy)-benzoate
4-(5-heptylpyridin-2-yl)-phenyl 4-(11-methacryloyloxyundecyloxy)-benzoate
4-(5-ethylpyridin-2-yl)-phenyl 4-(11-methacryloyloxyundecyloxy)-benzoate
4-(5-propylpyridin-2-yl)-phenyl 4-(11-methacryloyloxyundecyloxy)-benzoate
4-(5-butylpyridin-2-yl)-phenyl 4-(11-methacryloyloxyundecyloxy)-benzoate
4-(5-pentylpyridin-2-yl)-phenyl 4-(11-methacryloyloxyundecyloxy)-benzoate
4-(5-hexylpyridin-2-yl)-phenyl 4-(11-methacryloyloxyundecyloxy)-benzoate
4-(5-ethoxypyridin-2-yl)-phenyl 4-(11-methacryloyloxyundecyloxy)-benzoate
4-(5-propoxypyridin-2-yl)-phenyl 4-(11-methacryloyloxyundecyloxy)-benzoate
4-(5-butoxypyridin-2-yl)-phenyl 4-(11-methacryloyloxyundecyloxy)-benzoate
4-(5-pentyloxypyridin-2-yl)-phenyl 4-(11-methacryloyloxyundecyloxy)-benzoate
4-(5-heptylpyridin-2-yl)-phenyl 4-(6-acryloyloxyhexyloxy)benzoate
4-(5-ethylpyridin-2-yl)-phenyl 4-(6-acryloyloxyhexyloxy)-benzoate
4-(5-propylpyridin-2-yl)-phenyl 4-(6-acryloyloxyhexyloxy)-benzoate
4-(5-butylpyridin-2-yl)-phenyl 4-(6-acryloyloxyhexyloxy)-benzoate
4-(5-pentylpyridin-2-yl)-phenyl 4-(6-acryloyloxyhexyloxy)-benzoate
4-(5-hexylpyridin-2-yl)-phenyl 4-(6-acryloyloxyhexyloxy)benzoate
4-(5-ethoxypyridin-2-yl)-phenyl 4-(6-acryloyloxyhexyloxy)-benzoate
4-(5-propoxypyridin-2-yl)-phenyl 4-(6-acryloyloxyhexyloxy)-benzoate
4-(5-butoxypyridin-2-yl)-phenyl 4-(6-acryloyloxyhexyloxy)-benzoate
4-(5-pentyloxypyridin-2-yl)-phenyl 4-(6-acryloyloxyhexyloxy)-benzoate
4-(5-heptylpyridin-2-yl)-phenyl 4-(7-acryloyloxyheptyloxy)-benzoate
4-(5-ethylpyridin-2-yl)-phenyl 4-(7-acryloyloxyheptyloxy)-benzoate
4-(5-propylpyridin-2-yl)-phenyl 4-(7-acryloyloxyheptyloxy)-benzoate
4-(5-butylpyridin-2-yl)-phenyl 4-(7-acryloyloxyheptyloxy)-benzoate
4-(5-pentylpyridin-2-yl)-phenyl 4-(7-acryloyloxyheptyloxy)-benzoate
4-(5-hexylpyridin-2-yl)-phenyl 4-(7-acryloyloxyheptyloxy)-benzoate
4-(5-ethoxypyridin-2-yl)-phenyl 4-(7-acryloyloxyheptyloxy)-benzoate
4-(5-propoxypyridin-2-yl)-phenyl 4-(7-acryloyloxyheptyloxy)-benzoate
4-(5-butoxypyridin-2-yl)-phenyl 4-(7-acryloyloxyheptyloxy)-benzoate
4-(5-pentyloxypyridin-2-yl)-phenyl 4-(7-acryloyloxyheptyloxy)-benzoate
4-(5-heptylpyridin-2-yl)-phenyl 4-(8-acryloyloxyoctyloxy)-benzoate
4-(5-ethylpyridin-2-yl)-phenyl 4-(8-acryloyloxyoctyloxy)-benzoate
4-(5-propylpyridin-2-yl)-phenyl 4-(8-acryloyloxyoctyloxy)-benzoate
4-(5-butylpyridin-2yl)-phenyl 4-(8-acryloyloxyoctyloxy)-benzoate
4-(5-pentylpyridin-2-yl)-phenyl 4-(8-acryloyloxyoctyloxy)-benzoate
4-(5-hexylpyridin-2-yl)-phenyl 4-(8-acryloyloxyoctyloxy)-benzoate
4-(5-ethoxypyridin-2-yl)-phenyl 4-(8-acryloyloxyoctyloxy)-benzoate
4-(5-propoxypyridin-2-yl)-phenyl 4-(8-acryloyloxyoctyloxy)-benzoate
4-(5-butoxypyridin-2-yl)-phenyl 4-(8-acryloyloxyoctyloxy)-benzoate
4-(5-pentyloxypyridin-2-yl)-phenyl 4-(8-acryloyloxyoctyloxy)-benzoate
4-(5-heptylpyridin-2-yl)-phenyl 4-(9-acryloyloxynonyloxy)-benzoate
4-(5-ethylpyridin-2-yl)-phenyl 4-(9-acryloyloxynonyloxy)-benzoate
4-(5-propylpyridin-2-yl)-phenyl 4-(9-acryloyloxynonyloxy)-benzoate
4-(5-butylpyridin-2-yl)-phenyl 4-(9-acryloyloxynonyloxy)-benzoate
4-(5-pentylpyridin-2-yl)-phenyl 4-(9-acryloyloxynonyloxy)-benzoate
4-(5-hexylpyridin-2-yl)-phenyl 4-(9-acryloyloxynonyloxy)-benzoate
4-(5-ethoxypyridin-2-yl)-phenyl 4-(9-acryloyloxynonyloxy)-benzoate
4-(5-propoxypyridin-2-yl)-phenyl 4-(9-acryloyloxynonyloxy)-benzoate

| | |
|---|---|
| 4-(5-butoxypyridin-2-yl)-phenyl | 4-(9-acryloyloxynonyloxy)-benzoate |
| 4-(5-pentyloxypyridin-2-yl)-phenyl | 4-(9-acryloyloxynonyloxy)-benzoate |
| 4-(5-heptylpyridin-2-yl)-phenyl | 4-(10-acryloyloxydecyloxy)-benzoate |
| 4-(5-ethylpyridin-2-yl)-phenyl | 4-(10-acryloyloxydecyloxy)-benzoate |
| 4-(5-propylpyridin-2-yl)-phenyl | 4-(10-acryloyloxydecyloxy)-benzoate |
| 4-(5-butylpyridin-2-yl)-phenyl | 4-(10-acryloyloxydecyloxy)-benzoate |
| 4-(5-pentylpyridin-2-yl)-phenyl | 4-(10-acryloyloxydecyloxy)-benzoate |
| 4-(5-hexylpyridin-2-yl)-phenyl | 4-(10-acryloyloxydecyloxy)-benzoate |
| 4-(5-ethoxypyridin-2-yl)-phenyl | 4-(10-acryloyloxydecyloxy)-benzoate |
| 4-(5-propoxypyridin-2-yl)-phenyl | 4-(10-acryloyloxydecyloxy)-benzoate |
| 4-(5-butoxypyridin-2-yl)-phenyl | 4-(10-acryloyloxydecyloxy)-benzoate |
| 4-(5-pentyloxypyridin-2-yl)-phenyl | 4-(10-acryloyloxydecyloxy)-benzoate |
| 4-(5-heptylpyridin-2-yl)-phenyl | 4-(11-acryloyloxyundecyloxy)-benzoate |
| 4-(5-ethylpyridin-2-yl)-phenyl | 4-(11-acryloyloxyundecyloxy)-benzoate |
| 4-(5-propylpyridin-2-yl)-phenyl | 4-(11-acryloyloxyundecyloxy)-benzoate |
| 4-(5-butylpyridin-2-yl)-phenyl | 4-(11-acryloyloxyundecyloxy)-benzoate |
| 4-(5-pentylpyridin-2-yl)-phenyl | 4-(11-acryloyloxyundecyloxy)-benzoate |
| 4-(5-hexylpyridin-2-yl)-phenyl | 4-(11-acryloyloxyundecyloxy)-benzoate |
| 4-(5-ethoxypyridin-2-yl)-phenyl | 4-(11-acryloyloxyundecyloxy)-benzoate |
| 4-(5-propoxypyridin-2-yl)-phenyl | 4-(11-acryloyloxyundecyloxy)-benzoate |
| 4-(5-butoxypyridin-2-yl)-phenyl | 4-(11-acryloyloxyundecyloxy)-benzoate |
| 4-(5-pentyloxypyridin-2-yl)-phenyl | 4-(11-acryloyloxyundecyloxy)-benzoate |

EXAMPLE 16 a) A solution of 4.03 g of c-4-(4'-hydroxy-1,1'-biphenyl-4-yl)-1-(11-hydroxyundecyl)-r-1-cyclohexylcarbonitrile [which can be prepared by saponification, in the presence of potassium tert.-butylate in N-methylpyrrolidone], of c-4-(4'methoxy-1,1'-biphenyl-4-yl)-1-(11-hydroxyundecyl)-r-1-cyclohexylcarbonitrile, which can be prepared analogously to Example 5a and b], 10 g of methacrylic acid, 0.4 g of hydroquinone and 0.4 g of p-toluenesulfonic acid monohydrate in 150 ml of chloroform is heated under a water separator for 3 days.

The reaction mixture is extracted and the organic phase is worked up to give, after chromatography over silica gel, c-4-(4'-hydroxy-1,1'-biphenyl-4-yl)-1-(11-methacryloyloxyundecyl)-r-1-cyclohexylcarbonitrile.

b) 1.21 g of DCCI in 5 ml of CH$_2$Cl$_2$ are added to a solution of 3.09 g of the compound prepared in a), 819 mg of (R)-2-chloro-3-methylbutanoic acid and 73.3 mg of 4-dimethylaminopyridine in 20 ml of CH$_2$Cl$_2$, and the mixture is stirred for 18 hours at room temperature. The precipitate is filtered off with suction, the filtrate is concentrated and recrystallization from ethanol gives optically active c-4-[4'-((R)-2-chloro-3-methylbutyryloxy)-1,1'-biphenyl-4-yl]-1-(11-methacryloyloxyundecyl)-r-1-cyclohexylcarbonitrile.

The following, optically active, compounds are obtained analogously:

c-4-[4'-(2-chloro-3-methylbutyryloxy)-1,1'-biphenyl-4-yl]-1-(10-methacryloyloxydecyl)-r-1-cyclohexylcarbonitrile c-4-[4'-(2-chloro-3-methylbutyryloxy)-1,1'-biphenyl-4-yl]-1-(9-methacryloyloxynonyl)-r-1-cyclohexylcarbonitrile c-4-[4'-(2-chloro-3-methylbutyryloxy)-1,1'-biphenyl-4-yl]-1-(8-methacryloyloxyoctyl)-r-1-cyclohexylcarbonitrile c-4-[4'-(2-chloro-3-methylbutyryloxy)-1,1'-biphenyl-4-yl]-1-(7-methacryloyloxyheptyl)-r-1-cyclohexylcarbonitrile c-4-[4'-(2-chloro-3-methylbutyryloxy)-1,1'-biphenyl-4-yl]-1-(6-methacryloyloxyhexyl)-r-1-cyclohexylcarbonitrile c-4-[4'-(2-chloro-3-methylbutyryloxy)-1,1'-biphenyl-4-yl]-1-(5-methacryloyloxypentyl)-r-1-cyclohexylcarbonitrile c-4-[4'-(2-chloro-3-methylbutyryloxy)-1,1'-biphenyl-4-yl]-1-(11-acryloyloxyundecyl)-r-1-cyclohexylcarbonitrile c-4-[4'-(2-chloro-3-methylbutyryloxy)-1,1'-biphenyl-4-yl]-1-(10-acryloyloxydecyl)-r-1-cyclohexylcarbonitrile c-4-[4'-(2-chloro-3-methylbutyryloxy)-1,1'-biphenyl-4-yl]-1-(9-acryloyloxynonyl)-r-1-cyclohexylcarbonitrile c-4-[4'-(2-chloro-3-methylbutyryloxy)-1,1'-biphenyl-4-yl]-1-(8-acryloyloxyoctyl)-r-1-cyclohexylcarbonitrile c-4-[4'-(2-chloro-3-methylbutyryloxy)-1,1'-biphenyl-4-yl]-1-(7-acryloyloxyheptyl)-r-1-cyclohexylcarbonitrile c-4-[4'-(2-chloro-3-methylbutyryloxy)-1,1'-biphenyl-4-yl]-1-(6-acryloyloxyhexyl)-r-1-cyclohexylcarbonitrile c-4-[4'-(2-chloro-3-methylbutyryloxy)-1,1'-biphenyl-4-yl]-1-(5-acryloyloxypentyl)-r-1-cyclohexylcarbonitrile

EXAMPLE 17 a) 252 mg of sodium hydride are added to a solution of 4.48 g of c-4-[4'-octyloxy-1,1'-biphenyl-4-yl]-1-[(S)-2-hydroxypropyl]-r-1-cyclohexylcarbonitrile and 4.2 g of 11-iodoundec-1-ene in 50 ml of 1,2-dimethoxyethane, and the mixture is stirred for 18 hours at room temperature. The mixture is poured into ice water and extracted with CH$_2$Cl$_2$. Working up the organic phase and chromatographing the product over silica gel gives c-4-[4'-octyloxy-1,1'-biphenyl-4-yl]-1-[2-methyl-3-oxatetradec-13-enyl]-r-1-cyclohexylcarbonitrile (optically active).

b) The olefin derivative prepared in a) is converted, analogously to Example 5b), into c-4-[4'-octyloxy-1,1'-biphenyl-4-yl]-1-[2-methyl-3-oxa-14-hydroxytetradecyl]-r-1-cyclohexylcarbonitrile (optically active), which is reacted analogously to Example 6 with methacrylic acid to give c-4-[4'-octyloxy-1,1'-biphenyl-4-yl]-1-[2-methyl-3-oxa-14-(methacryloyloxy)-tetradecyl]-r-1-cyclohexylcarbonitrile (optically active).

The following are prepared analogously:

c-4-[4'-ethoxy-1,1'-biphenyl-4-yl]-1-[2-methyl-3-oxa-14-(methacryloyloxy)-tetradecyl]-r-1-cyclohexylcarbonitrile, optically active c-4-[4'-propoxy-1,1'-biphenyl-4-yl]-1-[2-methyl-3-oxa-14-(methacryloyloxy)-tetradecyl]-r-1-cyclohexylcarbonitrile, optically active c-4-[4'-butoxy-1,1'-biphenyl-4-yl]-1-[2-methyl-3-oxa-14-(methacryloyloxy)-tetradecyl]-r-1-cyclohexylcarbonitrile, optically active c-4-[4'-pentyloxy-1,1'-biphenyl-4-yl]-1-[2-methyl-3-oxa-14-(methacryloyloxy)-tetradecyl]-r-1-cyclohexylcarbonitrile, optically active c-4-[4'-hexyloxy-1,1'-biphenyl-4-yl]-1-[2-methyl-3-oxa-14-(methacryloyloxy)-tetradecyl]-r-1-cyclohexylcarbonitrile, optically active c-4-[4'-heptyloxy-1,1'-biphenyl-4-yl]-1-[2-methyl-3-oxa-14-(methacryloyloxy)-tetradecyl]-r-1-cyclohexylcarbonitrile, optically active c-4-[4'-butyl-1,1'-biphenyl-4-yl]-1-[2-methyl-3-oxa-14-(methacryloyloxy)-tetradecyl]-r-1-cyclohexylcarbonitrile, optically active c-4-[4'-pentyl-1,1'-biphenyl-4-yl]-1-[2-methyl-3-oxa-14-(methacryloyloxy)-tetradecyl]-r-1-cyclohexylcarbonitrile, optically active c-4-[4'-hexyl-1,1'-biphenyl-4-yl]-1-[2-methyl-3-oxa-14-(methacryloyloxy)-tetradecyl]-r-1-cyclohexylcarbonitrile, optically active c-4-[4'-heptyl-1,1'-biphenyl-4-yl]-1-[2-methyl-3-oxa-14-(methacryloyloxy)-tetradecyl]-r-1-cyclohexylcarbonitrile, optically active c-4-[4'-octyloxy-1,1'-biphenyl-4-yl]-1-[2-methyl-3-oxa-14-(acryloyloxy)-tetradecyl]-r-1-cyclohexylcarbonitrile, optically active c-4-[4'-ethoxy-1,1'-biphenyl-4-yl]-1-[2-methyl-3-oxa-14-(acryloyloxy)-tetradecyl]-r-1-cyclohexylcarbonitrile, optically active c-4-[4'-propoxy-1,1'-biphenyl-4-yl]-1-[2-methyl-3-oxa-14-(acryloyloxy)-tetradecyl]-r-1-cyclohexylcarbonitrile, optically active c-4-[4'-butoxy-1,1'-biphenyl-4-yl]-1-[2-methyl-3-oxa-14-(acryloyloxy)-tetradecyl]-r-1-cyclohexylcarbonitrile, optically active c-4-[4'-pentyloxy-1,1'-biphenyl-4-yl]-1-[2-methyl-3-oxa-14-(acryloyloxy)-tetradecyl]-r-1-cyclohexylcarbonitrile, optically active c-4-[4'-hexyloxy-1,1'-biphenyl-4-yl]-1-[2-methyl-3-oxa-14-(acryloyloxy)-tetradecyl]-r-1-cyclohexylcarbonitrile, optically active c-4-[4'-heptyloxy-1,1'-biphenyl-4-yl]-1-[2-methyl-3-oxa-14-(acryloyloxy)-tetradecyl]-r-1-cyclohexylcarbonitrile, optically active c-4-[4'-butyl-1,1'-biphenyl-4-yl]-1-[2-methyl-3-oxa-14-(acryloyloxy)-tetradecyl]-r-1-cyclohexylcarbonitrile, optically active c-4-[4'-pentyl-1,1'-biphenyl-4-yl]-1-[2-methyl-3-oxa-14-(acryloyloxy)-tetradecyl]-r-1-cyclohexylcarbonitrile, optically active c-4-[4'-hexyl-1,1'-biphenyl-4-yl]-1-[2-methyl-3-oxa-14-(acryloyloxy)-tetradecyl]-r-1-cyclohexylcarbonitrile, optically active c-4-[4'-heptyl-1,1'-biphenyl-4-yl]-1-[2-methyl-3-oxa-14-(acryloyloxy)-tetradecyl]-r-1-cyclohexylcarbonitrile, optically active

EXAMPLE A

A solution of 2 g of 4-[c-1-cyano-r-4-(r-4-pentyl-t-1-cyclohexyl)-t-1-cyclohexyl]-butyl methacrylate (which can be prepared as in Example 4) and 16.4 mg of azobisisobutyronitrile in 10 ml of toluene is heated at 60° under nitrogen for 20 hours. The polymer is reprecipitated twice from ethanol, and a colorless, fibrous polymer of $S_4$ 172° I is obtained.

EXAMPLE B a) A solution of 1.2 g of dicyclohexylcarbodiimide in 2 ml of $CH_2Cl_2$ is added at 0° to a solution of 1.3 g of 4-hydroxy-4'-methoxy-3-nitro-1,1'-biphenyl, 1.6 g of 4-(6-methacryloyloxyhexyloxy)-benzoic acid and 64.8 mg of 4-dimethylaminopyridine in 30 ml of $CH_2Cl_2$, and the mixture is stirred for 2 hours at room temperature. The precipitate is filtered off with suction, the filtrate is concentrated and the residue is chromatographed over silica gel using 8:2 petroleum ether/ethyl acetate. This gives 6-[4-(4'-methoxy-3-nitro-1,1'-biphenyl-4-yloxycarbonyl)-phenoxy]-hexyl methacrylate.

The following are prepared analogously:

2-[4-(4'-methoxy-3-nitro-1,1'-biphenyl-4-yloxycarbonyl)phenoxy]-ethyl methacrylate 2-[4-(4'-ethoxy-3-nitro-1,1'-biphenyl-4-yloxycarbonyl)-phenoxy]-ethyl methacrylate 2-[4-(4'-propoxy-3-nitro-1,1'-biphenyl-4-yloxycarbonyl)-phenoxy]-ethyl methacrylate 2-[4--(4'-butoxy-3-nitro-1,1'-biphenyl-4-yloxycarbonyl)-phenoxy]-ethyl methacrylate 2-[4-(4'-pentyloxy-3-nitro-1,1'-biphenyl-4-yloxycarbonyl)phenoxy]-ethyl methacrylate 2-[4-(4'-hexyloxy-3-nitro-1,1'-biphenyl-4-yloxycarbonyl)-phenoxy-ethyl methacrylate 3-[4-(4'-methoxy-3-nitro-1,1'-biphenyl-4-yloxycarbonyl)phenoxy]-propyl methacrylate 3-[4-(4'-ethoxy-3-nitro-1,1'-biphenyl-4-yloxycarbonyl)-phenoxy]-propyl methacrylate 3-[4-(4'-propoxy-3-nitro-1,1'-biphenyl-4-yloxycarbonyl)-phenoxy]-propyl methacrylate 3-[4-(4'-butoxy-3-nitro-1,1'-biphenyl-4-yloxycarbonyl)-phenoxy]-propyl methacrylate 3-[4-(4'-pentyloxy-3-nitro-1,1'-biphenyl-4-yloxycarbonyl)phenoxy]-propyl methacrylate 3-[4-(4'-hexyloxy-3-nitro-1,1'-biphenyl-4-yloxycarbonyl)phenoxy]-propyl methacrylate 4-[4-(4'-methoxy-3-nitro-1,1'-biphenyl-4-yloxycarbonyl)phenoxy]-butyl methacrylate 4-[4-(4'-ethoxy-3-nitro-1,1'-biphenyl-4-yloxycarbonyl)-phenoxy]-butyl methacrylate 4-[4-(4'-propoxy-3-nitro-1,1'-biphenyl-4-yloxycarbonyl)phenoxy]-butyl methacrylate 4-[4-(4'-butoxy-3-nitro-1,1'-biphenyl-4-yloxycarbonyl)-phenoxy]-butyl methacrylate 4-[4-(4'-pentyloxy-3-nitro-1,1'-biphenyl-4-yloxycarbonyl)-phenoxy]-butyl methacrylate 4-[4-(4'-hexyloxy-3-nitro-1,1'-biphenyl-4-yloxycarbonyl)phenoxy]-butyl methacrylate 5-[4-(4'-methoxy-3-nitro-1,1'-biphenyl-4-yloxycarbonyl)phenoxy]-pentyl methacrylate 5-[4-(4'-ethoxy-3-nitro-1,1'-biphenyl-4-yloxycarbonyl)-phenoxy]-pentyl methacrylate 5-[4-(4'-propoxy-3-nitro-1,1'-biphenyl-4-yloxycarbonyl)-phenoxy]-pentyl methacrylate 5-[4-(4'-butoxy-3-nitro-1,1'-biphenyl-4-yloxycarbonyl)-phenoxy]-pentyl methacrylate 5-[4-(4'-pentyloxy-3-nitro-1,1'-biphenyl-4-yloxycarbonyl)-phenoxy]-pentyl methacrylate 5-[4-(4'-hexyloxy-3-nitro-1,1'-biphenyl-4-yloxycarbonyl)-phenoxy]-pentyl methacrylate 6-[4-(4'-ethoxy-3-nitro-1,1'-biphenyl-4-yloxycarbonyl)-phenoxy]-hexyl methacrylate 6-[4-(4'-propoxy-3-nitro-1,1'-biphenyl-4-yloxycarbonyl)-phenoxy]-hexyl methacrylate
6-[4-(4'-butoxy-3-nitro-1,1'-biphenyl-4-yloxycarbonyl)-phenoxy]-hexyl methacrylate
6-[4-(4'-pentyloxy-3-nitro-1,1'-biphenyl-4-yloxycarbonyl)-phenoxy]-hexyl methacrylate
6-[4-(4'-hexyloxy-3-nitro-1,1'-biphenyl-4-yloxycarbonyl)-phenoxy]-hexyl methacrylate
7-[4-(4'-methoxy-3-nitro-1,1'-biphenyl-4-yloxycarbonyl)-phenoxy]-heptyl methacrylate
7-[4-(4'-ethoxy-3-nitro-1,1'-biphenyl-4-yloxycarbonyl)-phenoxy]-heptyl methacrylate
7-[4-(4'-propoxy-3-nitro-1,1'-biphenyl-4-yloxycarbonyl)-phenoxy]-heptyl methacrylate
7-[4-(4'-butoxy-3-nitro-1,1'-biphenyl-4-yloxycarbonyl)-phenoxy]-heptyl methacrylate
7-[4-(4'-pentyloxy-3-nitro-1,1'-biphenyl-4-yloxycarbonyl)-phenoxy]-heptyl methacrylate
7-[4-(4'-hexyloxy-3-nitro-1,1'-biphenyl-4-yloxycarbonyl)-phenoxy]-heptyl methacrylate
8-[4-(4'-methoxy-3-nitro-1,1'-biphenyl-4-yloxycarbonyl)-phenoxy]-octyl methacrylate
8-[4-(4'-ethoxy-3-nitro-1,1'-biphenyl-4-yloxycarbonyl)-phenoxy]-octyl methacrylate
8-[4-(4'-propoxy-3-nitro-1,1'-biphenyl-4-yloxycarbonyl)-phenoxy]-octyl methacrylate
8-[4-(4'-butoxy-3-nitro-1,1'-biphenyl-4-yloxycarbonyl)-phenoxy]-octyl methacrylate
8-[4-(4'-pentyloxy-3-nitro-1,1'-biphenyl-4-yloxycarbonyl)-phenoxy]-octyl methacrylate
8-[4-(4'-hexyloxy-3-nitro-1,1'-biphenyl-4-yloxycarbonyl)-phenoxy]-octyl methacrylate
9-[4-(4'-methoxy-3-nitro-1,1'-biphenyl-4-yloxycarbonyl)-phenoxy]-nonyl methacrylate
9-[4-(4'-ethoxy-3-nitro-1,1'-biphenyl-4-yloxycarbonyl)-phenoxy]-nonyl methacrylate
9-[4-(4'-propoxy-3-nitro-1,1'-biphenyl-4-yloxycarbonyl)-phenoxy]-nonyl methacrylate
9-[4-(4'-butoxy-3-nitro-1,1'-biphenyl-4-yloxycarbonyl)-phenoxy]-nonyl methacrylate
9-[4-(4'-pentyloxy-3-nitro-1,1'-biphenyl-4-yloxycarbonyl)-phenoxy]-nonyl methacrylate
9-[4-(4'-hexyloxy-3-nitro-1,1'-biphenyl-4-yloxycarbonyl)-phenoxy]-nonyl methacrylate
10-[4-(4'-methoxy-3-nitro-1,1'-biphenyl-4-yloxycarbonyl)-phenoxy]-decyl methacrylate
10-[4-(4'-ethoxy-3-nitro-1,1'-biphenyl-4-yloxycarbonyl)-phenoxy]-decyl methacrylate
10-[4-(4'-propoxy-3-nitro-1,1'-biphenyl-4-yloxycarbonyl)-phenoxy]-decyl methacrylate
10-[4-(4'-butoxy-3-nitro-1,1'-biphenyl-4-yloxycarbonyl)phenoxy]-decyl methacrylate
10-[4-(4'-pentyloxy-3-nitro-1,1'-biphenyl-4-yloxycarbonyl)phenoxy]-decyl methacrylate
10-[4-(4'-hexyloxy-3-nitro-1,1'-biphenyl-4-yloxycarbonyl)phenoxy]-decyl methacrylate b) A solution of 0.53 g of 6-[4-(4'-methoxy-3-nitro-1,1'-biphenyl-4-yloxycarbonyl)-phenoxy]-hexyl methacrylate and 3.3 mg of azobisisobutyronitrile in 5 ml of 1-methyl-2-pyrrolidone is heated at 60° C. for 20 hours. Reprecipitating the product twice from ethanol gives a slightly yellow, glass-like polymer of N 148° I.

EXAMPLE C

A solution of 1.3 g of c-4-[4'-octyloxy-1,1'-biphenyl-4-yl]-1-(4-methacryloyloxybutyl)-r-1-cyclohexylcarbonitrile (from Example 6) and 8 mg of azobisisobutyronitrile in 6.5 ml of toluene is heated at 60° under nitrogen for 20 hours. Purification by reprecipitation from ethanol gives a colorless, fibrous polymer of $S_C$ 180° $S_A$ 260° I.

EXAMPLE D

A solution of 942 mg of c-4-[4'-(11-methacryloyloxyundecyloxy)-1,1'-biphenyl-4-yl]-1-octyl-r-1-carbonitrile (from Example 9) and 5 mg of azobisisobutyronitrile in 5 ml of toluene is heated at 60° under $N_2$ for 20 hours. The polymer is reprecipitated from methanol to give a white, fibrous polymer having the phase sequence G 70° $S_X$ 121° $S_C$ 140° $S_A$ 202° I.

EXAMPLE E

A white, fibrous polymer which exhibits a broad liquid-crystal range is obtained analogously to Example C from 4.8 g of 4'-octyloxy-1,1'-biphenyl-4-yl c-4-cyano-t-4-(6-methacryloyloxyhexyl)-r-1-cyclohexylcarboxylate (from Example 13).

EXAMPLE F

A polymer which exhibits a broad liquid-crystal range is obtained analogously to Example C from 4'-octyloxy-1,1'-biphenyl-4-yl c-4-cyano-t-4-(6-acryloyloxyhexyl)-r-1-cyclohexylcarboxylate (from Example 14).

EXAMPLE G 1.0 g of 4-(5-heptylpyridin-2-yl)-phenyl 4-(6-methacryloyloxyhexyloxy)-benzoate (from Example 15) is polymerized using azobisisobutyronitrile in N-methylpyrrolidone under $N_2$ at 60° for 20 hours. Working up gives a colorless polymer which has a broad liquid-crystal phase range.

EXAMPLE H

A colorless polymer which has a broad liquid-crystal phase range is obtained analogously to Example G from c-4-[4'-(R)-2-chloro-3-methylbutyryloxy-1,1'-biphenyl-4-yl]-1-(11-methacryloyloxyundecyl)-r-1-cyclohexylcarbonitrile (from Example 16).

EXAMPLE I

The corresponding polymer product, which has a broad liquid-crystal phase range, is obtained analogously to Example G from c-4-[4'-(2-methylbutyloxy)-1,1'-biphenyl-4-yl]-1-(11-methacryloylundecyl)-r-1-cyclohexylcarbonitrile (optically active).

EXAMPLE J

A solution of 1.10 g of c-4-[4'-(2-methylbutoxy)-1,1'-biphenyl-4-yl]-1-(undec-10-enyl)-r-1-cyclohexylcarbonitrile (optically active), 120 mg of polymethylhydridosiloxane and 80 μl of a 0.4% solution of hexachloroplatinic acid in 98:2 THF/ethanol is heated at 80°. The grafting is complete after 2 days and the polymer which has a broad liquid-crystal phase range, is obtained by precipitation from ethanol.

EXAMPLE K c-4-[4'-Octyloxy-1,1'-biphenyl-4-yl]-1-[2-methyl-3-oxa-14-(methacryloyloxy)-tetradecyl]-r-1-cyclohexylcarbonitrile (optically active) is polymerized analogously to Example G to give a colorless polymer which has a broad liquid-crystal phase range.

EXAMPLE L

4'-(2-Cyano-2-methylhexanoyloxy)-1,1'-biphenyl-4-yl 4-(6-acryloyloxyhexyloxy)-benzoate, optically active, (which can be prepared by the following route:
a) a solution of 22.7 g of DCCI in 20 ml of $CH_2Cl_2$ is added at 0° to a mixture of 18.6 g of 4,4'-dihydroxy-1,1'-biphenyl, 15.5 g of (S)-2-cyano-2-methylhexanoic acid, 1.2 g of 4-dimethylaminopyridine and 100 ml of $CH_2Cl_2$, and the mixture is stirred at room temperature for 2 hours. The precipitate is filtered off with suction, the filtrate is concentrated and chromatography over silica gel gives 4'-(2-cyano-2-methylhexanoyloxy)-4-hydroxy-1,1'-biphenyl (optically active).
b) A solution of 2.27 g of DCCI in 2 ml of $CH_2Cl_2$ is against (sic) at 0° to a solution of 3.23 g of a), 2.92 g of 4-(6-acryloyloxyhexyloxy)-benzoic acid and 0.12 g of 4-dimethylaminopyridine in 10 ml of $CH_2Cl_2$, and the mixture is stirred at room temperature for 2 hours. The precipitate is filtered off, the filtrate is concentrated and the residue is chromatographed over silica gel)

is polymerized analogously to Example G to give colorless poly-{4'-(2-cyano-2-methylhexanoyloxy)-1,1'-biphenyl-4-yl 4-(6-(acryloyloxyhexyloxy)-benzoate}, which has a broad liquid-crystal phase range.

We claim:

1. A polymer composition which exhibits a liquid-crystal phase and which contains, attached laterally to the polymer backbone as a side chain at least one mesogenic group, wherein the mesogenic group corresponds to the Formula XI $$R^1-(A^1-Z)_n-A^2-Sp-\qquad XI$$

in which $R^1$ is H or an alkyl group which has up to 15 C atoms and in which one or more $CH_2$ groups can also be replaced by a grouping belonging to the group comprising —O—, —S—, —O—CO—O—, —CO—, —CO—O—, —O—CO—, —CRR'—T—, —CO—S—, —S—CO, —CH=CH—(trans), —C(halogen)$_2$—, —SO— and —SO$_2$—, 2 heteroatoms not being attached to one another, or is halogen, CN, or —NCS, $A^1$ and $A^2$ independently of one another are each an unsubstituted or a halogen- and/or CN— and/or $CH_3$— and/or $NO_2$-monosubstituted or -polysubstituted 1,4-cyclohexylene group, in which one or two non-adjacent $CH_2$ groups can also be replaced by —O— and/or —S— atoms, and/or a $CH_2$ group can also be replaced by —CO—, or a 1,4-phenylene group, in which one or more CH groups can also be replaced by N, a piperidine-1,4-diyl group or a 1,4-bicyclo(2,2,2)octylene group, n is 1, 2, or 3, the Zs are each —CO—O, —O—CO, —CH$_2$CH$_2$—, —CRR'—T—, —CH$_2$—CO—, —CO—CH$_2$—, —CHCN—CH$_2$—, —CH$_2$—CHCN—, —CH=CH—, OCH$_2$—, —CH$_2$—O—, C≡C, —CH=CNO$_2$—, —CHNO$_2$—, —CH=N—, —N=CH—, —NO=O—, —N=NO—, —N=N—, or a single bond, Sp is alkylene which is 2-18 C atoms and in which one or two non-adjacent $CH_2$ groups can also be replaced by —O—, —CO—, —O—CO—, —CO—O—, —C(halogen)$_2$—, —CRR'—T—, —CH=CNO$_2$—, —CHNO$_2$—, —CHCN—, —CH=N—, or —CH=CH—, T is —COO—, —OCO—, or a single bond, R is H or an alkyl group having up to 6 C atoms, and R' is halogen or CN, and wherein at least one transversely polarizing structural element is present in the mesogenic group of Formula XI, said element corresponding to the Formulae I, II, or IV to X

 I

 II

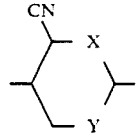 IV

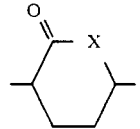 V

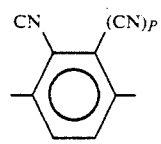 VI

 VII

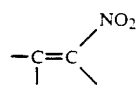 VIII

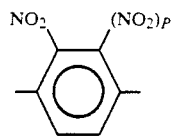 IX

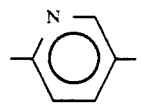 X in which X and Y independently of one another are —CH$_2$—, —O—, or —S—, R is H or an alkyl group having up to 6 C atoms, T is —COO—, —OCO—, or a single bond and p is 0 or 1.

2. In a polymer composition suitable as an organic substrate in electronics for fiber and films technology, comprising at least one polymer having a liquid crystalline phase is a composition of claim 1.

3. In a polymer composition suitable as a material for non-linear optics, comprising at least one polymer having a liquid crystalline phase, the improvement wherein said polymer having a liquid crystalline phase is a composition of claim 1.

* * * * *